(12) United States Patent
Davidson et al.

(10) Patent No.: US 7,504,522 B2
(45) Date of Patent: Mar. 17, 2009

(54) AZETIDINECARBOXAMIDE DERIVATIVES AND THEIR USE IN THE TREATMENT OF CB1 RECEPTOR MEDIATED DISORDERS

(75) Inventors: James Edward Paul Davidson, Winnersh (GB); Claire Elizabeth Dawson, Winnersh (GB); Kerry Harrison, Winnersh (GB); Howard Langham Mansell, Winnersh (GB); Robert Mark Pratt, Winnersh (GB); Sukhjit Sohal, Winnersh (GB); Victoria Jane Ruston, Winnersh (GB)

(73) Assignee: Vernalis Research Limited (GB)

( * ) Notice: Subject to any disclaimer, the term of this patent is extended or adjusted under 35 U.S.C. 154(b) by 173 days.

(21) Appl. No.: 10/552,575

(22) PCT Filed: Apr. 29, 2004

(86) PCT No.: PCT/GB2004/001831

§ 371 (c)(1),
(2), (4) Date: Aug. 4, 2006

(87) PCT Pub. No.: WO2004/096763

PCT Pub. Date: Nov. 11, 2004

(65) Prior Publication Data

US 2007/0054891 A1    Mar. 8, 2007

(30) Foreign Application Priority Data

May 1, 2003    (GB) .................................. 0310056.7

(51) Int. Cl.
*C07D 205/00* (2006.01)
*A61K 31/397* (2006.01)
(52) U.S. Cl. ........................ 548/950; 548/952; 548/953; 514/210.01; 514/210.17
(58) Field of Classification Search ................ 548/950, 548/952, 953; 514/210.01, 210.17
See application file for complete search history.

(56) References Cited

U.S. PATENT DOCUMENTS

| 6,403,574 B1 * | 6/2002 | Adams et al. .......... 514/210.17 |
| 6,566,356 B2 * | 5/2003 | Achard et al. .......... 514/210.01 |
| 2002/0019383 A1 * | 2/2002 | Achard et al. ............ 514/210.2 |

FOREIGN PATENT DOCUMENTS

WO    WO 99/37612 A    7/1999

OTHER PUBLICATIONS

Anxiety [online], [retrieved on Apr. 2, 2008]. Retrieved from the Internet, URL: http://www.nlm.nih.gov/medlineplus/anxiety.html#cat3.*
Autism [online], [retrieved on Apr. 2, 2008]. Retrieved from the Internet, URL: http://www.nlm.nih.gov/medlineplus/autism.html.*
Epilepsy [online], [retrieved on Apr. 2, 2008]. Retrieved from the Internet, URL: http://www.nlm.nih.gov/medlineplus/epilepsy.html.*
Parkinson's Disease [online], [retrieved on Apr. 2, 2008]. Retrieved from the Internet, URL: http://www.nlm.nih.gov/medlineplus/parkinsonsdisease.html.*
Dementia [online], [retrieved on Apr. 2, 2008]. Retrieved from the Internet, URL: http://www.nlm.nih.gov/medlineplus/dementia.html#cat5.*
Diabetes Mellitus [online], [retrieved on Apr. 2, 2008]. Retrieved from the Internet, URL: http://www.merck.com/mmpe/print/sec12/ch158/ch158b.html.*
Smoking Cessation [online], [retrieved on Apr. 2, 2008]. Retrieved from the Internet, URL:http://www.nlm.nih.gov/medlineplus/smokingcessation.html.*
Stella, Valentino J, Expert Opinion of Therapeutic Patents, Prodrugs as therapeutics, 2004 14(3): 277-280.*
Attention Deficit Hyperactivity Disorder [online], [retrieved on Apr. 2, 2008]. Retrieved from the Internet, URL: http://www.nlm.nih.gov.medlineplus/attentiondeficithyperactivitydisorder.html#cat3.*
Carai, Mauro A. "Efficacy of Rimonabant and Other Cannabinoid CB1 Receptor Antagonists in Reducing Food Intake and Body Weight: Preclinical and Clinical Data." CNS Drug Reviews 12(2)(2006): 91-99.*
Jensen, Michael D. "Discussion Following Dr. Jensen's Presentation." The American Journal of Medicine 120 (9A)(2007): 531-2.*

* cited by examiner

*Primary Examiner*—Kamal A Saeed
*Assistant Examiner*—Samantha L Shterengarts
(74) *Attorney, Agent, or Firm*—Banner & Witcoff, Ltd.

(57) ABSTRACT

Compounds of formula (I) and their use in therapy, particularly for the treatment of a disorder mediated by $CB_1$ receptors such as obesity: Formula (I) wherein: $R^1$ and $R^2$ are independently selected from aryl; and $R^3$ is hydrogen or alkyl; or a pharmaceutically acceptable salt or prodrug thereof, wherein at least one of $R^1$ and $R^2$ has a non-hydrogen substituent in the ortho-position(s) thereof relative to the point of attachment to the [—CH—O—] group.

(I)

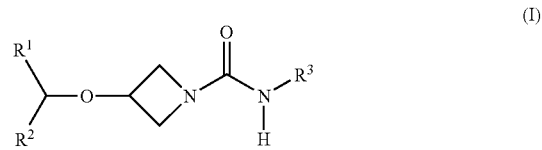

22 Claims, No Drawings

AZETIDINECARBOXAMIDE DERIVATIVES AND THEIR USE IN THE TREATMENT OF CB1 RECEPTOR MEDIATED DISORDERS

This application is a U.S. National Stage application of co-pending PCT application PCT/GB2004/001831, filed Apr. 29, 2004, which claims the priority of Great Britain Patent Application No. 0310056.7, filed May 1, 2003. These applications are incorporated herein by reference in their entireties.

The present invention relates primarily to the use of azetidine-1-carboxamides in the treatment of disorders mediated by the cannabinoid $CB_1$ receptor, particularly to the treatment of obesity and other eating disorders associated with excessive food intake.

It has been recognised that obesity is a disease process influenced by environmental factors in which the traditional weight loss methods of dieting and exercise need to be supplemented by therapeutic products (S. Parker, "Obesity: Trends and Treatments", Scrip Reports, PJB Publications Ltd, 1996).

Whether someone is classified as overweight or obese is generally determined on the basis of their body mass index (BMI) which is calculated by dividing body weight (kg) by height squared ($m^2$). Thus, the units of BMI are $kg/m^2$ and it is possible to calculate the BMI range associated with minimum mortality in each decade of life. Overweight is defined as a BMI in the range 25-30 $kg/m^2$, and obesity as a BMI greater than 30 $kg/m^2$. There are problems with this definition in that it does not take into account the proportion of body mass that is muscle in relation to fat (adipose tissue). To account for this, obesity can also be defined on the basis of body fat content: greater than 25% and 30% in males and females, respectively.

As the BMI increases there is an increased risk of death from a variety of causes that is independent of other risk factors. The most common diseases with obesity are cardiovascular disease (particularly hypertension), diabetes (obesity aggravates the development of diabetes), gall bladder disease (particularly cancer) and diseases of reproduction. Research has shown that even a modest reduction in body weight can correspond to a significant reduction in the risk of developing coronary heart disease.

Compounds marketed as anti-obesity agents include Orlistat (Reductil®) and Sibutramine. Orlistat (a lipase inhibitor) inhibits fat absorption directly and tends to produce a high incidence of unpleasant (though relatively harmless) side-effects such as diarrhoea. Sibutramine (a mixed 5-HT/noradrenaline reuptake inhibitor) can increase blood pressure and heart rate in some patients. The serotonin releaser/reuptake inhibitors fenfluramine (Pondimin®) and dexfenfluramine (Redux™) have been reported to decrease food intake and body weight over a prolonged period (greater than 6 months). However, both products were withdrawn after reports of preliminary evidence of heart valve abnormalities associated with their use. There is therefore a need for the development of a safer anti-obesity agent.

There now exists extensive pre-clinical and clinical data supporting the use of $CB_1$ receptor antagonists/inverse agonists for the treatment of obesity.

Preparations of marijuana (Cannabis sativa) have been used for over 5000 years for both medicinal and recreational purposes. The major psychoactive ingredient of marijuana has been identified as $\Delta^9$-tetrahydrocannabinol ($\Delta^9$-THC), one of a member of over 60 related cannabinoid compounds isolated from this plant. It has been demonstrated that $\Delta^9$-THC exerts its effects via agonist interaction with cannabinoid (CB) receptors. So far, two cannabinoid receptor subtypes have been characterised ($CB_1$, and $CB_2$). The $CB_1$ receptor subtype is found predominantly in the central nervous system, and to a lesser extent in the peripheral nervous system and various peripheral organs. The $CB_2$ receptor subtype is found predominantly in lymphoid tissues and cells. To date, three endogenous agonists (endocannabinoids) have been identified which interact with both $CB_1$ and $CB_2$ receptors (anandamide, 2-arachidonyl glycerol and noladin ether).

Genetically obese rats and mice exhibit markedly elevated endocannabinoid levels in brain regions associated with ingestive behaviour (Di Marzo et al. 2001 Nature 410: 822-825). Furthermore, increased levels of endocannabinoids are observed upon the fasting of normal, lean animals (Kirkham et al., British Journal of Pharmacology 2002, 136(4) 550-557). Exogenous application of endocannabinoids leads to the same physiological effects observed with $\Delta^9$-THC treatment, including appetite stimulation (Jamshida et al., British Journal of Pharmacology 2001, 134: 1151-1154), analgesia, hypolocomotion, hypothermia, and catalepsy.

$CB_1$ ($CB_1^{-/-}$) and $CB_2$ ($CB_2^{-/-}$) receptor knockout mice have been used to elucidate the specific role of the two cannabinoid receptor subtypes. Furthermore, for ligands such as $\Delta^9$-THC which act as agonists at both receptors, these mice have allowed identification of which receptor subtype is mediating specific physiological effects. $CB_1^{-/-}$, but not $CB_2^{-/-}$, mice are resistant to the behavioural effects of agonists such as $\Delta^9$-THC. $CB_1^{-/-}$ animals have also been shown to be resistant to both the body weight gain associated with chronic high fat diet exposure, and the appetite-stimulating effects of acute food deprivation.

These findings suggest a clear role for both endogenous and exogenous cannabinoid receptor agonists in increasing food intake and body weight via selective activation of the $CB_1$ receptor subtype.

The therapeutic potential for cannabinoid receptor ligands has been extensively reviewed (Exp. Opin. Ther. Pat. 1998, 8, 301-313; Exp. Opin. Ther. Pat. 2000, 10, 1529-1538; Trends in Pharm. Sci. 2000, 21, 218-224; Exp. Opin. Ther. Pat. 2002, 12(10), 1475-1489).

At least one compound (SR-141716A) characterised as a $CB_1$ receptor antagonist/inverse agonist is known to be in clinical trials for the treatment of obesity.

WO 00/15609, WO 01/64632, WO 01/64633 and WO 01/64634 disclose azetidine derivatives as $CB_1$ receptor antagonists. WO 02/28346 discloses the association of an azetidine derivative as a $CB_1$ receptor antagonist, and sibutramine, for the treatment of obesity.

There remains a medical need for low molecular weight $CB_1$ receptor antagonists/inverse agonists with pharmacokinetic and pharmacodynamic properties making them suitable for use as pharmaceutical agents. There also remains a medical need for new treatments of disorders mediated by the $CB_1$ receptor, particularly eating disorders, and particularly obesity. The object of the present invention is to provide such pharmaceutical agents and treatments.

It has now been found that certain azetidine-1-carboxamides show unexpected efficacy as anti-obesity agents. Compounds of this general formula were previously described in WO-A-99/37612 for the treatment of anxiety and epilepsy. These azetidine-1-carboxamides have been shown to selectively bind to the $CB_1$ receptor subtype with high affinity. Such compounds have been shown to dose-dependently block the effects of an exogenously applied cannabinoid receptor agonist (eg $?^9$-THC) in mice. Furthermore, such compounds have been shown to reduce food intake and body weight gain in both rat and mouse models of feeding behaviour.

According to the present invention, there is provided a compound of formula (I)

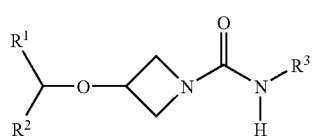

(I)

wherein:
$R^1$ and $R^2$ are independently selected from aryl; and
$R^3$ is hydrogen or alkyl;
or a pharmaceutically acceptable salt or prodrug thereof,
wherein at least one of $R^1$ and $R^2$ has a non-hydrogen substituent in the ortho-position(s) thereof relative to the point of attachment to the [—CH—O—] group.

The active compounds of formula (I) are antagonists and/or inverse agonists at the cannabinoid-1 ($CB_1$) receptor and are useful for the treatment, prevention and suppression of diseases mediated by the $CB_1$ receptor. The invention is concerned with the use of these compounds to selectively antagonise the $CB_1$ receptor and, as such, in the treatment of obesity and other disorders.

Reference in the present specification to an "alkyl" group means a branched or unbranched, cyclic or acyclic, saturated or unsaturated (e.g. alkenyl (including allyl) or alkynyl (including propargyl)) hydrocarbyl radical. Where cyclic or acyclic the alkyl group is preferably $C_1$ to $C_{12}$, more preferably $C_1$ to $C_8$ (such as methyl, ethyl, propyl, isopropyl, butyl, isobutyl, tert-butyl, sec-butyl, pentyl, isopentyl, hexyl, heptyl, octyl). It will be appreciated therefore that the term "alkyl" as used herein includes alkyl (branched or unbranched), alkenyl (branched or unbranched), alkynyl (branched or unbranched), cycloalkyl, cycloalkenyl and cycloalkynyl. A cyclic alkyl group may also be a mono-bridged or multiply-bridged cyclic alkyl group. In a preferred embodiment, a cyclic alkyl group is preferably $C_3$ to $C_{12}$, more preferably $C_5$ to $C_8$ and an acyclic alkyl group is preferably $C_1$ to $C_{10}$, more preferably $C_1$ to $C_6$, more preferably methyl, ethyl, propyl (n-propyl or isopropyl), butyl (n-butyl, isobutyl, tertiarybutyl or sec-butyl) or pentyl (including n-pentyl and iso-pentyl), more preferably methyl.

As used herein, the term "lower alkyl" means a branched or unbranched, cyclic or acyclic, saturated or unsaturated (e.g. alkenyl or alkynyl) hydrocarbyl radical wherein said cyclic lower alkyl group is $C_5$, $C_6$ or $C_7$, and wherein said acyclic lower alkyl group is $C_1$, $C_2$, $C_3$ or $C_4$. It will be appreciated therefore that the term "lower alkyl" as used herein includes lower alkyl (branched or unbranched), lower alkenyl (branched or unbranched), lower alkynyl (branched or unbranched), cycloloweralkyl, cycloloweralkenyl and cycloloweralkynyl. Preferably, a lower alkyl group is preferably selected from methyl, ethyl, propyl (n-propyl or isopropyl) or butyl (n-butyl, isobutyl, tertiary-butyl or sec-butyl), more preferably methyl.

Reference in the present specification to an "aryl" group means a mono or bicyclic aromatic group, such as phenyl or naphthyl, and preferably a mono-cyclic aromatic group.

Reference in the present specification to a "heteroaryl" group means an aromatic group containing one or more heteroatoms, preferably 1, 2 or 3 heteroatoms, preferably 1 or 2 heteroatoms. Preferably the heteroatoms are selected from O, S and N, preferably from O and N. Preferably the heteroaryl group comprises 5 or 6-membered ring systems. The heteroaryl group is preferably a monocyclic or bicyclic ring system, preferably monocyclic. Examples include thienyl, furanyl, pyrrolyl, imidazolyl, pyrazolyl, thiazolyl, isothiazolyl, oxazolyl, isoxazolyl, pyridyl, pyrazinyl, pyrimidinyl, quinolinyl, isoquinolinyl, benzofuranyl and isobenzofuryl.

Reference in the present specification to a non-aromatic heterocylic group is to a saturated or partially unsaturated 4, 5, 6 or 7-membered ring containing 1, 2 or 3 heteroatoms selected from N, O and S, preferably 1 or 2 heteroatoms, preferably selected from N and O. Examples include piperidinyl, morpholinyl, piperazinyl and pyrrolidinyl.

The alkyl, aryl and heteroaryl groups may be substituted or unsubstituted. In one embodiment, only the alkyl, aryl and heteroaryl groups defined herein as $R^1$ to $R^{16}$ may be substituted. Where $R^7$ and $R^8$ together form a 5 or 6-membered ring, the ring may be substituted or unsubstituted. Where substituted, there will generally be 1 to 3 substituents present, preferably 1 or 2 substituents. Substituents may include:

carbon containing groups such as
alkyl
aryl, arylalkyl (e.g. substituted and unsubstituted phenyl, substituted and unsubstituted benzyl);

halogen atoms and halogen containing groups such as
haloalkyl (e.g. trifluoromethyl);

oxygen containing groups such as
alcohols (e.g. hydroxy, hydroxyalkyl, (aryl)(hydroxy)alkyl),
ethers (e.g. alkoxy, alkoxyalkyl, aryloxyalkyl),
aldehydes (e.g. carboxaldehyde),
ketones (e.g. alkylcarbonyl, alkylcarbonylalkyl, arylcarbonyl, arylalkylcarbonyl, arylcarbonylalkyl),
acids (e.g. carboxy, carboxyalkyl),
acid derivatives such as esters
(e.g. alkoxycarbonyl, alkoxycarbonylalkyl, alkylcarbonyloxy, alkylcarbonyloxyalkyl) and amides
(e.g. aminocarbonyl, mono- or dialkylaminocarbonyl, aminocarbonylalkyl, mono- or dialkylaminocarbonylalkyl, arylaminocarbonyl);

nitrogen containing groups such as
amines (e.g. amino, mono- or dialkylamino, aminoalkyl, mono- or dialkylaminoalkyl),
azides,
nitriles (e.g. cyano, cyanoalkyl),
nitro;

sulphur containing groups such as
thiols, thioethers, sulphoxides and sulphones
(e.g. alkylthio, alkylsulfinyl, alkylsufonyl, alkylthioalkyl, alkylsulfinylalkyl, alkylsulfonylalkyl, arylthio, arylsulfinyl, arylsulfonyl, arylthioalkyl, arylsulfinylalkyl, arylsulfonylalkyl);

and heterocyclic groups containing one or more, preferably one, heteroatom,
(e.g. thienyl, furanyl, pyrrolyl, imidazolyl, pyrazolyl, thiazolyl, isothiazolyl, oxazolyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, piperazinyl, morpholinyl, thionaphthyl, benzofuranyl, isobenzofuryl, indolyl, oxyindolyl, isoindolyl, indazolyl, indolinyl, 7-azaindolyl, isoindazolyl, benzopyranyl, coumarinyl, isocoumarinyl, quinolyl, isoquinolyl, naphthridinyl, cinnolinyl, quinazolinyl, pyridopyridyl, benzoxazinyl, quinoxadinyl, chromenyl, chromanyl, isochromanyl and carbolinyl).

Where an aryl group is phenyl, the phenyl may be substituted by adjacent substituents forming a 5 or 6 membered saturated ring optionally containing 1 or 2 heteroatoms, preferably selected from N, O and S, preferably from N and O. Where the saturated ring contains 2 nitrogen atoms, the ring is preferably a 6-membered ring. Where the saturated ring contains 2 oxygen atoms, the ring may be a 5- or 6-membered ring. Examples include 2,3-dihydrobenzo[b]furan-7-yl, 2,3-dihydrobenzo[b]thiophen-6-yl, 1,2,3,4-tetrahydronaphthalen-5-yl, 2,3-dihydrobenzo[1,4]dioxin-6-yl and 1,2,3,4-tetrahydroisoquinolin-8-yl.

Preferred substituents include alkyl (including haloalkyl), alkoxy (including haloalkoxy), aryl, nitrile or halo. Preferred halogen-containing groups include trifluoromethyl.

As used herein, the term "alkoxy" means alkyl-O— and "alkoyl" means alkyl-CO—.

As used herein, the term "halogen" means a fluorine, chlorine, bromine or iodine radical, preferably a fluorine or chlorine radical.

The compounds of formula (I) may exist in a number of diastereomeric and/or enantiomeric forms. Unless otherwise stated, reference in the present specification to "a compound of formula (I)" is a reference to all stereoisomeric forms of the compound and includes a reference to the unseparated stereoisomers in a mixture, racemic or non-racemic, and to each stereoisomer in its pure form.

In the compounds of formula (I), preferably $R^1$ and $R^2$ are independently selected from substituted or unsubstituted phenyl or naphthyl (preferably phenyl), more preferably substituted phenyl or naphthyl (preferably phenyl), more preferably phenyl or naphthyl (preferably phenyl) having 1 to 3 substituents and most preferably phenyl or naphthyl (preferably phenyl) having 1 or 2 substituents. In one embodiment the substituent groups are selected from halogen and haloalkyl (particularly trifluoromethyl). Preferably $R^1$ and $R^2$ are selected from mono-cyclic aromatic groups.

In a preferred embodiment of the compounds of formula (I), $R^1$ and $R^2$ are independently selected from a group of formula:

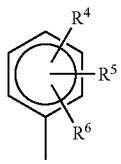

wherein $R^4$, $R^5$ and $R^6$ are independently selected from hydrogen, halo, alkyl (including haloalkyl), thioalkyl, alkoxy (including haloalkoxy), alkylsulfonyl, amino, mono- and di-alkyl amino, mono- and di-aryl amino, alkylarylamino, aminoalkyl, alkylaminoalkyl, dialkylaminoalkyl, $NR^{14}C(O)R^{15}$, $NR^{14}SO_2R^{16}$, $COOR^{15}$, $OC(O)R^{16}$, $CONR^7R^8$ and $SO_2NR^7R^8$, wherein $R^7$ and $R^8$ are independently selected from hydrogen and alkyl or may form a 5 or 6 membered ring optionally containing 1 or 2 additional heteroatoms selected from N, O and S; and wherein $R^{14}$ is selected from H and lower alkyl (preferably H), $R^{15}$ is selected from H, alkyl, aryl and heteroaryl (preferably alkyl, preferably lower alkyl) and $R^{16}$ is selected from alkyl, aryl and heteroaryl (preferably alkyl, preferably lower alkyl). The groups $R^1$ and $R^2$ may be the same or different, and in one embodiment are different.

Where $R^4$, $R^5$ and $R^6$ are selected from halo, the halo group is preferably fluoro, chloro, bromo or iodo, preferably chloro or bromo. Where $R^4$, $R^5$ and $R^6$ are selected from alkyl, thioalkyl, alkoxy and alkylsulfonyl, the alkyl is preferably selected from lower alkyl, and preferably from methyl and ethyl, preferably methyl. Where $R^4$, $R^5$ and $R^6$ are selected from aminoalkyl, alkylaminoalkyl and dialkylaminoalkyl, the alkyl is preferably selected from lower alkyl, and preferably from methyl and ethyl, preferably methyl. Where $R^4$, $R^5$ and $R^6$ are selected from dialkylaminoalkyl, the dialkylamino fragment is preferably selected from cyclicamino, preferably from morpholino and piperazino. Where $R^4$, $R^5$ and $R^6$ are selected from haloalkyl, the alkyl is preferably methyl, and the $R^4$, $R^5$ or $R^6$ group is preferably trifluoromethyl. Where $R^4$, $R^5$ and $R^6$ are selected from haloalkoxy, the alkyl is preferably methyl and the $R^4$, $R^5$ or $R^6$ group is preferably selected from trifluoromethoxy or difluoromethoxy, preferably difluoromethoxy. Preferably one or two of $R^4$, $R^5$ and $R^6$ are hydrogen. At least one of the $R^1$ and $R^2$ groups has a non-hydrogen substituent in the ortho-position(s). The $R^1$ or $R^2$ groups may independently have one or two non-hydrogen substituents in the ortho position(s) relative to the point of attachment to the [—CH—O—] group. Preferred ortho-substituents include halo and haloalkyl, as described herein. Particularly preferred ortho-substituents are chloro and trifluoromethyl, particularly trifluoromethyl.

Where $R^7$ and $R^8$ form a 5- or 6-membered ring, the ring is preferably 6-membered, and is preferably saturated or partially saturated, preferably saturated. Where the ring contains additional heteroatoms, these are preferably selected from N and O. Preferably there are 0 or 1 additional heteroatoms.

In the compounds of formula I, $R^3$ is selected from hydrogen or alkyl, preferably alkyl.

Where $R^3$ is selected from alkyl, preferably $R^3$ is lower alkyl, and preferably methyl, ethyl, propyl and butyl as described above. The alkyl group may be substituted or unsubstituted, and in one embodiment is substituted. One or two substituent groups may be present, preferably one substituent group. Preferred substituents are those referred to hereinabove, particularly hydroxy, alkoxy, thioalkyl, amino, mono- and dialkyl amino, alkoxycarbonyl, aryl (preferably phenyl), and heterocyclic groups including both heteroaryl and non-aromatic heterocyclic groups. Where $R^3$ is an acyclic alkyl group, it may be substituted by a cyclic alkyl group; and where $R^3$ is a cyclic alkyl group it may be substituted by an acyclic alkyl group. Where the substituent group is heteroaryl, the heteroaryl preferably is a 5- or 6-membered ring containing one or more N, O or S atoms, and preferred groups include thiophenyl, furanyl, isoxazolyl, thiazolyl and benzothiophenyl. Other preferred substituent groups include dihydrobenzofuranyl, dihydrobenzodioxinyl, tetrahydrofuranyl, pyrrolidinyl, oxopyrrolindyl and benzodioxolyl.

In one embodiment, $R^3$ is selected from:

$$—(CHR^9)_n(CH_2)_mCR^{10}R^{11}R^{12}$$

wherein n is 0 or 1;

m is 0, 1, 2 or 3;

$R^9$, $R^{10}$, $R^{11}$ and $R^{12}$ are selected from hydrogen, alkyl (preferably lower alkyl), hydroxy, alkoxy (preferably lower alkoxy), thioalkyl (preferably thio lower alkyl), amino, mono- and di-alkyl amino (preferably lower alkyl amino), alkoxycarbonyl (preferably lower alkoxy carbonyl) and $R^{13}$;

wherein $R^{13}$ is selected from aryl, heteroaryl and non-aromatic heterocyclic optionally substituted by one or more (preferably 1 or 2, preferably 1) groups preferably selected from alkyl (preferably lower alkyl, preferably methyl), halogen (preferably fluoro, chloro and bromo), alkoxy (preferably lower alkoxy, preferably methoxy), oxo, aryl, heteroaryl and non-aromatic heterocycle.

Preferably, m is 0 or 1 or 2, preferably 0 or 1, and preferably 0.

Preferably, n is 0.

In one embodiment, at least one and more preferably two of $R^{10}$, $R^{11}$ and $R^{12}$ are selected from hydrogen. In a further embodiment, at least one and more preferably at least two of $R^{10}$, $R^{11}$ and $R^{12}$ are selected from methyl.

In a further embodiment, $R^3$ is selected from cyclic alkyl, including cyclopentyl, cyclohexyl, norbornanyl and adamantyl, preferably cyclopentyl and cyclohexyl.

Preferred $R^3$ groups are tertiary butyl, sec-butyl, isobutyl, isopropyl, n-propyl and ethyl, particularly tertiary butyl, isobutyl, sec-butyl and isopropyl, and particularly tertiary butyl.

Preferred compounds are as follows:

3-(2,4,4'-trichlorobenzhydryloxy)-N-(tert-butyl)azetidine-1-carboxamide
3-(2,4'-dichlorobenzhydryloxy)-N-(ethyl propionate-2-yl)azetidine-1-carboxamide
3-(2,4'-dichlorobenzhydryloxy)-N-(tert-butyl)azetidine-1-carboxamide
3-(2,4'-dichlorobenzhydryloxy)-N-(2-thiophen-2-yl ethyl)azetidine-1-carboxamide
3-(2,4'-dichlorobenzhydryloxy)-N-[ethyl 4-(methylthio)butyrate-2-yl]azetidine-1-carboxamide
3-(2,4'-dichlorobenzhydryloxy)-N-(cyclopropylmethyl)azetidine-1-carboxamide
3-(2,4'-dichlorobenzhydryloxy)-N-(2,3-dihydrobenzofuran-5-yl-methyl)azetidine-1-carboxamide
3-(2,4'-dichlorobenzhydryloxy)-N-(2,5-dimethylfuran-3-yl-methyl)azetidine-1-carboxamide
3-(2,4'-dichlorobenzhydryloxy)-N-(2,3-Dihydro-benzo[1,4]dioxin-2-yl-methyl)azetidine-1-carboxamide
3-(2,4'-dichlorobenzhydryloxy)-N-(5-methyl-isoxazol-3-yl-methyl)azetidine-1-carboxamide
3-(2,4'-dichlorobenzhydryloxy)-N-[(R)-sec-butyl]azetidine-1-carboxamide
3-(2,4'-dichlorobenzhydryloxy)-N-(2-bromothiophen-3-yl-methyl)azetidine-1-carboxamide
3-(2,4'-dichlorobenzhydryloxy)-N-[(S)-sec-butyl] azetidine-1-carboxamide
3-(2,4'-dichlorobenzhydryloxy)-N-(thiophen-3-yl-methyl)azetidine-1-carboxamide
3-(2,4'-dichlorobenzhydryloxy)-N-(2-methoxyphenylmethyl)azetidine-1-carboxamide
3-(2,4'-dichlorobenzhydryloxy)-N-(2-furanylmethyl)azetidine-1-carboxamide
3-(2,4'-dichlorobenzhydryloxy)-N-(3-ethoxypropyl)azetidine-1-carboxamide
3-(2,4'-dichlorobenzhydryloxy)-N-(2-tetrahydrofuranylmethyl)azetidine-1-carboxamide
3-(2,4'-dichlorobenzhydryloxy)-N-(exo-2-norbornanyl)azetidine-1-carboxamide
3-(2,4'-dichlorobenzhydryloxy)-N-(1-phenylpropyl)azetidine-1-carboxamide
3-(2,4'-dichlorobenzhydryloxy)-N-[(R)-a-methylbenzyl]azetidine-1-carboxamide
3-(2,4'-dichlorobenzhydryloxy)-N-[(R)-1-(3-methoxyphenyl)ethyl]azetidine-1-carboxamide
3-(2,4'-dichlorobenzhydryloxy)-N-[(S)-1-(3-methoxyphenyl)ethyl]azetidine-1-carboxamide
3-(4,4'-dichlorobenzhydryloxy)-N-(1-adamantyl)azetidine-1-carboxamide
3-(4,4'-dichlorobenzhydryloxy)-N-(benzo[b]thiophen-2-yl-methyl)azetidine-1-carboxamide
3-(2,2'-dichlorobenzhydryloxy)-N-(1-adamantyl)azetidine-1-carboxamide
3-(4,4'-dibromobenzhydryloxy)-N-(tert-butyl)azetidine-1-carboxamide
3-(4,4'-dibromobenzhydryloxy)-N-(1-adamantyl)azetidine-1-carboxamide
3-[2-(trifluoromethyl)-4'-chlorobenzhydryloxy]-N-(tert-butyl)azetidine-1-carboxamide
3-[2-(trifluoromethyl)-4'-chlorobenzhydryloxy]-N-(n-propyl)azetidine-1-carboxamide
3-[2-(trifluoromethyl)-4'-chlorobenzhydryloxy]-N-(iso-propyl)azetidine-1-carboxamide
3-[2-(trifluoromethyl)-4'-chlorobenzhydryloxy]-N-(n-butyl)azetidine-1-carboxamide
3-[2-(trifluoromethyl)-4'-chlorobenzhydryloxy]-N-(sec-butyl)azetidine-1 carboxamide
3-[2-(trifluoromethyl)-4'-chlorobenzhydryloxy]-N-(ethyl propionate-3-yl)azetidine-1-carboxamide
3-[2-(trifluoromethyl)-4'-chlorobenzhydryloxy]-N-(ethyl 3-phenylpropionate-2-yl)azetidine-1-carboxamide
3-[2-(trifluoromethyl)-4'-chlorobenzhydryloxy]-N-(ethyl)azetidine-1-carboxamide
3-[2-(trifluoromethyl)-4'-chlorobenzhydryloxy]-N-[(S)-a-methyl-benzyl]azetidine-1-carboxamide
3-[2-(trifluoromethyl)-4'-chlorobenzhydryloxy]-N-(2,2,4-trimethylpent-4-yl)azetidine-1-carboxamide
3-[2-(trifluoromethyl)-4'-chlorobenzhydryloxy]-N-(cyclopentyl)azetidine-1-carboxamide
3-(2,4'-dichlorobenzhydryloxy)-N-(2,2,4-trimethylpent-4-yl)azetidine-1-carboxamide
3-(2,4'-dichlorobenzhydryloxy)-N-(2-methylbut-2-yl)azetidine-1-carboxamide
3-[2-(trifluoromethyl)-2'-fluoro-4'-bromobenzhydryloxy]-N-(tert-butyl)azetidine-carboxamide
3-[2-(trifluoromethyl)-4'-(methylthio)benzhydryloxy]-N-(tert-butyl)azetidine-1-carboxamide
3-[2-(trifluoromethyl)-4'-(methylthio)benzhydryloxy]-N-(iso-propyl)azetidine-1-carboxamide
3-[2-(trifluoromethyl)-4'-(methylthio)benzhydryloxy]-N-(sec-butyl)azetidine-1-carboxamide
3-[2-(trifluoromethyl)-4'-(methylthio)benzhydryloxy]-N-(benzyl)azetidine-1-carboxamide
3-[2-(trifluoromethyl)-4-fluoro-4'-chlorobenzhydryloxy]-N-(tert-butyl)azetidine-1-carboxamide
3-[2-(trifluoromethyl)-4-fluoro-4'-chlorobenzhydryloxy]-N-(iso-propyl)azetidine-carboxamide
3-[2-(trifluoromethyl)-4-fluoro-4'-chlorobenzhydryloxy]-N-(sec-butyl)azetidine-1-carboxamide
3-[2-(trifluoromethyl)-4-fluoro-4'-chlorobenzhydryloxy]-N-(cyclohexyl)azetidine-1-carboxamide
3-[2-(trifluoromethyl)-4-fluoro-4'-chlorobenzhydryloxy]-N-(benzyl)azetidine-1-carboxamide
3-[2-(trifluoromethyl)benzhydryloxy]-N-(tert-butyl)azetidine-1-carboxamide
3-[2-(trifluoromethyl)benzhydryloxy]-N-(iso-propyl)azetidine-1-carboxamide
3-[2-(trifluoromethyl)benzhydryloxy]-N-(sec-butyl)azetidine-1-carboxamide
3-[2-(trifluoromethyl)benzhydryloxy]-N-(cyclohexyl)azetidine-1-carboxamide
3-[2-(trifluoromethyl)benzhydryloxy]-N-(benzyl)azetidine-1-carboxamide
3-[2-(trifluoromethyl)-4'-(trifluoromethoxy)benzhydryloxy]-N-(tert-butyl)azetidine 1-carboxamide 3-[2-(trifluoromethyl)-4'-(trifluoromethoxy)benzhydryloxy]-N-(iso-propyl)azetidine-1-carboxamide
3-[2-(trifluoromethyl)-4'-(trifluoromethoxy)benzhydryloxy]-N-(sec-butyl)azetidine-1-carboxamide
3-[2-(trifluoromethyl)-4'-(trifluoromethoxy)benzhydryloxy]-N-(benzyl)azetidine-1-carboxamide
3-[2-(trifluoromethyl)-4'-chlorobenzhydryloxy]-N-(1-adamantyl)azetidine-1-carboxamide
3-[2-(trifluoromethyl)-4'-chlorobenzhydryloxy]-N-(cyclohexyl)azetidine-1-carboxamide
3-[2-(trifluoromethyl)-4'-chlorobenzhydryloxy]-N-(tert-amyl)azetidine-1-carboxamide
3-[2-(trifluoromethyl)-4'-methylbenzhydryloxy]-N-(1-adamantyl)azetidine-1-carboxamide
3-[2-(trifluoromethyl)-4'-methylbenzhydryloxy]-N-(tert-butyl)azetidine-1-carboxamide
3-[2-(trifluoromethyl)-4'-methylbenzhydryloxy]-N-(cyclohexyl)azetidine-1-carboxamide
3-[2-(trifluoromethyl)-4'-methoxybenzhydryloxy]-N-(1-adamantyl)azetidine-1-carboxamide
3-[2-(trifluoromethyl)-4'-methoxybenzhydryloxy]-N-(tert-butyl)azetidine-1-carboxamide
3-[2-(trifluoromethyl)-4'-fluorobenzhydryloxy]-N-(1-adamantyl)azetidine-1-carboxamide
3-[2-(trifluoromethyl)-4'-fluorobenzhydryloxy]-N-(tert-butyl)azetidine-1-carboxamide
3-[2-(trifluoromethyl)-4'-fluorobenzhydryloxy]-N-(cyclohexyl)azetidine-1-carboxamide
3-[2-(trifluoromethyl)-4'-chlorobenzhydryloxy]-N-(allyl)azetidine-1-carboxamide
3-[2-(trifluoromethyl)-4'-(methylthio)benzhydryloxy]-N-(1-adamantyl)azetidine-1-carboxamide
3-[2-(trifluoromethyl)-4'-(methylthio)benzhydryloxy]-N-(cyclohexyl)azetidine-1-carboxamide
3-[2-(trifluoromethyl)-4'-(difluoromethoxy)benzhydryloxy]-N-(tert-butyl)azetidine—carboxamide
3-[2-(trifluoromethyl)-4'-(difluoromethoxy)benzhydryloxy]-N-(sec-butyl)azetidine-1-carboxamide
3-[2-(trifluoromethyl)-4'-(difluoromethoxy)benzhydryloxy]-N-(iso-propyl)azetidine-1-carboxamide
3-[2-(trifluoromethyl)-4'-(difluoromethoxy)benzhydryloxy]-N-(cyclohexyl)azetidine-1-carboxamide
3-[2-(trifluoromethyl)-4'-(difluoromethoxy)benzhydryloxy]-N-(allyl)azetidine-1-carboxamide
3-[2-(trifluoromethyl)-4'-fluorobenzhydryloxy]-N-(sec-butyl)azetidine-1-carboxamide
3-[2-(trifluoromethyl)-4'-fluorobenzhydryloxy]-N-(iso-propyl)azetidine-1-carboxamide
3-[2-(trifluoromethyl)-4'-fluorobenzhydryloxy]-N-[(S)-a-methylbenzyl]azetidine-1-carboxamide
3-[2-(trifluoromethyl)-2'-fluoro-4'-(1-piperidinyloxomethyl)benzhydryloxy]-N-(tert-butyl)azetidine-1-carboxamide
3-[2-(trifluoromethyl)-2'-fluoro-4'-bromobenzhydryloxy]-N-(tert-butyl)azetidine-1-carboxamide, and
3-[(R*)-2-(trifluoromethyl)-4'-chlorobenzhydryloxy]-N-(tert-butyl)azetidine-1-carboxamide
Particularly preferred compounds are as follows:
3-(2,4,4'-trichlorobenzhydryloxy)-N-(tert-butyl)azetidine-1-carboxamide
3-(2,4'-dichlorobenzhydryloxy)-N-(tert-butyl)azetidine-1-carboxamide
3-(2,4'-dichlorobenzhydryloxy)-N-(2-thiophen-2-yl ethyl)azetidine-1-carboxamide
3-(2,4'-dichlorobenzhydryloxy)-N-(cyclopropylmethyl)azetidine-1-carboxamide
3-(2,4'-dichlorobenzhydryloxy)-N-(2,3-dihydrobenzofuran-5-yl-methyl)azetidine-1-carboxamide
3-(2,4'-dichlorobenzhydryloxy)-N-(2,5-dimethylfuran-3-yl-methyl)azetidine-1-carboxamide
3-(2,4'-dichlorobenzhydryloxy)-N-(2,3-Dihydro-benzo[1,4]dioxin-2-yl-methyl)azetidine-1-carboxamide
3-(2,4'-dichlorobenzhydryloxy)-N-(5-methyl-isoxazol-3-yl-methyl)azetidine-1-carboxamide
3-(2,4'-dichlorobenzhydryloxy)-N-[(R)-sec-butyl]azetidine-1-carboxamide
3-(2,4'-dichlorobenzhydryloxy)-N-(2-bromothiophen-3-yl-methyl)azetidine-1-carboxamide
3-(2,4'-dichlorobenzhydryloxy)-N-[(S)-sec-butyl]azetidine-1-carboxamide
3-(2,4'-dichlorobenzhydryloxy)-N-(thiophen-3-yl-methyl)azetidine-1-carboxamide
3-(2,4'-dichlorobenzhydryloxy)-N-(2-methoxyphenylmethyl)azetidine-1-carboxamide
3-(2,4'-dichlorobenzhydryloxy)-N-(2-furanylmethyl)azetidine-1-carboxamide
3-(2,4'-dichlorobenzhydryloxy)-N-(3-ethoxypropyl)azetidine-1-carboxamide
3-(2,4'-dichlorobenzhydryloxy)-N-(2-tetrahydrofuranylmethyl)azetidine-1-carboxamide
3-(2,4'-dichlorobenzhydryloxy)-N-(exo-2-norbornanyl)azetidine-1-carboxamide
3-(2,4'-dichlorobenzhydryloxy)-N-(1-phenylpropyl)azetidine-1-carboxamide
3-(2,4'-dichlorobenzhydryloxy)-N-[(R)-a-methylbenzyl]azetidine-1-carboxamide
3-(2,4'-dichlorobenzhydryloxy)-N-[(R)-1-(3-methoxyphenyl)ethyl]azetidine-1-carboxamide
3-(2,4'-dichlorobenzhydryloxy)-N-[(S)-1-(3-methoxyphenyl)ethyl]azetidine-1-carboxamide
3-[2-(trifluoromethyl)-4'-chlorobenzhydryloxy]-N-(n-butyl)azetidine-1-carboxamide
3-[2-(trifluoromethyl)-4'-chlorobenzhydryloxy]-N-(sec-butyl)azetidine-1-carboxamide
3-[2-(trifluoromethyl)-4'-chlorobenzhydryloxy]-N-(ethyl)azetidine-1-carboxamide
3-[2-(trifluoromethyl)-4'-chlorobenzhydryloxy]-N-[(S)-a-methyl-benzyl]azetidine-1-carboxamide
3-[2-(trifluoromethyl)-4'-chlorobenzhydryloxy]-N-(2,2,4-trimethylpent-4-yl)azetidine-1-carboxamide
3-[2-(trifluoromethyl)-4'-chlorobenzhydryloxy]-N-(cyclopentyl)azetidine-1-carboxamide
3-(2,4'-dichlorobenzhydryloxy)-N-(2,2,4-trimethylpent-4-yl)azetidine-1-carboxamide
3-(2,4'-dichlorobenzhydryloxy)-N-(2-methylbut-2-yl)azetidine-1-carboxamide
3-[2-(trifluoromethyl)-2'-fluoro-4'-bromobenzhydryloxy]-N-(tert-butyl)azetidine-1-carboxamide
3-[2-(trifluoromethyl)-4'-(methylthio)benzhydryloxy]-N-(tert-butyl)azetidine-1-carboxamide
3-[2-(trifluoromethyl)-4'-(methylthio)benzhydryloxy]-N-(iso-propyl)azetidine-1-carboxamide
3-[2-(trifluoromethyl)-4'-(methylthio)benzhydryloxy]-N-(sec-butyl)azetidine-1-carboxamide
3-[2-(trifluoromethyl)-4'-(methylthio)benzhydryloxy]-N-(benzyl)azetidine-1-carboxamide
3-[2-(trifluoromethyl)-4-fluoro-4'-chlorobenzhydryloxy]-N-(tert-butyl)azetidine-1-carboxamide
3-[2-(trifluoromethyl)-4-fluoro-4'-chlorobenzhydryloxy]-N-(iso-propyl)azetidine-1-carboxamide
3-[2-(trifluoromethyl)-4-fluoro-4'-chlorobenzhydryloxy]-N-(sec-butyl)azetidine-1-carboxamide 3-[2-(trifluoromethyl)-4-fluoro-4'-chlorobenzhydryloxy]-N-(cyclohexyl)azetidine-1-carboxamide
3-[2-(trifluoromethyl)-4-fluoro-4'-chlorobenzhydryloxy]-N-(benzyl)azetidine-1-carboxamide
3-[2-(trifluoromethyl)benzhydryloxy]-N-(tert-butyl)azetidine-1-carboxamide
3-[2-(trifluoromethyl)benzhydryloxy]-N-(iso-propyl)azetidine-1-carboxamide
3-[2-(trifluoromethyl)benzhydryloxy]-N-(sec-butyl)azetidine-1-carboxamide
3-[2-(trifluoromethyl)benzhydryloxy]-N-(cyclohexyl)azetidine-1-carboxamide
3-[2-(trifluoromethyl)benzhydryloxy]-N-(benzyl)azetidine-1-carboxamide
3-[2-(trifluoromethyl)-4'-(trifluoromethoxy)benzhydryloxy]-N-(tert-butyl)azetidine-1-carboxamide
3'-[2-(trifluoromethyl)-4'-(trifluoromethoxy)benzhydryloxy]-N-(iso-propyl)azetidine-1-carboxamide
3-[2-(trifluoromethyl)-4'-(trifluoromethoxy)benzhydryloxy]-N-(sec-butyl)azetidine-1-carboxamide
3-[2-(trifluoromethyl)-4'-(trifluoromethoxy)benzhydryloxy]-N-(benzyl)azetidine-1-carboxamide
3-[2-(trifluoromethyl)-4'-chlorobenzhydryloxy]-N-(1-adamantyl)azetidine-1-carboxamide
3-[2-(trifluoromethyl)-4'-chlorobenzhydryloxy]-N-(cyclohexyl)azetidine-1-carboxamide
3-[2-(trifluoromethyl)-4'-chlorobenzhydryloxy]-N-(tert-amyl)azetidine-1-carboxamide
3-[2-(trifluoromethyl)-4'-methylbenzhydryloxy]-N-(1-adamantyl)azetidine-1-carboxamide
3-[2-(trifluoromethyl)-4'-methylbenzhydryloxy]-N-(tert-butyl)azetidine-1-carboxamide
3-[2-(trifluoromethyl)-4'-methylbenzhydryloxy]-N-(cyclohexyl)azetidine-1-carboxamide
3-[2-(trifluoromethyl)-4'-methoxybenzhydryloxy]-N-(1-adamantyl)azetidine-1-carboxamide
3-[2-(trifluoromethyl)-4'-methoxybenzhydryloxy]-N-(tert-butyl)azetidine-1-carboxamide
3-[2-(trifluoromethyl)-4'-fluorobenzhydryloxy]-N-(1-adamantyl)azetidine-1-carboxamide
3-[2-(trifluoromethyl)-4'-fluorobenzhydryloxy]-N-(tert-butyl)azetidine-1-carboxamide
3-[2-(trifluoromethyl)-4'-fluorobenzhydryloxy]-N-(cyclohexyl)azetidine-1-carboxamide
3-[2-(trifluoromethyl)-4'-chlorobenzhydryloxy]-N-(allyl)azetidine-1-carboxamide
3-[2-(trifluoromethyl)-4'-(methylthio)benzhydryloxy]-N-(1-adamantyl)azetidine-1-carboxamide
3-[2-(trifluoromethyl)-4'-(methylthio)benzhydryloxy]-N-(cyclohexyl)azetidine-1-carboxamide
3-[2-(trifluoromethyl)-4'-(difluoromethoxy)benzhydryloxy]-N-(tert-butyl)azetidine-1-carboxamide
3-[2-(trifluoromethyl)-4'-(difluoromethoxy)benzhydryloxy]-N-(sec-butyl)azetidine-1-carboxamide
3-[2-(trifluoromethyl)-4'-(difluoromethoxy)benzhydryloxy]-N-(iso-propyl)azetidine-1-carboxamide
3-[2-(trifluoromethyl)-4'-(difluoromethoxy)benzhydryloxy]-N-(cyclohexyl)azetidine-1-carboxamide
3-[2-(trifluoromethyl)-4'-(difluoromethoxy)benzhydryloxy]-N-(allyl)azetidine-1-carboxamide
3-[2-(trifluoromethyl)-4'-fluorobenzhydryloxy]-N-(sec-butyl)azetidine-1-carboxamide
3-[2-(trifluoromethyl)-4'-fluorobenzhydryloxy]-N-[(S)-a-methylbenzyl]azetidine 1-carboxamide
3-[2-(trifluoromethyl)-2'-fluoro-4'-(1-piperidinyloxomethyl)benzhydryloxy]-N-(tert-butyl)azetidine-1-carboxamide
3-[2-(trifluoromethyl)-2'-fluorobenzhydryloxy]-N-(tert-butyl)azetidine-1-carboxamide, and
3-[(R*)-2-(trifluoromethyl)-4'-chlorobenzhydryloxy]-N-(tert-butyl)azetidine-1-carboxamide.

According to a further aspect of the invention, there is provided for use in therapy a compound of formula (I).

According to a further aspect of the invention, there is provided the use of a compound of formula (I) in the manufacture of a medicament for the treatment of a disorder mediated by $CB_1$ receptors.

According to a further aspect of the present invention there is provided a method of treatment of a disorder mediated by $CB_1$ receptors comprising administration to a subject in need of such treatment an effective dose of the compound of formula (I), or a pharmaceutically acceptable salt or prodrug thereof.

The disorders mediated by $CB_1$ receptors are selected from psychosis, memory deficit, cognitive disorders, attention deficit disorder, migraine, neuropathy, neuro-inflammatory disorders including multiple sclerosis and Guillain-Barre syndrome and the inflammatory sequelae of viral encephalitis, cerebral vascular injuries, head trauma, anxiety disorders, depression, stress, epilepsy, dementia, distonia, Alzheimer's disease, Huntingdon's disease, Tourette's syndrome, ischaemia, pain, Parkinson's disease, schizophrenia, substance abuse disorders especially relating to nicotine, alcohol, and opiates, smoking cessation, treatment of nicotine dependance and/or treatment of symptoms of nicotine withdrawal, gastrointestinal disorders (such as dysfunction of gastrointestinal motility or diarrhoea), obesity and other eating disorders associated with excessive food intake, and associated health complications including non-insulin dependant diabetes mellitus.

The present invention is particularly directed to psychosis, memory deficit, cognitive disorders, attention deficit disorder, migraine, anxiety disorders, stress, epilepsy, Parkinson's disease, schizophrenia, substance abuse disorders especially relating to nicotine, alcohol, and opiates, smoking cessation, treatment of nicotine dependance and/or treatment of symptoms of nicotine withdrawal, gastrointestinal disorders (such as dysfunction of gastrointestinal motility or diarrhoea), obesity and other eating disorders associated with excessive food intake, and associated health complications including non-insulin dependant diabetes mellitus.

The present invention is more particularly directed to disorders selected from psychosis, schizophrenia, cognitive disorders, attention deficit disorder, smoking cessation, gastrointestinal disorders (such as dysfunction of gastrointestinal motility or diarrhoea), obesity and other eating disorders associated with excessive food intake (including bulimia and compulsive eating disorder) and associated health complications including non-insulin dependant diabetes mellitus. The present invention is particularly directed to obesity and other eating disorders associated with excessive food intake and associated health complications including non-insulin dependant diabetes mellitus, and particularly to obesity and other eating disorders associated with excessive food intake, and especially to obesity.

In an alternative embodiment, the present invention is directed to substance abuse disorders especially relating to nicotine, alcohol, and opiates, smoking cessation, treatment of nicotine dependance and/or treatment of symptoms of nicotine withdrawal, and particularly to smoking cessation and the facilitation thereof.

In a further alternative embodiment, the present invention is directed to gastrointestinal disorders (such as dysfunction of gastrointestinal motility or diarrhoea).

In a further alternative embodiment, the present invention is directed to the treatment of Parkinson's Disease.

The present invention may be employed in respect of a human or animal subject, more preferably a mammal, more preferably a human subject.

As used herein, the term "treatment" as used herein includes prophylactic treatment.

As used herein, the term "prodrug" means any pharmaceutically acceptable prodrug of the compound of formula (I). For example, the compound of formula (I) may be prepared in a prodrug form wherein a free —OH group is derivatised (for example, via an ester, amide or phosphate bond) with a suitable group (the group may contain, for example, an alkyl, aryl, phosphate, sugar, amine, glycol, sulfonate or acid function) which is suitably labile so as it will be removed/cleaved (eg. by hydrolysis) to reveal the compound of formula (I) sometime after administration or when exposed to the desired biological environment.

As used herein, the term "pharmaceutically acceptable salt" means any pharmaceutically acceptable salt of the compound of formula (I). Salts may be prepared from pharmaceutically acceptable non-toxic acids and bases including inorganic and organic acids and bases. Such acids include acetic, benzenesulfonic, benzoic, camphorsulfonic, citric, ethenesulfonic, dichloroacetic, fumaric, gluconic, glutamic, hippuric, hydrobromic, hydrochloric, isethionic, lactic, maleic, malic, mandelic, methanesulfonic, mucic, nitric, pamoic, pantothenic, phosphoric, succinic, sulfuric, tartaric, oxalic, p-toluenesulfonic and the like. Particularly preferred are hydrochloric, hydrobromic, phosphoric, sulfuric and methanesulfonic acids, and most particularly preferred is the methanesulfonate salt. Acceptable base salts include alkali metal (e.g. sodium, potassium), alkaline earth metal (e.g. calcium, magnesium) and aluminium salts.

The compound of formula (I) may be used in combination with one or more additional drugs useful in the treatment of the disorders mentioned above, the components being in the same formulation or in separate formulations for administration simultaneously or sequentially.

Compounds of formula (I) may be prepared according to the reaction scheme (where P is a nitrogen protecting group). $R^1$, $R^2$, and $R^3$ are as previously described. The ether (IV) may be formed by reaction of the azetidinol (II) with a benzhydrol (III, X=OH) with removal of water (for example azeotropic removal of water under standard Dean-Stark conditions). The ether (IV) may also be formed by reaction of the azetidinol (II) with a benzhydryl group substituted with a suitable leaving-group (III, X=Cl, Br, I, mesylate, tosylate) and a strong base such as sodium hydride. Formation of the azetidine (V) may be achieved by reaction of (IV) with a suitable nitrogen deprotection agent. For example, if P is a benzhydryl group, then deprotection may be carried out by treatment with 1-chloroethyl chloroformate followed by treatment with methanol. The deprotected azetidine (V) can be isolated directly as the hydrochloride salt or, upon basification, as the free-base. The urea (I) can be formed by reaction of azetidine (V) with an N-alkyl isocyanate, or an N-alkyl carbamoyl chloride and a base such as triethylamine or potassium carbonate. Alternatively, the urea may be prepared directly from the protected azetidine (IV) without isolation of the intermediate azetidine (V). For example, when P is a benzhydryl group, azetidine (IV) may be treated with phosgene followed by an amine, $R^3NH_2$, to give urea (I) directly. Azetidine (V) may also be converted to the corresponding carbamoyl chloride (VI) by treatment with, for example, triphosgene. This intermediate carbamoyl chloride (VI) may be reacted with an amine, $R^3NH_2$, to give the urea (I).

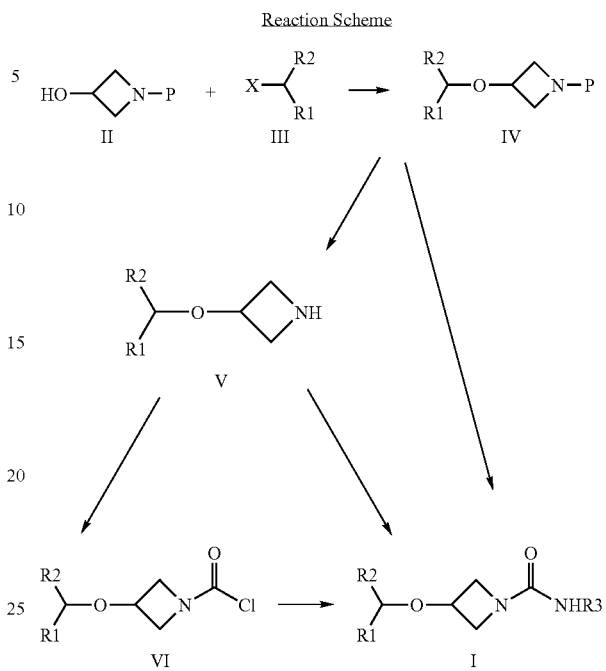

Reaction Scheme

The invention further provides a pharmaceutical composition comprising an effective amount of the compound of formula (I) in combination with a pharmaceutically acceptable carrier or excipient and a method of making such a composition comprising combining an effective amount of the compound of formula (I) with a pharmaceutically acceptable carrier or excipient.

To further increase efficacy, the composition may contain components such as dextrans or cyclodextrins or ether derivatives thereof, which aid stability and dispersion, and decrease metabolism of the active ingredient.

For compositions in which the pharmaceutically acceptable carrier comprises a cyclodextrin or an ether derivative thereof, the active ingredient is intimately mixed with an aqueous solution of the cyclodextrin or ether derivative thereof, with optional addition of further pharmaceutically acceptable ingredients before, during or after said mixing. The thus obtained solution is optionally lyophilized, and the lyophilized residue is optionally reconstituted with water.

In an embodiment of the present invention, the composition further comprises a buffer system, an isotonizing agent and water.

Compounds of formula (I) may be administered in a form suitable for oral use, for example a tablet, capsule, aqueous or oily solution, suspension or emulsion; for topical use including transmucosal and transdermal use, for example a cream, ointment, gel, aqueous or oil solution or suspension, salve, patch or plaster; for nasal use, for a example a snuff, nasal spray or nasal drops; for vaginal or rectal use, for example a suppository, for administration by inhalation, for example a finely divided powder or a liquid aerosol; for sub-lingual or buccal use, for example a tablet or capsule; or for parenteral use (including intravenous, subcutaneous, intramuscular, intravascular or infusion), for example a sterile aqueous or oil solution or suspension. In general the above compositions may be prepared in a conventional manner using conventional excipients, using standard techniques well known to those skilled in the art of pharmacy. Preferably, the compound is administered orally.

For oral administration, the compounds of formula (I) will generally be provided in the form of tablets or capsules or as an aqueous solution or suspension.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredient is mixed with water or an oil such as peanut oil, liquid paraffin or olive oil. Alternatively, the active ingredient may be mixed with excipients, surfactants or solubilising agents such as Labrafil®, Labrasol® or Miglyol®, or appropriate mixtures thereof.

For intramuscular, intraperitoneal, subcutaneous and intravenous use, the compounds of formula (I) will generally be provided in sterile aqueous solutions or suspensions, buffered to an appropriate pH and isotonicity. Suitable aqueous vehicles include Ringer's solution and isotonic sodium chloride. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

It will be appreciated that the dosage levels used may vary over quite a wide range depending upon the compound used, the severity of the symptoms exhibited by the patient and the patient's body weight.

The invention will now be described in detail with reference to the following pharmacological examples. It will be appreciated that the examples are intended to illustrate and not to limit the scope of the present invention.

Experimental

Assay Procedures

Binding to $CB_1$ Receptors

The binding of compounds of Formula I to recombinant human $CB_1$ receptors was determined in vitro by standard methods, with reference to the procedure described by Rinaldi-Carmona et al. (Rinaldi-Camona, M., Pialot, F., Congy, C., Redon, E., Barth, F., Bachy, A., Breliere, J. C., Soubre, P., LeFur, G., *Life Sci.* 1996, 58(15), 1239-1247). Membranes were prepared from HEK293 cells expressing recombinant $hCB_1$ receptors. Binding assays are performed in a total volume of 250 μL, containing [$^3$H]—SR-141716A (1 nM final concentration), membranes and test compound. Non-specific binding is determined using CP55,940 (10 μM). Serial dilutions are performed starting from test compounds as 10 mM solutions in DMSO. Compounds are tested over the concentration range $10^{-10}$ M to $10^{-5}$ M. $K_i$ values are calculated from $IC_{50}$ values using the Cheng-Prusoff equation.

The thus-determined activity of compounds of formula (I) is shown in Table 1.

TABLE 1

| Example | $K_i$ ($hCB_1$) nM |
|---------|---------------------|
| 1       | 4.7                 |
| 4       | 4.5                 |
| 28      | 80                  |
| 30      | 19                  |
| 81      | 2.3                 |
| 94      | 1.3                 |
| 139     | 0.6                 |
| 140     | 27                  |

Blockade of $\Delta^9$-THC Induced Hypolocomotion in Mice

The in vivo activity of compounds of formula (I) was assayed for ability to antagonise the reduction in locomotor behaviour induced by acute systemic administration of $\Delta^9$-THC in male C57B1/6 mice. The procedure was as follows.

Test compounds are assessed following acute oral or intraperitoneal administration at a dose of 30 mg/kg. Each study utilises a between-subjects design (typically n=8) and compares the effects of doses of the test agent to those of vehicle and a positive control.

The route of test compound administration, drug volume and injection-test-interval are dependent upon the compounds used. 10 min before testing, a 3 mg/kg dose $\Delta^9$-THC (or vehicle) is administered to mice by the i.p. route. Automated boxes (AM-1052 activity monitors, Benwick Electronics, Linton Instrumentation) are used to record photocell beam breaks as a measure of locomotor activity. The light beams are arranged on a 7 by 4 matrix on a metal grid. 16 grids are connected in series and Perspex boxes, 20 (width)×40 (length)×20 (height) cm, with a flat perforated, Perspex lid are placed in each grid. Mice are placed singly in Perspex boxes and the recording of activity in all 16 boxes starts simultaneously. The mice are left undisturbed to explore the novel activity monitor boxes for 15 minutes while beam breaks are recorded.

Locomotor activity data are subjected to one-way analysis of variance (ANOVA) with drug treatment as a between-subjects factor. A significant main effect is followed up by the performance of Dunnett's test in order to assess which treatment mean(s) are significantly different from the control mean. Significant differences between the vehicle/$\Delta^9$-THC group and Test compound/$\Delta^9$-THC groups are assessed by Newman-Keuls test. All statistical analyses were performed using Statistica Software, Version 6.0 (Statsoft Inc.) and Microsoft Excel 7.0 (Microsoft Corp.).

The thus-determined activity of compounds of formula (I) is shown in Table 2.

TABLE 2

| Example | Active dose (mg/kg), route |
|---------|-----------------------------|
| 1       | 30, p.o.                    |
| 4       | 30, p.o.                    |
| 81      | 30, p.o.                    |
| 94      | 30, p.o.                    |

Regulation of Feeding Behaviour

The in vivo activity of compounds of formula (I) was assayed for ability to regulate feeding behaviour by measuring food consumption in male food-deprived Lister-hooded rats as follows.

Test compounds are assessed following acute administration. Each study utilises a between-subjects design (typically n=8) and compares the effects of doses of the test agent to those of vehicle and a positive control.

The anorectic drug sibutramine, or the reference $CB_1$ receptor antagonist, SR141716A, normally serves as a positive control. The route of drug administration, drug volume and injection-test-interval are dependent upon the compounds used. The injection-test-interval is the time between dosing and food re-presentation. Typically, animals are fasted such that at the time of food re-presentation food has been withdrawn for an 18-hour period. Food consumption is assayed at pre-determined time points (typically 1, 2 and 4 hours after administration). Food intake data are subjected to one-way analysis of variance (ANOVA) with drug as a between-subjects factor. A significant main effect is followed up by the performance of Dunnett's test in order to assess which treatment mean(s) are significantly different from the control mean. All statistical analyses were performed using Statistica Software, Version 6.0 (Statsoft Inc.) and Microsoft Excel 7.0 (Microsoft Corp.).

The thus-determined activity of compounds of formula (I) is shown in Table 3.

TABLE 3

| Example | M.E.D (mg/kg), route |
|---------|----------------------|
| 1       | 30, p.o.             |
| 4       | 30, p.o.             |
| 81      | 3, p.o.              |
| 94      | 10, p.o.             |
| 139     | 1, p.o.              |

Analytical Chemistry Procedures

HPLC

LC (50/80) refers to elution of a sample through an XTERRA RP18 (50 mm×4.6 mm) 5 μm column under gradient conditions. The initial eluent comprises 50% Methanol (pump-A) and 50% of a 10 mM aqueous ammonium acetate solution containing 5% IPA (pump-B) at a flow rate of 2 mL/min. After 1 min, a gradient is run over 5 min to an end point of 80% pump-A and 20% pump-B, which is isocratically maintained for a further 3 min. UV peak detection is generally carried out at a wavelength of 220 nm.

LC (80/20) refers to elution of a sample through an XTERRA RP18 (50 mm×4.6 mm) 5 μm column under isochratic conditions. The eluent comprises 80% Methanol (pump-A) and 20% of a 10 mM aqueous ammonium acetate solution containing 5% IPA (pump-B) at a flow rate of 2 mL/min over a period of 10 minutes. UV peak detection is generally carried out at a wavelength of 220 nm.

LC (CHIRAL AD) refers to elution of a sample through a CHIRALPAK AD column (250 mm×4.6 mm) 10 μm column under isochratic conditions. The eluent typically comprises 90% n-hexane and 10% 2-propanol at flow rate of 1 mL/min over a period of 40 minutes. UV peak detection is generally carried out at a wavelength of 220 nm.

$^1$H NMR

Proton nmr spectra were recorded on a 400 MHz Bruker spectrometer. Solutions were typically prepared in either deuterochloroform ($CDCl_3$) or deuterated dimethylsulfoxide ($d^6$-DMSO) with chemical shifts reported in d with reference to tetramethylsilane (TMS) as an internal standard, and coupling constants reported in Hz.

MS

Mass Spectra were acquired via loop injection on a Waters ZQ Mass Detector equipped with an Electrospray source operated in Positive/Negative Ion switching mode and a cone voltage of 25V.

SYNTHETIC EXAMPLES

Preparation of 1-benzhydryl-3-azetidinol (1)

This material was prepared according the method of Anderson and Lok (*J. Org. Chem.*, 1972, 37, 3953—the disclosure of which is incorporated herein by reference), m.p. 111-112° C. (lit. m.p. 113° C.).

Preparation of 2,4,4'-trichlorobenzhydrol (2)

To a stirred solution of 2,4-dichlorobenzaldehyde (286 mmol) in diethyl ether (500 mL) was added 4-chlorophenylmagnesium bromide (1.0 M in diethyl ether, 286 mmol) dropwise at 0° C. over a period of 1 hour. The reaction was allowed to warm to ambient temperature, and stirred for 3 h. The reaction mixture was quenched with saturated ammonium chloride solution (500 mL) and extracted with diethyl ether (2×500 mL), the extracts were washed with water and brine, dried (MgSO4) and concentrated in vacuo. The residue was purified by trituration with iso-hexane (500 mL) to yield the product as a white solid (60.0 g, 73%).

NMR (400 MHz, $d^6$-DMSO) $\delta_H$ 5.95 (1H, d, J 4.5 Hz), 6.23 (1H, d, J 4.0 Hz), 7.31 (2H, m), 7.37 (2H, m), 7.47 (1H, dd, J 2.5, 8.5 Hz), 7.55 (1H, d, J 2.0 Hz), 7.66 (1H, d, J 8.5 Hz).

Preparation of 1-benzhydryl-3-(2,4,4'-trichlorobenzhydryloxy)azetidine (3)

A solution of 2,4,4'-trichlorobenzhydrol (2) (174 mmol), p-toluenesulfonic acid (174 mmol) and 1-benzhydryl-3-azetidinol (1) (87 mmol) in toluene (700 mL) was heated at reflux under Dean-Stark conditions for 30 minutes. The solution was cooled, washed with sodium hydrogen carbonate (saturated aqueous solution, 700 mL), dried (MgSO4) and concentrated in vacuo. The residue was purified by column chromatography [$SiO_2$; (10% ethyl acetate:isohexane)] to furnish the product as a yellow oil (22.0 g, 50%).

NMR (400 MHz, $d^6$-DMSO) $\delta_H$ 2.78 (1H, t, J 6.5 Hz), 2.84 (1H, t, J 6.5 Hz), 3.23 (1H, t, J 6.5 Hz), 3.31 (1H, t, J 6.5 Hz), 4.18 (1H, m), 4.39 (1H, s), 5.71 (1H, s), 7.15 (2H, m), 7.24 (4H, m), 7.32 (2H, m), 7.37 (6H, m), 7.47 (1H, m), 7.57 (2H, m).

Preparation of 3-(2,4,4'-trichlorobenzhydryloxy)azetidine (4)

To a stirred solution of 1-benzhydryl-3-(2,4,4'-trichlorobenzhydryloxy)azetidine (3) (39 mmol) in dichloromethane (400 mL) was added 1-chloroethylchloroformate (98 mmol) dropwise at 0° C. and the reaction mixture stirred at room temperature overnight. The reaction mixture was concentrated in vacuo, then dissolved in methanol (400 mL) and stirred at room temperature for 1 hour. The reaction mixture was concentrated in vacuo, then diluted with ethyl acetate (400 mL) and washed with sodium hydroxide (5N, 400 mL), dried (MgSO4) and concentrated in vacuo to furnish a yellow oil. The residue was purified by filtration through silica, eluting with dichloromethane, then [ethyl acetate:methanol:ammonium hydroxide (90:8:2)] to yield a yellow oil (8.0 g, 60%).

NMR (400 MHz, DMSO) $\delta_H$ 3.38 (4H, bd), 4.29 (1H, m), 5.68 (1H, s), 7.32 (2H, m), 7.40 (2H, m), 7.49 (2H, m), 7.50 (1H, m), 7.60 (2H, m).

Example 1

3-(2,4,4'-trichlorobenzhydryloxy)-N-(tert-butyl)azetidine-1-carboxamide (5)

To a stirred solution of 3-(2,4,4'-trichlorobenzhydryloxy) azetidine (4) (3 mmol) in dichloromethane (10 mL) was added tert-butyl isocyanate (3 mmol) and triethylamine (catalytic amount) and the reaction mixture was stirred at room temperature for 3 hours. The reaction mixture was eluted through a pre-wetted ($CH_2Cl_2$) SCX-2 (2 g) cartridge with dichloromethane to yield the desired product as a white foam (424 mg, 33%).

NMR (400 MHz, DMSO) $\delta_H$ 1.20 (9H, s), 3.54 (1H, dd, J 4.5, 8.5 Hz), 3.80 (1H, dd, J 6.5, 8.5 Hz), 4.29 (1H, m), 5.62 (1H, s), 7.34 (2H, m), 7.42 (2H, m), 7.50 (1H, m), 7.61 (1H, m), 7.64 (1H, s)

LC (50/80) 97.5%, 7.59 min

Found: C, 57.19; H, 5.30; N, 6.26, $C16H14Cl3NO$ requires: C, 57.09; H, 5.25; N, 6.34%

Example 2

3-(2,4,4'-trichlorobenzhydryloxy)-N-(1-hydroxy-2-methylpropan-2-yl)azetidine-1-carboxamide (6)

To a stirred solution of triphosgene (5.5 mmol) in dichloromethane (50 mL) at 0° C. was added a solution of 3-(2,4,4'-trichlorobenzhydryloxy)azetidine (4) (14.6 mmol) and pyridine (16.1 mmol) in dichloromethane (50 mL) over a period of 1 hour. Reaction mixture was warmed to room temperature and stirred for 1 hour. The mixture was purified by filtration through silica, eluting with dichloromethane to yield the carbamoyl chloride intermediate as a dark orange oil. A solution of 'carbamoyl chloride' (2.47 mmol), triethylamine (2.47 mmol) and 2-amino-2-methyl-1-propanol (4.94 mmol) in dichloromethane was stirred at room temperature overnight. The reaction mixture was washed with water, dried ($MgSO_4$) and purified by chromatography [$SiO_2$:(1:1 ethyl acetate:isohexane)] to furnish the product as a colourless oil (352 mg, 31%).

NMR (400 MHz, $d^6$-DMSO) $\delta_H$ 1.13 (6H, s), 3.56(1H, dd, J 4.5, 8.5 Hz), 3.80 (1H, dd, J 6.5, 8.5 Hz) 4.30 (1H, m), 4.89 (1H, t, J 6.0 Hz), 5.48 (1H, s), 5.73 (1H, s), 7.34 (2H, m), 7.42 (2H, m), 7.51 (1H, m), 7.61 (2H, m)

MS 457 [M+H]$^+$

LC (50/80) 99.4%, 6.80 min

Preparation of 2,4'-dichlorobenzhydrol (7)

To a stirred solution of 2,4'-dichlorobenzophenone (239 mmol) in methanol (400 mL) was added sodium borohydride (119 mmol) portionwise at 0° C. Reaction mixture was warmed to room temperature and stirred for 1 hour, then quenched with water and the methanol was removed under reduced pressure. The residue was diluted with dichloromethane (400 mL) and washed with water and brine, dried ($MgSO_4$) and concentrated in vacuo to yield the product as an orange oil (47.1 g, 78%).

NMR (400 MHz, $d^6$-DMSO) $\delta_H$ 5.99 (1H, d, J 4.5 Hz), 6.16 (1H, d, J 4.5 Hz), 7.35 (7H, m), 7.66 (1H, m).

Preparation of 1-benzhydryl-3-(2,4'-dichlorobenzhydryloxy)azetidine (8)

A solution of 2,4'-dichlorobenzhydrol (7) (178 mmol), p-toluenesulphonic acid (198 mmol) and 1-benzhydryl-3-azetidinol (1) (99 mmol) in toluene (500 mL) was heated at reflux in a Dean-Stark apparatus for 40 minutes. The solution was cooled, washed with sodium hydrogen carbonate (saturated aqueous solution, 700 mL), dried ($MgSO_4$) and concentrated in vacuo. The residue was purified by column chromatography [$SiO_2$; (10% ethyl acetate:isohexane)] to finish the product as a yellow oil (17.8 g, 38%).

NMR (400 MHz, $d^6$-DMSO) $\delta_H$ 2.78 (1H, t, J 6.5 Hz), 2.82 (1H, t, J 6.5 Hz), 3.24 (1H, t, J=5.5 Hz), 3.28 (1H, t, J 5.5 Hz), 4.17 (1H, m), 4.39 (1H, s), 5.74 (1H, s), 7.16 (2H, m), 7.25 (4H, m), 7.32 (3H, m), 7.37 (8H, m), 7.57 (1H, m).

Preparation of 3-(2,4'-dichlorobenzhydryloxy)azetidine hydrochloride (9)

To a stirred solution of 1-benzhydryl-3-(2,4'-dichlorobenzhydryloxy)azetidine (8) (38 mmol) in dichloromethane (400 mL) was added 1-chloroethylchloroformate (94 mmol) dropwise at 0° C. and the reaction mixture stirred at room temperature overnight. The reaction mixture was concentrated in vacuo, then dissolved in methanol (400 mL) and stirred at room temperature for 2 hours. The reaction mixture was reduced in vacuo and diluted with isohexane (20 mL), diisopropyl ether (200 mL) and methanol (30 mL). Upon stirring, a precipitate formed. Filtration afforded the desired product as a white solid (10.1 g, 77%).

NMR (400 MHz, $d^6$-DMSO) $\delta_H$ 3.86 (2H, br d), 4.02 (2H, br d), 4.43 (1H, quintet, J 6.0 Hz) 5.86 (1H, s), 7.37 (3H, m), 7.44 (4H, m), 7.61 (1H, m), 8.98 (2H, br d).

Example 3

3-(2,4'-dichlorobenzhydryloxy)-N-(ethyl propionate-2-yl)azetidine-1-carboxamide (10)

A solution of 3-(2,4'-dichlorobenzhydryloxy)azetidine hydrochloride (9) (0.58 mmol), ethyl 2-isocyanatopropionate (0.58 mmol) and MP-carbonate (3.10 mmol/g, 1.74 mmol) in dichloromethane (3 mL) was shaken at room temperature overnight. The reaction mixture was eluted through a pre-wetted ($CH_2Cl_2$) SCX-2 (2 g) cartridge with dichloromethane to yield the desired product as a colourless gum (72 mg, 28%).

NMR (400 MHz, $d^6$-DMSO) $\delta_H$ 1.16 (3H, t, J 7.0 Hz), 1.22 (3H, d, J 7.5 Hz), 3.60 (1H, m), 3.68 (1H, m), 3.87 (1H, m), 3.95 (1H, m), 4.05 (3H, m), 4.36 (1H, m), 5.78 (1H, s), 6.65 (1H, d, J 7.5 Hz), 7.36 (3H, m), 7.41 (4H, m), 7.61 (1H, m).

LC (80/20) 96.5%, 0.80 min

Example 4

3-(2,4'-dichlorobenzhydryloxy)-N-(tert-butyl)azetidine-1-carboxamide (11)

This material was prepared, from the corresponding commercially available isocyanate, according to the method for compound (10).

NMR (400 MHz, d$^6$-DMSO) δ$_H$ 1.21 (9H, s), 3.56 (1H, m), 3.63 (1H, m), 3.82 (1H, m), 3.89 (1H, m), 4.27 (1H, m), 5.62 (1H, s), 5.76 (1H, m), 7.42 (6H, m), 7.61 (1H, m)
LC (80/20) 99.5%, 6.84 min

Example 5

3-(2,4'-dichlorobenzhydryloxy)-N-(2-thiophen-2-yl ethyl)azetidine-1-carboxamide (12)

This material was prepared, from the corresponding commercially available isocyanate, according to the method for compound (10).
NMR (400 MHz, d$^6$-DMSO) δ$_H$ 2.87 (2H, t, J 7.0 Hz), 3.18 (2H, m), 3.57 (1H, m), 3.65 (1H, m), 3.83 (1H, m), 3.91 (1H, m), 4.35 (1H, m), 5.77 (1H, s), 6.47 (1H, t, J 5.5 Hz), δ 6.84 (1H, m), 6.94 (1H, m), 7.30 (1H, m), 7.36 (3H, m), 7.42 (4H, m), 7.60 (1H, m).
LC (80/20) 98.5%, 1.07 min

Example 6

3-(2,4'-dichlorobenzhydryloxy)-N-(ethyl 3-phenyl-propionate-2-yl)azetidine-1-carboxamide (13)

This material was prepared, from the corresponding commercially available isocyanate, according to the method for compound (10).
NMR (400 MHz, d$^6$-DMSO) δ$_H$ 2.91 (2H, m), 3.58 (2H, m), 3.87 (1H, m), 4.20 (1H, m), 4.33 (1H, m), 5.76 (1H, s), 6.72 (1H, d, J 8.0 Hz), 7.20 (3H, m), 7.26 (2H, m), 7.36 (3H, m), 7.42 (4H, m), 7.60 (1H, m).
LC (80/20) 99.2%, 1.14 min

Example 7

3-(2,4'-dichlorobenzhydryloxy)-N-[ethyl 4-(methylthio)butyrate-2-yl]azetidine-1-carboxamide (14)

This material was prepared, from the corresponding commercially available isocyanate, according to the method for compound (10).
NMR (400 MHz, d$^6$-DMSO) δ$_H$ 1.16 (3H, t, J 7.5 Hz), 1.87 (2H, m), 2.03 (3H, s), 2.46 (2H, m), 3.62 (1H, m), 3.70 (1H, m), 3.85-4.00 (2H, m), 4.06 (2H, m), 4.16 (1H, m), 4.37 (1H, m), 5.78 (1H, s), 6.64 (1H, m), 7.37 (3H, m), 7.47 (4H, m), 7.61 (1H, m).
LC (80/20) 99.3%, 0.99 min

Example 8

3-(2,4'-dichlorobenzhydryloxy)-N-(cyclopropylmethyl)azetidine-1-carboxamide (15)

3-(2,4'-dichlorobenzhydryloxy)azetidine hydrochloride (9) was converted to the corresponding free-base via standard methods.
To a stirred solution of triphosgene (6.6 mmol) in dichloromethane (50 mL) at 0° C. was added a solution of 'free-base' (17.4 mmol) and pyridine (19.2 mmol) in dichloromethane (50 mL) over a period of 1 hour. Reaction mixture was warmed to room temperature and stirred for 1 hour. The mixture was purified by filtration through silica, eluting with dichloromethane to yield a the carbamoyl chloride as a dark orange oil (5.32 g, 83%) which was used immediately.
A solution of 'carbamoyl chloride' (0.54 mmol), MP-carbonate (3.10 mmol/g, 1.62 mmol) and (aminomethyl)cyclopropane (0.81 mmol) in dichloromethane was shaken at room temperature overnight. The reaction mixture was eluted through a pre-wetted (CH$_2$Cl$_2$) SCX-2 (2 g) cartridge with dichloromethane to yield a colourless gum (51 mg, 22%).
MS 406 [M+H]$^+$
LC (80/20) 98.9%, 0.91 min

Example 9

3-(2,4'-dichlorobenzhydryloxy)-N-(2,3-dihydrobenzofuran-5-yl-methyl)azetidine-1-carboxamide (16)

This material was prepared, from the corresponding commercially available amine, according to the method for compound (15).
MS 484 [M+H]$^+$
LC (80/20) 89.9%, 1.06 min

Example 10

3-(2,4'-dichlorobenzhydryloxy)-N-(2,5-dimethylfuran-3-yl-methyl)azetidine-1-carboxamide (17)

This material was prepared, from the corresponding commercially available amine, according to the method for compound (15).
MS 460 [M+H]$^+$
LC (80/20) 91.6%, 1.17 min

Example 11

3-(2,4'-dichlorobenzhydryloxy)-N-(2,3-dihydro-benzo[1,4]dioxin-2-yl-methyl)azetidine-1-carboxamide (18)

This material was prepared, from the corresponding commercially available amine, according to the method for compound (15).
MS 500 [M+H]$^+$
LC (80/20) 94.5%, 1.34 min

Example 12

3-(2,4'-dichlorobenzhydryloxy)-N-(5-methyl-isoxazol-3-yl-methyl)azetidine-1-carboxamide (19)

This material was prepared, from the corresponding commercially available amine, according to the method for compound (15).
MS 447 [M+H]$^+$
LC (80/20) 97.0%, 0.75 min

Example 13

3-(2,4'-dichlorobenzhydryloxy)-N-[(R)-sec-butyl]azetidine-1-carboxamide (20)

This material was prepared, from the corresponding commercially available amine, according to the method for compound (15).
MS 408 [M+H]$^+$
LC (80/20) 96.7%, 0.96 min

Example 14

3-(2,4'-dichlorobenzhydryloxy)-N-(2-bromothiophen-3-yl-methyl)azetidine-1-carboxamide (21)

This material was prepared, from the corresponding commercially available amine, according to the method for compound (15).
MS 527 [M+H]$^+$
LC (80/20) 90.0%, 1.38 min

Example 15

3-(2,4'-dichlorobenzhydryloxy)-N-[(S)-sec-butyl]azetidine-1-carboxamide (22)

This material was prepared, from the corresponding commercially available amine, according to the method for compound (15).
MS 408 [M+H]$^+$
LC (80/20) 97.5%, 0.96 min

Example 16

3-(2,4'-dichlorobenzhydryloxy)-N-(thiophen-3-yl-methyl)azetidine-1-carboxamide (23)

This material was prepared, from the corresponding commercially available amine, according to the method for compound (15).
MS 448 [M+H]$^+$, 446
LC (80/20) 98.2%, 1.002 min

Example 17

3-(2,4'-dichlorobenzhydryloxy)-N-(2-methoxyphenylmethyl)azetidine-1-carboxamide (24)

This material was prepared, from the corresponding commercially available amine, according to the method for compound (15).
MS 472 [M+H]$^+$
LC (80/20) 97.2%, 1.11 min

Example 18

3-(2,4'-dichlorobenzhydryloxy)-N-(2-furanylmethyl)azetidine-1-carboxamide (25)

This material was prepared, from the corresponding commercially available amine, according to the method for compound (15).
MS 432 [M+H]$^+$
LC (80/20) 97.0%, 0.88 min

Example 19

3-(2,4'-dichlorobenzhydryloxy)-N-(3-ethoxypropyl)azetidine-1-carboxamide (26)

This material was prepared, from the corresponding commercially available amine, according to the method for compound (15).
MS 438 [M+H]$^+$
LC (80/20) 99.5%, 0.847 min

Example 20

3-(2,4'-dichlorobenzhydryloxy)-N-(2-tetrahydrofuranylmethyl)-azetidine-1-carboxamide (27)

This material was prepared, from the corresponding commercially available amine, according to the method for compound (15).
MS 436 [M+H]$^+$
LC (80/20) 99.3%, 0.78 min

Example 21

3-(2,4'-dichlorobenzhydryloxy)-N-[3-(2-oxopyrrolidinyl)propyl]azetidine-1-carboxamide (28)

This material was prepared, from the corresponding commercially available amine, according to the method for compound (15).
MS 477 [M+H]$^+$
LC (80/20) 97.7%, 0.68 min

Example 22

3-(2,4'-dichlorobenzhydryloxy)-N-(exo-2-norbornanyl)azetidine-1-carboxamide (29)

This material was prepared, from the corresponding commercially available amine, according to the method for compound (15).
MS 446 [M+H]$^+$
LC (80/20) 97.9%, 1.38 min

Example 23

3-(2,4'-dichlorobenzhydryloxy)-N-(1-phenylpropyl)azetidine-1-carboxamide (30)

This material was prepared, from the corresponding commercially available amine, according to the method for compound (15).
MS 470 [M+H]$^+$
LC (80/20) 89.7%, 1.33 min

Example 24

3-(2,4'-dichlorobenzhydryloxy)-N-[(R)-α-methylbenzyl]azetidine-1-carboxamide (31)

This material was prepared, from the corresponding commercially available amine, according to the method for compound (15).
MS 456 [M+H]$^+$
LC (80/20) 92.5%, 1.19 min

Example 25

3-(2,4'-dichlorobenzhydryloxy)-N-[(R)-1-(3-methoxyphenyl)ethyl]-azetidine-1-carboxamide (32)

This material was prepared, from the corresponding commercially available amine, according to the method for compound (15).

MS 486 [M+H]+
LC (80/20) 93.6%, 1.17 min

Example 26

3-(2,4'-dichlorobenzhydryloxy)-N-(dimethylaminoethyl)azetidine-1-carboxamide (33)

This material was prepared, from the corresponding commercially available amine, according to the method for compound (15).
MS 423 [M+H]+
LC (80/20) 96.8%, 0.71 min Example 27

3-(2,4'-dichlorobenzhydryloxy)-N-[(S)-1-(3-methoxyphenyl)ethyl]-azetidine-1-carboxamide (34)

This material was prepared, from the corresponding commercially available amine, according to the method for compound (15).
LC (80/20) 96.8%, 1.18 min MS 486 [M+H]+

Preparation of 1-benzhydryl-3-(4,4'-dichlorobenzhydryloxy)azetidine (35)

This material was prepared from 1-benzhydryl-3-azetidinol (1) (45.0 mmol) and 4,4'-dichlorobenzhydrol (90.0 mmol) using the procedure described for compound (3) (8.6 g, 40%).
NMR (400 MHz, d$^6$-DMSO)$\delta_H$ 2.80 (2H, m), 3.25 (2H, m), 4.13 (1H, t, J 6.0 Hz), 4.39 (1H, s), 5.50 (1H, s), 7.15 (2H, m), 7.25 (4H, m), 7.31-7.40 (12H, m).
LC (50/80) 99.7%, 3.18 min Preparation of 3-(4,4'-dichlorobenzhydryloxy)azetidine (36)

To a stirred solution of 1-benzhydryl-3-(4,4'-dichlorobenzhydryloxy)azetidine (35) (8.4 mmol) in dichloromethane (50 mL) was added 1-chloroethylchloroformate (16.9 mmol) dropwise at 0° C. and the reaction mixture was stirred at reflux for 6 hours. The reaction mixture was cooled to room temperature, concentrated in vacuo, then dissolved in methanol (50 mL) and stirred at room temperature for overnight. The reaction mixture was reduced in vacuo and triturated with diethyl ether (100 mL) to afford the desired product as a white solid (2.16 g, 74%).
NMR (400 MHz, d$^6$-DMSO) $\delta_H$ 3.84 (2H, m), 3.99 (2H, m), 4.39(1H, quintet, J 6.5 Hz), 5.65 (1H, s), 7.37 (4H, m), 7.44 (4H, m).
LC (50/80) 98.8%, 4.32 min Example 28

3-(4,4'-dichlorobenzhydryloxy)-N-(tert-butyl)azetidine-1-carboxamide (37)

This material was prepared from 3-(4,4'-dichlorobenzhydryloxy)azetidine (36) and the corresponding commercially available isocyanate, using the procedure described for compound (5) (53.0 mg, 45%).

NMR (400 MHz, d$^6$-DMSO) $\delta_H$ 1.20 (9H, s), 3.58 (2H, m), 3.83 (2H, m), 4.24 (1H, m), 5.61 (1H, s), 7.39 (8H, m).
LC (50/80) 99.0%, 6.84

Example 29

3-(4,4'-dichlorobenzhydryloxy)-N-(n-hexyl)azetidine-1-carboxamide (38)

This material was prepared from 3-(4,4'-dichlorobenzhydryloxy)azetidine (36) and the corresponding commercially available isocyanate, using the procedure described for compound (5).
NMR (400 MHz, d$^6$-DMSO) $\delta_H$ 0.847 (3H, t, J 7.0 Hz), 1.20-1.37 (8H, br m), 2.93 2H, q, J 6.5 Hz), 3.56 (2H, m), 3.83 (2H, m), 4.28 (1H, m), 5.55 (1H, s), 6.28 (1H, t, J=5.5 Hz), 7.39 (8H, m).
LC (50/80) 97.6%, 8.21 min.

Example 30

3-(4,4'-dichlorobenzhydryloxy)-N-(1-adamantyl)azetidine-1-carboxamide (39)

This material was prepared from 3-(4,4'-dichlorobenzhydryloxy)azetidine (36) and the corresponding commercially available isocyanate, using the procedure described for compound (5).
NMR (400 MHz, d$^6$-DMSO) $\delta_H$ 1.58 (6H, br m), 1.86 (6H, m), 1.97 (3H, br s), 3.57 (2H, m), 3.83 (2H, m), 4.23 (1H, m), 5.53 (1H, s), 7.33-7.42 (8H, m)
LC (50/80) 98.0%, 8.95 min Example 31

3-(4,4'-dichlorobenzhydryloxy)-N-(cyclohexyl)azetidine-1-carboxamide (40)

This material was prepared from 3-(4,4'-dichlorobenzhydryloxy)azetidine (36) and the corresponding commercially available isocyanate, using the procedure described for compound (5).
NMR (400 MHz, d$^6$-DMSO) $\delta_H$ 0.97-1.26 (5H, br m), 1.49-1.72 (5H, br m), 3.57 (2H, m), 3.83 (2H, m), 4.27 (1H s), 6.05 (1H, m), 6.34-7.45 (8H, m)
LC (50/80) 97.2%, 7.67 min Example 32

3-(4,4'-dichlorobenzhydryloxy)-N-(3-methylbenzyl)azetidine-1-carboxamide (41)

This material was prepared from 3-(4,4'-dichlorobenzhydryloxy)azetidine (36) and the corresponding commercially available isocyanate, using the procedure described for compound (5).
NMR (400 MHz, DMSO) $\delta_H$ 2.26 (2H, s), 3.63 (1H, m), 3.89 (1H, m), 4.12 (1H, m), 4.30 (1H, m), 5.76 (1H, s), 7.01 (2H, m), 7.17 (1H, m), 7.38 (5H, m)
LC (50/80) 87.8%, 7.73 min

Example 33

3-(4,4'-dichlorobenzhydryloxy)-N-(4-methylbenzyl)azetidine-1-carboxamide (42)

This material was prepared from 3-(4,4'-dichlorobenzhydryloxy)azetidine (36) and the corresponding commercially available isocyanate, using the procedure described for compound (5)

NMR (400 MHz, d$^6$-DMSO) δ$_H$ 2.26 (3H, s), 3.63 (2H, m), 3.89 (2H, m), 4.11 (2H, m), 4.30 (1H, m), 5.76 (1H, s), 6.85 (1H, m), 7.10 (4H, m), 7.39 (8H, m)

LC (50/80) 94.4%, 7.77 min

Example 34

3-(4,4'-dichlorobenzhydryloxy)-N-(2,4-dichlorobenzyl)azetidine-1-carboxamide (43)

This material was prepared from 3-(4,4'-dichlorobenzhydryloxy)azetidine (36) and the corresponding commercially available isocyanate, using the procedure described for compound (5).

NMR (400 MHz, d$^6$-DMSO) δ$_H$ 3.67 (2H, m), 3.94 (2H, m), 4.19 (2H, m), 4.33 (1H, m), 5.58 (1H, s), 6.97 (1H, t, J, 6.0 Hz), 7.30 (1H, m), 7.36-7.45 (9H, m), 7.57 (1H, m)

LC (50/80) 97.0%, 8.83 min

Example 35

3-(4,4'-dichlorobenzhydryloxy)-N-(phenethyl)azetidine-1-carboxamide (44)

This material was prepared from 3-(4,4'-dichlorobenzhydryloxy)azetidine (36) and the corresponding commercially available isocyanate, using the procedure described for compound (5).

NMR (400 MHz, d$^6$-DMSO) δ$_H$ 2.66 (2H, t, J 7.5 Hz), 3.15 (2H, m), 3.58 (2H, m), 3.84 (2H, m), 4.29 (1H, m), 5.55 (1H, s), 6.42 (1H, t, J 5.5 Hz), 7.18 (3H, m), 7.27 (2H, m), 7.35-7.44 (8H, m)

LC (50/80) 90.2%, 7.56 min

Example 36

3-(4,4'-dichlorobenzhydryloxy)-N-(4-fluorobenzyl)azetidine-1-carboxamide (45)

This material was prepared from 3-(4,4'-dichlorobenzhydryloxy)azetidine (36) and the corresponding commercially available isocyanate, using the procedure described for compound (5).

NMR (400 MHz, d$^6$-DMSO) δ$_H$ 3.64 (2H, m), 3.89 (2H, m), 4.14 (2H, m), 4.31 (1H, m), 5.56 (1H, s), 6.91 (1H, t, J 6.0 Hz), 7.11 (2H, m), 7.25 (2H, m), 7.35-7.44 (8H, m)

LC (50/80) 96.9%, 7.48 min

Example 37

3-(4,4'-dichlorobenzhydryloxy)-N-[(S)-α-methylbenzyl]azetidine-1-carboxamide (46)

This material was prepared from 3-(4,4'-dichlorobenzhydryloxy)azetidine (36) and the corresponding commercially available isocyanate, using the procedure described for compound (5).

NMR (400 MHz, d$^6$-DMSO) δ$_H$ 1.30 (3H, d, J 7.5 Hz), 3.63 (2H, m), 3.89 (2H, m), 4.30 (1H, m), 4.75 (1H, m), 5.55 (1H, s), 6.71 (1H, d, J 8.0 Hz), 7.18 (1H, m), 7.27 (4H, m), 7.39 (8H, m)

LC (50/80) 95.3%, 7.48 min

Example 38

3-(4,4'-dichlorobenzhydryloxy)-N-(4-methoxybenzyl)azetidine-1-carboxamide (47)

This material was prepared from 3-(4,4'-dichlorobenzhydryloxy)azetidine (36) and the corresponding commercially available isocyanate, using the procedure described for compound (5).

NMR (400 MHz, d$^6$-DMSO) δ$_H$ 3.61 (2H, m), 3.71 (3H, s), 3.88 (2H, m), 4.08 (2H, m), 4.30 (1H, m), 5.56 (1H, s), 6.84 (3H, m), 7.14 (2H, m), 7.35-7.44 (8H, m)

LC (50/80) 94.9%, 7.30 min

Example 39

3-(4,4'-dichlorobenzhydryloxy)-N-[(R)-α-methylbenzyl]azetidine-1-carboxamide (48)

This material was prepared from 3-(4,4'-dichlorobenzhydryloxy)azetidine (36) and the corresponding commercially available isocyanate, using the procedure described for compound (5).

NMR (400 MHz, d$^6$-DMSO) δ$_H$ 1.31 (3H, d, J 7.0 Hz), 3.62 (2H, m), 3.89 (2H, m), 4.30 (1H, m), 4.73 (1H, m), 5.55 (1H, s), 6.66 (1H, d, J 8.0 Hz), 7.18 (1H, m), 7.28 (4H, m), 7.39 (8H, m)

LC (80/20) 96.8%, 1.25 min

Example 40

3-(4,4'-dichlorobenzhydryloxy)-N-(cyclopropylmethyl)azetidine-1-carboxamide (49)

This material was prepared from 3-(4,4'-Dichlorobenzhydryloxy)azetidine (36) and the corresponding commercially available amine using the procedure described for compound (15) (11.0 mg, 10%).

NMR (400 MHz, d$^6$-DMSO) δ$_6$ 0.10 (2H, m), 0.33 (2H, m), 0.85 (1H, m), 2.82 (2H, d, J=6.0 Hz), 3.59 (2H, m), 3.85 (2H, m), 4.29 (1H, m), 5.55 (1H, s), 6.38 (1H, t, J 6.0 Hz), 6.39 (7H, m)

LC (50/80) 99.5%, 6.83 min

Example 41

3-(4,4'-dichlorobenzhydryloxy)-N-(benzhydryl)azetidine-1-carboxamide (50)

This material was prepared from 3-(4,4'-Dichlorobenzhydryloxy)azetidine (36) and the corresponding commercially available amine using the procedure described for compound (15).

NMR (400 MHz, d$^6$-DMSO) δ$_H$ 3.67 (2H, m), 3.95 (2H, m), 4.31 (1H, m), 5.56 (1H, m), 5.95 (1H, d, J 9.0 Hz), 7.19-7.43 (20H, m)

LC (50/80) 96.5%, 8.61 min

Example 42

3-(4,4'-dichlorobenzhydryloxy)-N-(furanylmethyl) azetidine-1-carboxamide (51)

This material was prepared from 3-(4,4'-Dichlorobenzhydryloxy)azetidine (36) and the corresponding commercially available amine using the procedure described for compound (15).
MS 432 [M+H]$^+$
LC (50/80) 96.6%, 6.70 min

Example 43

3-(4,4'-dichlorobenzhydryloxy)-N-(2-exo-norbornanyl)azetidine-1-carboxamide (52)

This material was prepared from 3-(4,4'-Dichlorobenzhydryloxy)azetidine (36) and the corresponding commercially available amine using the procedure described for compound (15).
MS 446 [M+H]$^+$
LC (50/80) 98.2%, 7.77 min

Example 44

3-(4,4'-dichlorobenzhydryloxy)-N-(cyclohexylmethyl)azetidine-1-carboxamide (53)

This material was prepared from 3-(4,4'-Dichlorobenzhydryloxy)azetidine (36) and the corresponding commercially available amine using the procedure described for compound (15).
MS 448 [M+H]$^+$
LC (50/80) 96.2%, 8.02 min

Example 45

3-(4,4'-dichlorobenzhydryloxy)-N-(thiophen-2-yl-methyl)azetidine-1-carboxamide (54)

This material was prepared from 3-(4,4'-Dichlorobenzhydryloxy)azetidine (36) and the corresponding commercially available amine using the procedure described for compound (15).
MS 448 [M+H]$^+$
LC (50/80) 95.9%, 7.12 min

Example 46

3-(4,4'-dichlorobenzhydryloxy)-N-(6-Fluoro-4H-benzo[1,3]dioxin-8-yl-methyl)azetidine-1-carboxamide (55)

This material was prepared from 3-(4,4'-Dichlorobenzhydryloxy)azetidine (36) and the corresponding commercially available amine using the procedure described for compound (15).
MS 518 [M+H]$^+$
LC (50/80) 98.4%, 7.43 min

Example 47

3-(4,4'-dichlorobenzhydryloxy)-N-(2,3-dihydrobenzofuran-5-yl-methyl)azetidine-1-carboxamide (56)

This material was prepared from 3-(4,4'-Dichlorobenzhydryloxy)azetidine (36) and the corresponding commercially available amine using the procedure described for compound (15).
MS 484 [M+H]$^+$
LC (50/80) 95.2%, 7.30 min

Example 48

3-(4,4'-dichlorobenzhydryloxy)-N-(furanylmethyl) azetidine-1-carboxamide (57)

This material was prepared from 3-(4,4'-Dichlorobenzhydryloxy)azetidine (36) and the corresponding commercially available amine using the procedure described for compound (15).
MS 432 [M+H]$^+$
LC (50/80) 97.1%, 6.70 min

Example 49

3-(4,4'-dichlorobenzhydryloxy)-N-(benzo[1,3]dioxol-5-yl-methyl)azetidine-1-carboxamide (58)

This material was prepared from 3-(4,4'-Dichlorobenzhydryloxy)azetidine (36) and the corresponding commercially available amine using the procedure described for compound (15).
MS 486 [M+H]$^+$
LC (50/80) 92.1%, 7.41 min

Example 50

3-(4,4'-dichlorobenzhydryloxy)-N-(2,3-dihydrobenzo[1,4]dioxin-2-yl-methyl)azetidine-1-carboxamide (59)

This material was prepared from 3-(4,4'-Dichlorobenzhydryloxy)azetidine (36) and the corresponding commercially available amine using the procedure described for compound (15).
MS 500 [M+H]$^+$
LC (50/80) 95.8%, 7.82 min

Example 51

3-(4,4'-dichlorobenzhydryloxy)-N-(2-thiophen-2-yl-thiazol-4-yl-methyl)azetidine-1-carboxamide (60)

This material was prepared from 3-(4,4'-Dichlorobenzhydryloxy)azetidine (36) and the corresponding commercially available amine using the procedure described for compound (15).
MS 531 [M+H]$^+$
LC (50/80) 92.8%, 7.68 min

Example 52

3-(4,4'-dichlorobenzhydryloxy)-N-(benzo[b]
thiophen-3-yl-methyl)azetidine-1-carboxamide (61)

This material was prepared from 3-(4,4'-Dichlorobenzhydryloxy)azetidine (36) and the corresponding commercially available amine using the procedure described for compound (15).
MS 498 [M+H]$^+$
LC (50/80) 98.1%, 8.26 min

Example 53

3-(4,4'-dichlorobenzhydryloxy)-N-(thiophen-3-yl-methyl)azetidine-1-carboxamide (62)

This material was prepared from 3-(4,4'-Dichlorobenzhydryloxy)azetidine (36) and the corresponding commercially available amine using the procedure described for compound (15).
MS 448 [M+H]$^+$
LC (50/80) 97.9%, 7.22 min

Example 54

3-(4,4'-dichlorobenzhydryloxy)-N-(5-methylisoxazol-3-yl-methyl)azetidine-1-carboxamide (63)

This material was prepared from 3-(4,4'-Dichlorobenzhydryloxy)azetidine (36) and the corresponding commercially available amine using the procedure described for compound (15).
MS 447 [M+H]$^+$
LC (50/80) 89.7%, 6.38 min

Example 55

3-(4,4'-dichlorobenzhydryloxy)-N-(benzo[b]
thiophen-2-yl-methyl)azetidine-1-carboxamide (64)

This material was prepared from 3-(4,4'-Dichlorobenzhydryloxy)azetidine (36) and the corresponding commercially available amine using the procedure described for compound (15).
MS 498 [M+H]$^+$
LC (50/80) 95.6%, 8.23 min

Example 56

3-(4,4'-dichlorobenzhydryloxy)-N-(2-adamantyl)
azetidine-1-carboxamide (65)

This material was prepared from 3-(4,4'-Dichlorobenzhydryloxy)azetidine (36) and the corresponding commercially available amine using the procedure described for compound (15).
NMR (400 MHz, d$^6$-DMSO) $\delta_H$ 1.43 (2H, m), 1.65-1.80 (8H, m), 1.94 (2H, m), 3.65 (2H, m), 3.92 (2H, m), 4.27 (1H, m), 5.77 (1H, d, J 6.5 Hz), 7.35-7.43 (6H, m)
LC (50/80) 97.0%, 8.99 min Preparation of 2,2'-dichlorobenzhydrol (66)

This material was prepared from 2,2'-dichlorobenzophenone using the procedure described for compound (7) (8.96 g, 89%).
NMR (400 MHz, d$^6$-DMSO) $\delta_H$ 6.09 (1H, d, J 5.5 Hz), 6.62 (1H, d, J 5.0 Hz), 7.27-7.44 (8H, m)
LC (50/80) 99.0%, 4.08 min Preparation of 1-benzhydryl-3-(2,2'-dichlorobenzhydryloxy)azetidine (67)

This material was prepared from 1-benzhydryl-3-azetidinol (1) (13.5 mmol) and 4,4'-dichlorobenzhydrol (27.0 mmol) using the procedure described for compound (3.

Preparation of
3-(2,2'-dichlorobenzhydryloxy)azetidine
hydrochloride (68)

This material was prepared from compound (67) (12.7 mmol) using the procedure described for compound (9) (1.58 g, 48%).
NMR (400 MHz, d$^6$-DMSO) $\delta_H$ 3.84-3.94 (2H, br m), 4.05-4.15 (2H, br m), 4.49 (1H, q, J 6.0 Hz), 6.10 (1H, s), 7.32-7.44 (7H, m), 7.50 (2H, m), 9.12 (1H, br s)

Example 57

3-(2,2'-dichlorobenzhydryloxy)-N-(tert-butyl)azetidine-1-carboxamide (69)

A solution of 3-(2,2'-dichlorobenzhydryloxy)azetidine hydrochloride (68) (0.29 mmol), tert-butyl isocyanate (0.29 mmol) and triethylamine (0.58 mmol) in dichloromethane (3 mL) was shaken at room temperature overnight, quenched with water, filtered through a PTFE phase separator cartridge and reduced in vacuo to yield a colourless gum (52 mg, 44%).
NMR (400 MHz, d$^6$-DMSO) $\delta_H$ 1.20 (9H, s), 3.65 (2H, m), 3.92 (2H, m), 4.31 (1H, m), 5.43 (1H, s), 7.38 (6H, m), 7.48 (2H, m)
LC (50/80) 98.8%, 6.53 min

Example 58

3-(2,2'-dichlorobenzhydryloxy)-N-(iso-propyl)azetidine-1-carboxamide (70)

This material was prepared from 3-(2,2'-dichlorobenzhydryloxy)azetidine hydrochloride (68) and the corresponding commercially available isocyanate using the procedure described for compound (69).
NMR (400 MHz, d$^6$-DMSO) $\delta_H$ 1.00 (2H, d, J 6.5 Hz), 3.65 (3H, m), 3.92 (2H, m), 4.34 (1H, m), 6.03 (2H, m), 7.38 (6H, m), 7.48 (2H, m)
LC (50/80) 98.9%, 5.76 min

Example 59

3-(2,2'-dichlorobenzhydryloxy)-N-(sec-butyl)azetidine-1-carboxamide (71)

This material was prepared from 3-(2,2'-dichlorobenzhydryloxy)azetidine hydrochloride (68) and the corresponding commercially available isocyanate using the procedure described for compound (69).
NMR (400 MHz, d$^6$-DMSO) $\delta_H$ 3.45 (1H, q, J 7.0 Hz), 3.65 (2H, m), 3.93 (2H, m), 4.35 (1H, m), 5.98 (2H, d, J 8.0 Hz), 6.06 (1H, s), 7.38 (6H, m), 7.47 (2H, m)
LC (50/80) 97.9%, 6.24 min

Example 60

3-(2,2'-dichlorobenzhydryloxy)-N-(n-propyl)azetidine-1-carboxamide (72)

This material was prepared from 3-(2,2'-dichlorobenzhydryloxy)azetidine hydrochloride (68) and the corresponding commercially available isocyanate using the procedure described for compound (69).

NMR (400 MHz, d$^6$-DMSO) $\delta_H$ 0.79 (2H, t, J 7.5 Hz), 1.38 (2H, q, J 7.0 Hz), 2.90 (2H, m), 3.65 (2H, m), 3.93 (2H, m), 4.36 (1H, m), 6.06 (1H, s), 6.28 (1H, m), 7.38 (6H, m), 7.47 (2H, m)

LC (50/80) 99.4%, 5.82 min

Example 61

3-(2,2'-dichlorobenzhydryloxy)-N-(allyl)azetidine-1-carboxamide (73)

This material was prepared from 3-(2,2'-dichlorobenzhydryloxy)azetidine hydrochloride (68) and the corresponding commercially available isocyanate using the procedure described for compound (69).

NMR (400 MHz, d$^6$-DMSO) $\delta_H$ 3.58 (2H, m), 3.68 (2H, m), 3.96 (2H, m), 4.37 (1H, m), 5.02 (2H, m), 5.76 (1H, m), 6.07 (1H, m), 6.49 (1H, t, J 5.5 Hz), 7.38 (6H, m), 7.49 (2H, m)

LC (50/80) 95.9%, 5.59 min

Example 62

3-(2,2'-dichlorobenzhydryloxy)-N-(n-butyl)azetidine-1-carboxamide (74)

This material was prepared from 3-(2,2'-dichlorobenzhydryloxy)azetidine hydrochloride (68) and the corresponding commercially available isocyanate using the procedure described for compound (69).

NMR (400 MHz, d$^6$-DMSO) $\delta_H$ 0.85 (3H, t, J 7.5 Hz), 1.23 (2H, m), 1.31 (2H, m), 2.93 (1H, q, J 7.0 Hz), 3.66 (2H, m), 3.92 (2H, m), 4.35 (1H, m), 6.05 (1H, s), 6.24 (1H, t, J 5.5 Hz), 7.38 (6H, m), 7.47 (2H, m)

LC (50/80) 98.6%, 6.53 min

Example 63

3-(2,2'-dichlorobenzhydryloxy)-N-(cyclopentyl)azetidine-1-carboxamide (75)

This material was prepared from 3-(2,2'-dichlorobenzhydryloxy)azetidine hydrochloride (68) and the corresponding commercially available isocyanate using the procedure described for compound (69).

NMR (400 MHz, d$^6$-DMSO) $\delta_H$ 1.31 (2H, m), 1.44 (2H, m), 1.61 (2H, m), 1.73 (2H, m), 3.65 (2H, m), 3.80 (1H, m), 3.93 (2H, m), 4.35 (1H, m), 6.06 (1H, s), 6.11 (1H, m), 7.38 (6H, m), 7.48 (2H, m)

LC (50/80) 99.7%, 6.60 min

Example 64

3-(2,2'-dichlorobenzhydryloxy)-N-(cyclohexyl)azetidine-1-carboxamide (76)

This material was prepared from 3-(2,2'-dichlorobenzhydryloxy)azetidine hydrochloride (68) and the corresponding commercially available isocyanate using the procedure described for compound (69).

NMR (400 MHz, d$^6$-DMSO) $\delta_H$ 1.12 (5H, m), 1.60 (5H, m), 3.64 (2H, m), 3.92 (2H, m), 4.32 (1H, m), 6.05 (2H, m), 7.37 (6H, m), 7.46 (2H, m)

LC (50/80) 98.7%, 7.06

Example 65

3-(2,2'-dichlorobenzhydryloxy)-N-(phenethyl)azetidine-1-carboxamide (77)

This material was prepared from 3-(2,2'-dichlorobenzhydryloxy)azetidine hydrochloride (68) and the corresponding commercially available isocyanate using the procedure described for compound (69).

NMR (400 MHz, d$^6$-DMSO) $\delta_H$ 2.70 (2H, t, J 7.5 Hz), 3.15 (2H, m), 3.65 (2H, m), 3.93 (2H, m), 4.36 (1H, m), 6.06 (1H, s), 6.40 (1H, t, J 5.5 Hz), 7.17 (3H, m), 7.26 (2H, m), 7.38 (6H, m), 7.48 (2H, m)

LC (50/80) 98.7%, 7.00 min

Example 66

3-(2,2'-dichlorobenzhydryloxy)-N-(1-adamantyl)azetidine-1-carboxamide (78)

This material was prepared from 3-(2,2'-dichlorobenzhydryloxy)azetidine hydrochloride (68) and the corresponding commercially available isocyanate using the procedure described for compound (69).

NMR (400 MHz, d$^6$-DMSO) $\delta_H$ 1.58 (7H, br m), 1.85 (7H, br m), 1.97 (3H, br m), 3.63 (2H, m), 3.91 (2H, m), 4.31 (1H, m), 5.51 (1H, s), 6.06 (1H, s), 7.38 (6H, m), 7.47 (2H, m)

LC (50/80) 97.6%, 8.27 min

Example 67

3-(2,2'-dichlorobenzhydryloxy)-N-(6-Fluoro-4H-benzo[1,3]dioxin-8-yl-methyl)azetidine-1-carboxamide (79)

This material was prepared from 3-(2,2'-dichlorobenzhydryloxy)azetidine hydrochloride (68) and the corresponding commercially available amine using the procedure described for compound (15) (77.7 mg, 80%).

MS 518 [M+H]$^+$

LC (50/80) 88.3%, 6.81 min

Example 68

3-(2,2'-dichlorobenzhydryloxy)-N-[2-(1-piperidyl)benzyl]azetidine-1-carboxamide (80)

This material was prepared from 3-(2,2'-dichlorobenzhydryloxy)azetidine hydrochloride (68) and the corresponding commercially available amine using the procedure described for compound (15).

MS 525 [M+H]+
LC (50/80) 92.0%, 8.26 min

Example 69

3-(2,2'-dichlorobenzhydryloxy)-N-(exo-2-norborna-nyl)azetidine-1-carboxamide (81)

This material was prepared from 3-(2,2'-dichlorobenzhydryloxy)azetidine hydrochloride (68) and the corresponding commercially available amine using the procedure described for compound (15).
MS 446 [M+H]+
LC (50/80) 95.5%, 7.30 min

Example 70

3-(2,2'-dichlorobenzhydryloxy)-N-(cyclohexylmethyl)azetidine-1-carboxamide (82)

This material was prepared from 3-(2,2'-dichlorobenzhydryloxy)azetidine hydrochloride (68) and the corresponding commercially available amine using the procedure described for compound (15).
MS 448 [M+H]+
LC (50/80) 97.9%, 7.53 min

Example 71

3-(2,2'-dichlorobenzhydryloxy)-N-(benzo[b]thiophen-3-yl-methyl)-azetidine-1-carboxamide (83)

This material was prepared from 3-(2,2'-dichlorobenzhydryloxy)azetidine hydrochloride (68) and the corresponding commercially available amine using the procedure described for compound (15).
MS 498 [M+H]+
LC (50/80) 93.2%, 7.74 min

Preparation of 4,4'-dibromobenzhydrol (84)

This material was prepared from 4,4'-dibromobenzophenone using the procedure described for compound (7) (9.67 g, 96%).
NMR (400 MHz, d$^6$-DMSO) $\delta_H$ 5.68 (1H, d, J 4.0 Hz), 6.06 (1H, d, J 4.0 Hz), 7.31 (4H, m), 7.48 (4H, m)
LC (50/80) 99.7%, 6.29 min

Preparation of 1-benzhydryl-3-(4,4'-dibromobenzhydryloxy)azetidine (85)

This material was prepared from 4,4'-dibromobenzhydrol (84) using the procedure described for compound (8) (6.15 g, 66%).
NMR (400 MHz, d$^6$-DMSO) $\delta_H$ 2.80 (2H, m), 3.25 (2H, m), 4.14 (1H, t, J 6.0 Hz), 4.41 (1H, s), 5.47 (1H, s), 7.16 (2H, m), 7.25 (8H, m), 7.38 (4H, m), 7.52 (4H, m)
LC (50/80) 97.7%, 4.01 min

Preparation of 3-(4,4'-dibromobenzhydryloxy)azetidine hydrochloride (86)

This material was prepared from 1-benzhydryl-3-(4,4'-dibromobenzhydryloxy)azetidine (85) using the procedure described for compound (9) (1.15 mg, 30%).
NMR (400 MHz, d$^6$-DMSO) $\delta_H$ 3.85 (2H, br s), 4.02 (2H, br s), 4.38 (1H, q, J 5.5 Hz), 5.61 (1H, s), 7.31 (4H, m), 7.56 (4H, m), 8.71 (2H, br d)

Example 72

3-(4,4'-dibromobenzhydryloxy)-N-(tert-butyl)azetidine-1-carboxamide (87)

This material was prepared from 3-(4,4'-dibromobenzhydryloxy)azetidine hydrochloride (86) using the procedure described for compound (10) (92.0 mg, 80%).
NMR (400 MHz, d$^6$-DMSO) $\delta_H$ 1.20 (9H, s), 3.58 (2H, m), 3.85 (2H, m), 4.21 (1H, m), 5.51 (1H, s), 5.61 (1H, s), 7.30 (4H, m), 7.54 (4H, m)
LC (50/80) 93.6%, 7.41 min

Example 73

3-(4,4'-dibromobenzhydryloxy)-N-(iso-propyl)azetidine-1-carboxamide (88)

This material was prepared from 3-(4,4'-dibromobenzhydryloxy)azetidine hydrochloride (86) using the procedure described for compound (10).
NMR (400 MHz, d$^6$-DMSO) $\delta_H$ 1.00 (6H, d, J 6.5 Hz), 3.56 (2H, m), 3.64 (1H, m), 3.84 (2H, m), 4.27 (1H, m), 5.51 (1H, s), 6.00 (1H, m), 7.30 (4H, m), 7.55 (4H, m)
LC (50/80) 97.5%, 7.15 min

Example 74

3-(4,4'-dibromobenzhydryloxy)-N-(iso-butyl)azetidine-1-carboxamide (89)

This material was prepared from 3-(4,4'-dibromobenzhydryloxy)azetidine hydrochloride (86) using the procedure described for compound (10).
NMR (400 MHz, d$^6$-DMSO) $\delta_H$ 0.78 (3H, t, J 7.5 Hz), 0.97 (3H, d, J 6.5 Hz), 1.33 (2H, m), 3.45 (1H, m), 3.58 (2H, m), 3.84 (2H, m), 4.28 (1H, m), 5.51 (1H, s), 5.96 (1H, d, J 8.5 Hz), 7.30 (4H, m), 7.54 (4H, m)
LC (50/80) 98.6%, 7.41 min

Example 75

3-(4,4'-dibromobenzhydryloxy)-N-(n-propyl)azetidine-1-carboxamide (90)

This material was prepared from 3-(4,4'-dibromobenzhydryloxy)azetidine hydrochloride (86) using the procedure described for compound (10).
NMR (400 MHz, d$^6$-DMSO) $\delta_H$ 0.79 (3H, t J 7.0 Hz), 1.35 (2H, m), 2.89 (2H, m), 3.58 (2H, m), 3.84 (2H, m), 4.28 (1H, m), 5.51 (1H, s), 6.25 (1H, t, J 6.0 Hz) 7.30 (4H, m), 7.54 (4H, m)
LC (50/80) 97.0%, 7.12 min

Example 76

3-(4,4'-dibromobenzhydryloxy)-N-(n-butyl)azetidine-1-carboxamide (91)

This material was prepared from 3-(4,4'-dibromobenzhydryloxy)azetidine hydrochloride (86) using the procedure described for compound (10).

NMR (400 MHz, d⁶-DMSO) $\delta_H$ 0.84 (3H, t, J 7.0 Hz), 1.23 (2H, m), 1.32 (2H, m), 2.93 (2H, m), 3.58 (2H, m), 3.84 (2H, m), 4.28 (1H, m), 5.51 (1H, s), 6.22 (1H, t. J 6.0 Hz), 7.30 (4H, m), 7.55 (4H, m)
LC (50/80) 98.0%, 7.42 min Example 77

3-(4,4'-dibromobenzhydryloxy)-N-(cyclopentyl) azetidine-1-carboxamide (92)

This material was prepared from 3-(4,4'-dibromobenzhydryloxy)azetidine hydrochloride (86) using the procedure described for compound (10).
NMR (400 MHz, d⁶-DMSO) $\delta_H$ 1.32 (2H, m), 1.44 (2H, m), 1.59(2H, m), 1.73(2H, m), 3.60 (2H, m), 3.83 (3H, m), 4.27 (1H, m), 5.50 (1H, s), 6.09 (1H, m), 7.30 (4H, m), 7.55 (4H, m)
LC (50/80) 97.6%, 7.69 min Example 78

3-(4,4'-dibromobenzhydryloxy)-N-(cyclohexyl)azetidine-1-carboxamide (93)

This material was prepared from 3-(4,4'-dibromobenzhydryloxy)azetidine hydrochloride (86) using the procedure described for compound (10).
NMR (400 MHz, d⁶-DMSO) $\delta_H$ 1.12 (5H, m), 1.55 (1H, br m), 1.67 (4H, br m), 3.56 (2H, m), 3.84 (2H, m), 4.28 (1H, m), 5.51 (1H, s), 6.00 (1H, m), 7.30 (4H, m), 7.54 (4H, m)
LC (50/80) 99.8%, 7.93 min Example 79

3-(4,4'-dibromobenzhydryloxy)-N-(phenethyl)azetidine-1-carboxamide (94)

This material was prepared from 3-(4,4'-dibromobenzhydryloxy)azetidine hydrochloride (86) using the procedure described for compound (10).
NMR (400 MHz, d⁶-DMSO) $\delta_H$ 2.66 (2H, m), 3.15 (2H, m), 3.58 (2H, m), 3.84 (2H, m), 4.29 (1H, m), 5.51 (1H, s), 6.37 (1H, m), 7.18 (3H, m), 7.29 (6H, m), 7.55 (4H, m)
LC (50/80) 98.9%, 7.91 min Example 80

3-(4,4'-dibromobenzhydryloxy)-N-(1-adamantyl) azetidine-1-carboxamide (95)

This material was prepared from 3-(4,4'-dibromobenzhydryloxy)azetidine hydrochloride (86) using the procedure described for compound (10).
NMR (400 MHz, d⁶-DMSO) $\delta_H$ 0.95 (1H, m), 1.58 (6H, m), 1.85 (6H, m), 1.97 (3H, m), 3.57 (2H, m), 3.81 (2H, m), 4.23 (1H, m), 5.50 (2H, m), 7.31 (4H, m), 7.55 (4H, m)
LC (50/80) 98.0%, 9.44 min Preparation of 2-(trifluoromethyl)-4-chlorobenzhydrol (96)

Magnesium turnings (4.21 g, 170 mmol) were stirred under nitrogen for 10 min. Stirring was halted and a solution of 2-bromobenzotrifluoride (36.37 g, 160 mmol) in dry THF (160 mL) was added via a dropping funnel until the magnesium turnings were just covered. The reaction mixture was heated with a hot-air gun until localised turbidity was observed. At this point, stirring was initiated, and the rate of the reaction was subsequently controlled with intermittent use of an ice-water bath, and varying the rate of addition of the remaining 2-bromobenzotrifluoride solution. After complete addition, the mixture was allowed to stir for 1 h, then used as a ~0.9 M solution.

To a stirred solution of 4-chlorobenzaldehyde (2.17 g, 15 mmol) in anhydrous THF (10 mL) was added a solution of 2-(trifluoromethyl)phenylmagnesium bromide (~0.9 M; 18 mL, 16 mmol) over 2 min. After 16 h, the resultant mixture was partitioned between diethyl ether and 1N HCl. The aqueous phase was extracted with diethyl ether (2×30 mL) and the combined organic extracts were washed with 1N HCl, brine and dried (MgSO₄). Evaporation under reduced pressure afforded the desired product as an amber oil (4.63 g, 100%).
MS 269 [M−OH]⁺
LC (50/80) 97.6%, 5.47 min Preparation of 1-benzhydryl-3-[2-(trifluoromethyl)-4'-chlorobenzhydryloxy]azetidine (97)

This material was prepared from 1-benzhydryl-3-azetidinol (1) (40.1 mmol) and 2-(trifluoromethyl)-4-chlorobenzhydrol (96) (80.2 mmol) using the procedure described for compound (3) (13.5 g, 66%).
NMR (400 MHz, d⁶-DMSO) $\delta_H$ 2.74 (1H, br t), 2.86 (1H, br t), 3.20 (1H, br t), 3.29(1H, br t), 4.15 (1H, q, J 6.0 Hz), 4.39 (1H, s), 5.71 (1H, s), 7.16 (2H, m), 7.26 (6H, m), 7.38 (6H, m), 7.54 (1H, m), 7.70 (3H, m)

Preparation of 3-[2-(trifluoromethyl)-4'-chlorobenzhydryloxy]azetidine hydrochloride (98)

This material was prepared from 1-benzhydryl-3-[2-(trifluoromethyl)-4'-chlorobenzhydryloxy]azetidine (97) (25.6 mmol) using the procedure described for compound (9) (8.2 g, 85%).
NMR (400 MHz, d⁶-DMSO) $\delta_H$ 3.78 (1H, m), 3.97 (3H, m), 4.89 (1H, q, J 6.0 Hz), 5.85 (1H, s), 7.33 (2H, m), 7.44 (2H, m), 7.59 (1H, m), 7.76 (3H, m), 8.97 (1H, bs)

Example 81

3-[2-(trifluoromethyl)-4'-chlorobenzhydryloxy]-N-(tert-butyl)azetidine-1-carboxamide (99)

This material was prepared from 3-[2-(trifluoromethyl)-4'-chlorobenzhydryloxy]azetidine hydrochloride (98) (1.32 mmol) and tert-butyl isocyanate (1.32 mmol) using the procedure described for compound (10) (474 mg, 81%).
NMR (400 MHz, d⁶-DMSO) $\delta_H$ 1.20 (9H, s), 3.51 (1H, m), 3.65 (1H, m), 3.84 (2H, m), 4.25 (1H, m), 5.62 (1H, s), 5.73 (1H, s), 7.31 (2H, m), 7.39 (2H, m), 7.57 (1H, m), 7.75 (3H, m)
LC (50/80) 98.6%, 6.93 min Example 82

3-[2-(trifluoromethyl)-4'-chlorobenzhydryloxy]-N-(n-propyl)azetidine-1-carboxamide (100)

This material was prepared from 3-[2-(trifluoromethyl)-4'-chlorobenzhydryloxy]azetidine hydrochloride (98) and the corresponding isocyanate using the procedure described for compound (10).

NMR (400 MHz, d⁶-DMSO) $\delta_H$ 0.79 (3H, t, J 7.5 Hz), 1.33 (2H, m), 3.52 (1H, m), 3.65 (1H, m), 3.85 (2H, m), 4.30 (1H, m), 5.74 (1H, s), 6.23 (1H, s), 7.30 (2H, m), 7.42 (2H, m), 7.57 (1H, m), 7.75 (3H, m)

LC (50/80) 96.7% 6.46 min

Example 83

3-[2-(trifluoromethyl)-4'-chlorobenzhydryloxy]-N-(iso-propyl)azetidine-1-carboxamide (101)

This material was prepared from 3-[2-(trifluoromethyl)-4'-chlorobenzhydryloxy]azetidine hydrochloride (98) and the corresponding isocyanate using the procedure described for compound (10).

NMR (400 MHz, d⁶-DMSO) $\delta_H$ 1.00 (6H, d, J 6.5 Hz), 3.54 (1H, m), 3.64 (2H, m), 3.84 (2H, m), 4.28 (1H, m), 5.74 (1H, s), 6.02 (1H, s), 7.30 (2H, m), 7.41 (2H, m), 7.58 (1H, m), 7.79 (3H, m)

LC (50/80) 98.2%, 6.22 min

Example 84

3-[2-(trifluoromethyl)-4'-chlorobenzhydryloxy]-N-(n-butyl)azetidine-1-carboxamide (102)

This material was prepared from 3-[2-(trifluoromethyl)-4'-chlorobenzhydryloxy]azetidine hydrochloride (98) and the corresponding isocyanate using the procedure described for compound (10).

NMR (400 MHz, d⁶-DMSO) $\delta_H$ 0.84 (3H, t, J 7.5 Hz), 1.23 (2H, m), 1.32 (2H, m), 3.35 (1H, m), 3.65 (1H, m), 3.85 (2H, m), 4.29 (1H, m), 5.74 (1H, s), 6.23 (1H, s), 7.13 (2H, m), 7.42 (2H, m), 7.56 (1H, m), 7.74 (3H, m)

LC (50/80) 98.0%, 7.02 min

Example 85

3-[2-(trifluoromethyl)-4'-chlorobenzhydryloxy]-N-(sec-butyl)azetidine-1-carboxamide (103)

This material was prepared from 3-[2-(trifluoromethyl)-4'-chlorobenzhydryloxy]azetidine hydrochloride (98) and the corresponding isocyanate using the procedure described for compound (10).

NMR (400 MHz, d⁶-DMSO) $\delta_H$ 0.78 (3H, m), 0.97 (3H, d, J 6.0 Hz), 1.33 (2H, m), 3.53 (1H, m), 3.65 (1H, m), 3.85 (2H, m), 4.28 (1H, m), 5.74 (1H, s), 5.97 (1H, br d), 7.31 (2H, m), 7.42 (2H, m), 7.57 (1H, m), 7.75 (3H, m)

LC (50/80) 98.0%, 6.87 min

Example 86

3-[2-(trifluoromethyl)-4'-chlorobenzhydryloxy]-N-(ethyl propionate-3-yl)azetidine-1-carboxamide (104)

This material was prepared from 3-[2-(trifluoromethyl)-4'-chlorobenzhydryloxy]azetidine hydrochloride (98) and the corresponding isocyanate using the procedure described for compound (10).

NMR (400 MHz, d⁶-DMSO) $\delta_H$ 1.14 (3H, t, J 7.0 Hz), 2.38 (2H, t, J 7.0 Hz), 3.54 (1H, m), 3.66 (1H, m), 3.85 (2H, m), 4.04 (2H, q, J 7.0 Hz), 4.30 (1H, m), 5.74 (1H, s), 6.37 (1H, br s), 7.31 (2H, m), 4.24 (2H, m), 5.57 (1H, m), 7.75 (3H, m)

LC (50/80) 95.0%, 6.40 min

Example 87

3-[2-(trifluoromethyl)-4'-chlorobenzhydryloxy]-N-(methyl 3-phenyl-propionate-2-yl)azetidine-1-carboxamide (105)

This material was prepared from 3-[2-(trifluoromethyl)-4'-chlorobenzhydryloxy]azetidine hydrochloride (98) and the corresponding isocyanate using the procedure described for compound (10).

NMR (400 MHz, d⁶-DMSO) $\delta_H$ 2.88 (1H, m), 2.97 (1H, m), 3.50 (1H, m), 3.62 (1H, m), 3.84 (2H, m), 4.26 (2H, m), 5.73 (1H, s), 6.75 (1H, m), 7.23 (7H, m), 7.44 (2H, m), 7.56 (1H, m), 7.75 (3H, m)

LC (50/80) 96.0%, 7.40 min

Example 88

3-[2-(trifluoromethyl)-4'-chlorobenzhydryloxy]-N-(ethyl)azetidine-1-carboxamide (106)

This material was prepared from 3-[2-(trifluoromethyl)-4'-chlorobenzhydryloxy]azetidine hydrochloride (98) and the corresponding isocyanate using the procedure described for compound (10).

NMR (400 MHz, d⁶-DMSO) $\delta_H$ 0.951 (3H, t, J 7.0 Hz), 2.96 (2H, m), 3.53 (1H, m), 3.64 (1H, m), 3.86 (2H, m), 4.28 (1H, m), 5.74 (1H, s), 6.25 (1H, m), 7.30 (2H, m), 7.42 (2H, m), 7.56 (1H, m), 7.74 (3H, m)

LC (80/20) 90.6%, 0.77 min

Example 89

3-[2-(trifluoromethyl)-4'-chlorobenzhydryloxy]-N-[(S)-α-methyl-benzyl]azetidine-1-carboxamide (107)

This material was prepared from 3-[2-(trifluoromethyl)-4'-chlorobenzhydryloxy]azetidine hydrochloride (98) and the corresponding isocyanate using the procedure described for compound (10).

NMR (400 MHz, d⁶-DMSO) $\delta_H$ 3.58 (1H, m), 3.70 (1H, m), 3.89 (2H, m), 4.32 (1H, m), 4.73 (1H, m), 6.67 (1H, m), 7.31 (6H, m), 7.42 (2H, m), 7.55 (1H, m), 7.79 (3H, m)

LC (80/20) 96.0%, 1.09 min

Example 90

3-[2-(trifluoromethyl)-4'-chlorobenzhydryloxy]-N-(2,2,4-trimethylpent-4-yl)azetidine-1-carboxamide (108)

This material was prepared from 3-[2-(trifluoromethyl)-4'-chlorobenzhydryloxy]azetidine hydrochloride (98) and the corresponding isocyanate using the procedure described for compound (10).

NMR (400 MHz, d⁶-DMSO) $\delta_H$ 0.92 (9H, s), 1.24 (6H, s), 1.64 (2H, s), 3.52 (1H, m), 3.65 (1H, m), 3.83 (2H, m), 4.25 (1H, m), 5.73 (1H, s), 7.30 (2H, m), 7.42 (2H, m), 7.57 (1H, m), 7.74 (3H, m)

LC (80/20) 97.2%, 1.75 min

Example 91

3-[2-(trifluoromethyl)-4'-chlorobenzhydryloxy]-N (cyclopentyl)-azetidine-1-carboxamide (109)

This material was prepared from 3-[2-(trifluoromethyl)-4'-chlorobenzhydryloxy]azetidine hydrochloride (98) and the corresponding isocyanate using the procedure described for compound (10).

NMR (400 MHz, d$^6$-DMSO) $\delta_H$ 1.31 (2H, m), 1.44 (2H, m), 1.58 (2H, m), 1.73 (2H, m), 3.54 (1H, m), 3.67 (1H, m), 3.83 (3H, m), 4.28(1H, m), 5.73 (1H, s), 6.07 (1H, m), 7.30 (2H, m), 7.42 (2H, m), 7.57 (1H, m), 7.74 (3H, m)

LC (80/20) 99.5%, 1.03 min

Example 92

3-(2,4'-dichlorobenzhydryloxy)-N-(2,2,4-trimethyl-pent-4-yl)azetidine-1-carboxamide (110)

This material was prepared from 3-(2,4'-dichlorobenzhydryloxy)azetidine hydrochloride (9) and the corresponding isocyanate using the procedure described for compound (10).

MS 464 [M+H]$^+$

LC (80/20) 97.9%, 1.80 min

Example 93

3-(2,4'-dichlorobenzhydryloxy)-N-(2-methylbut-2-yl)azetidine-1-carboxamide (111)

This material was prepared from 3-(2,4'-dichlorobenzhydryloxy)azetidine hydrochloride (9) and the corresponding isocyanate using the procedure described for compound (10).

MS 422 [M+H]$^+$

LC (50/80) 99.6%, 1.15 min

Preparation of 2-(trifluoromethyl)-2'-fluoro-4'-bromobenzhydrol (112)

This material was prepared from 2-(trifluoromethyl)phenylmagnesium bromide (60 mmol) and 4-bromo-2-fluorobenzaldehyde (54 mmol) using the procedure described for compound (96) (12.3 g, 74%).

NMR (400 MHz, d$^6$-DMSO) $\delta_H$ 5.99 (1H, br d), 6.33 (1H, d, J 4.5 Hz), 7.27 (2H, m), 7.38 (2H, m), 7.57 (2H, m), 7.71 (1H, m)

Preparation of 1-benzhydryl-3-[2-(trifluoromethyl)-2'-fluoro-4'-bromo-benzhydryloxy]azetidine (113)

This material was prepared from 1-benzhydryl-3-azetidinol (1) (23.0 mmol) and 2-(trifluoromethyl)-2'-fluoro-4'-bromobenzhydrol (112) (34.0 mmol) using the procedure described for compound (3) (8.84 g, 67%).

NMR (400 MHz, d$^6$-DMSO) $\delta_H$ 2.76 (1H, t, J 6.5 Hz), 2.87 (1H, t, J 6.5 Hz), 3.23 (1H, br t), 3.29 (1H, br t), 4.15 (1H, q), 4.39 (1H, s), 5.70 (1H, s), 7.17 (2H, m), 7.25 (6H, m), 7.37 (6H, m), 7.59 (2H, m), 7.73 (1H, m)

Preparation of 3-[2-(trifluoromethyl)-2'-fluoro-4'-bromobenzhydryloxy]azetidine hydrochloride (114)

This material was prepared from 1-benzhydryl-3-[2-(trifluoromethyl)-2'-fluoro-4'-bromobenzhydryloxy]azetidine (113) (15 mmol) using the procedure described for compound (9) (2.26 g, 51%).

NMR (400 MHz, d$^6$-DMSO) $\delta_H$ 3.78 (1H, br s), 3.96 (3H, br d), 4.42 (1H,m), 5.83 (1H, s), 7.33 (2H, m), 7.41 (2H, m), 7.70 (3H, m)

LC (50/80) 99.7%, 4.67 min

Example 94

3-[2-(trifluoromethyl)-2'-fluoro-4'-bromobenzhydryloxy]-N-(tert-butyl)azetidine-1-carboxamide (115)

This material was prepared from 3-[2-(trifluoromethyl)-2'-fluoro-4'-bromobenzhydryloxy]azetidine hydrochloride (114) and tert-butyl isocyanate (4.54 mmol) using the procedure described for compound (5) (1.33 g, 58%).

NMR (400 MHz, d$^6$-DMSO) $\delta_H$ 1.20 (9H, s), 3.58 (1H, m), 3.64 (1H, m), 3.88 (2H, m), 4.26 (1H, m), 5.98 (1H, s), 7.18 (1H, m), 7.44 (1H, m), 7.61 (2H, m), 7.78 (3H, m)

LC (50/80) 99.0%, 7.15 min

Found: C, 52.29; H, 4.61; N, 5.63, C22H23BrF4N2O2 requires: C, 52.50; H, 4.61; N, 5.56%

Preparation of 2-(trifluoromethyl)-4'-(methylthio) benzhydrol (116)

This material was prepared from 2-(trifluoromethyl)phenylmagnesium bromide (32 mmol) and 4-(methylthio)benzaldehyde (30 mmol) using the procedure described for compound (96) (9.4 g, 100%).

NMR (400 MHz, CDCl$_3$) $\delta_H$ 6.26 (1H, s), 7.21 (2H, m), 7.28 (2H, m), 7.39 (1H, m), 7.55 (1H, m), 7.64 (2H, m)

Preparation of 1-benzhydryl-3-[2-(trifluoromethyl)-4'-(methylthio)-benzhydryloxy]azetidine (117)

This material was prepared from 1-benzhydryl-3-azetidinol (1) (15 mmol) and 2-(trifluoromethyl)-4'-(methylthio) benzhydrol (116) (30 mmol) using the procedure described for compound (3) (4.68 g, 60%).

NMR (400 MHz, d$^6$-DMSO) $\delta_H$ 2.42 (3H, s), 2.75 (1H, m), 2.85 (1H, m), 3.21 (1H, m), 3.29 (1H, m), 4.14 (1H, m), 4.38 (1H, s), 5.66 (1H, s), 7.21 (10H, m), 7.37 (4H, m), 7.51 (1H, m), 7.70 (3H, m)

Preparation of 3-[2-trifluoromethyl-4'-(methylthio) benzhydryloxy]azetidine hydrochloride (118)

This material was prepared from 1-benzhydryl-3-[2-(trifluoromethyl)-4'-(methylthio)benzhydryloxy]azetidine (117) (8.7 mmol) using the procedure described for compound (9) (2.29 g, 68%).

NMR (400 MHz, d$^6$-DMSO) $\delta_H$ 3.89 (4H, br m), 4.41 (1H, m), 5.80 (1H, s), 7.24 (4H, s), 7.57 (1H, m), 7.75 (3H, m), 9.30 (2H, br s)

LC (50/80) 94.5%, 3.55 min

Example 95

3-[2-(trifluoromethyl)-4'-(methylthio)benzhydryloxy]-N-(tert-butyl)-azetidine-1-carboxamide (119)

This material was prepared from 3-[2-trifluoromethyl-4'-(methylthio)benzhydryloxy]azetidine hydrochloride (118) (1.28 mmol), tert-butyl isocyanate (1.28 mmol) and mp-carbonate (2.62 mmol/g, 3.85 mmol) using the procedure described for compound (10) (433 mg, 75%).

NMR (400 MHz, d$^6$-DMSO) δ$_H$ 1.20 (9H, s), 2.44 (3H, s), 3.53 (1H, m), 3.64 (1H, m), 3.83 (2H, m), 4.22(1H, m), 5.68(1H, s), 7.22 (4H, m), 7.54 (1H, m), 7.74 (3H, m)

LC (50/80) 98.0%, 7.00 min

Example 96

3-[2-(trifluoromethyl)-4'-(methylthio)benzhydryloxy]-N-(iso-propyl)azetidine-1-carboxamide (120)

This material was prepared from 3-[2-trifluoromethyl-4'-(methylthio)benzhydryloxy]azetidine hydrochloride (118) and the corresponding isocyanate using the procedure described for compound (10).

NMR (400 MHz, d$^6$-DMSO) δ$_H$ 1.00 (6H, d, J 6.5 Hz), 2.44 (3H, s), 3.54 (1H, m), 3.64 (2H, m), 3.84 (2H, m), 4.27 (1H, m), 5.69 (1H, s), 6.02 (1H, m), 7.22 (4H, m), 7.55 (1H, m), 7.74 (3H, m)

LC (50/80) 99.0%, 6.36 min

Example 97

3-[2-(trifluoromethyl)-4'-(methylthio)benzhydryloxy]-N-(sec-butyl)-azetidine-1-carboxamide (121)

This material was prepared from 3-[2-trifluoromethyl-4'-(methylthio)benzhydryloxy]azetidine hydrochloride (118) and the corresponding isocyanate using the procedure described for compound (10).

NMR (400 MHz, d$^6$-DMSO) δ$_H$ 0.78 (3H, t, J 7.0 Hz), 0.97 (3H, d, J 7.5 Hz), 1.32 (2H, m), 2.45 (3H, s), 3.45 (1H, m), 3.54 (1H, m), 3.65 (1H, m), 3.85 (2H, m), 4.27(1H, m), 5.70 (1H, s), 5.96 (1H, s), 7.22 (4H, m), 7.55 (1H, m), 7.74 (3H, m)

LC (50/80) 98.0%, 6.84 min

Example 98

3-[2-(trifluoromethyl)-4'-(methylthio)benzhydryloxy]-N-(benzyl)-azetidine-1-carboxamide (122)

This material was prepared from 3-[2-trifluoromethyl-4'-(methylthio)benzhydryloxy]azetidine hydrochloride (118) and the corresponding isocyanate using the procedure described for compound (10).

NMR (400 MHz, d$^6$-DMSO) δ$_H$ 2.44 (3H, s), 3.60 (1H, m), 3.69 (1H, m), 3.90 (2H, m), 4.15 (2H, m), 4.31(1H, m), 5.70 (1H, s), 6.87 (1H, m), 7.24 (8H, m), 7.55 (1H, m), 7.75 (3H, m)

LC (50/80) 96.1%, 7.17 min

Preparation of 2-(trifluoromethyl)-4-fluoro-4'-chlorobenzhydrol (123)

This material was prepared from 4-chlorophenylmagnesium bromide (28.6 mmol) and 4-fluoro-2-(trifluoromethyl) benzaldehyde (26.0 mmol) using the procedure described for compound (2) (6.04 g, 76%).

NMR (400 MHz, d$^6$-DMSO) δ$_H$ 6.00 (1H, br d), 6.33 (1H, d, J 4.5 Hz), 7.26 (2H, m), 7.38 (2H, m), 7.57 (2H, m), 7.12 (1H, m)

Preparation of 1-benzhydryl-3-[2-(trifluoromethyl)-4-fluoro-4'-chlorobenzhydryloxy]azetidine (124)

This material was prepared from 1-benzhydryl-3-azetidinol (1) (9.8 mmol) and 2-(trifluoromethyl)-4-fluoro-4'-chlorobenzhydrol (123) (19.7 mmol) using the procedure described for compound (3) (2.31 g, 45%).

NMR (400 MHz, d$^6$-DMSO) δ$_H$ 2.76 (1H, t, J 6.5 Hz), 2.86 (1H, t, J 6.5 Hz), 3.23 (1H, t, J=6.5 Hz), 3.30 (1H, t, J 6.5 Hz), 4.16 (1H, m), 4.40 (1H, s), 5.70 (1H, s), 7.17 (2H, m), 7.26 (6H, m), 7.37 (6H, m), 7.60 (2H, m), 7.75(1H, m)

Preparation of 3-[2-(trifluoromethyl)-4-fluoro-4'-chlorobenzhydryloxy]azetidine hydrochloride (125)

This material was prepared from 1-benzhydryl-3-[2-(trifluoromethyl)-4-fluoro-4'-chlorobenzhydryloxy]azetidine (124) (3.8 mmol) using the procedure described for compound (9) (1.45 g, 97%).

NMR (400 MHz, d$^6$-DMSO) δ$_H$ 3.31 (1H, br s), 3.78 (1H, br s), 3.96 (3H, br d), 4.40 (1H, m), 5.83 (1H, s), 7.32 (2H, m), 7.45 (2H, m), 7.70 (3H, m), 8.97 (2H, br d)

LC (50/80) 99.7%, 4.67 min

Example 99

3-[2-(trifluoromethyl)-4-fluoro-4'-chlorobenzhydryloxy]-N-(tert-butyl)azetidine-1-carboxamide (126)

This material was prepared from 3-[2-(trifluoromethyl)-4-fluoro-4'-chlorobenzhydryloxy]azetidine hydrochloride (125) (0.25 mmol), tert-butyl isocyanate (0.25 mmol) and MP-carbonate (2.62 mmol/g, 0.76 mmol) using the procedure described for compound (10) (72.4 mg, 63%).

NMR (400 MHz, d$^6$-DMSO) δ$_H$ 1.21 (9H, s), 3.52 (1H, m), 3.64 (1H, m), 3.84 (2H, m), 4.25 (1H, m), 5.71 (1H, s), 7.30 (2H, m), 7.42 (2H, m), 7.62 (2H, m), 7.77(1H, m)

LC (50/80) 95.0%, 7.35 min

Example 100

3-[2-(trifluoromethyl)-4-fluoro-4'-chlorobenzhydryloxy]-N-(iso-propyl)azetidine-1-carboxamide (127)

This material was prepared 3-[2-(trifluoromethyl)-4-fluoro-4'-chlorobenz-hydryloxy]azetidine hydrochloride (125) and the corresponding isocyanate using the procedure described for compound (10).

NMR (400 MHz, d$^6$-DMSO) δ$_H$ 1.00 (6H, d, J 6.5 Hz), 3.51 (1H, m), 3.65 (2H, m), 3.83(2H, m), 4.28 (1H, m), 5.72 (1H, s), 6.02 (1H, m), 7.32 (2H, m), 7.40 (2H, m), 7.64 (2H, m), 7.79 (1H, m)

LC (50/80) 99.0%, 6.84 min

Example 101

3-[2-(trifluoromethyl)-4-fluoro-4'-chlorobenzhydryloxy]-N-(sec-butyl)azetidine-1-carboxamide (128)

This material was prepared 3-[2-(trifluoromethyl)-4-fluoro-4'-chlorobenzhydryloxy]azetidine hydrochloride (125) and the corresponding isocyanate using the procedure described for compound (10).

NMR (400 MHz, d$^6$-DMSO) δ$_H$ 0.78 (3H, t, J 7.5 Hz), 0.97 (3H, d, J 6.5 Hz), 1.33 (2H, m), 3.45 (1H, m), 3.53 (1H, m), 3.65 (1H, m), 3.85 (2H, m), 4.30 (1H, m), 5.73 (1H, s), 5.96 (1H, m), 7.30 (2H, m), 7.43 (2H, m), 7.62 (2H, m), 7.78 (1H, m)

LC (50/80) 99.0%, 7.29 min

Example 102

3-[2-(trifluoromethyl)-4-fluoro-4'-chlorobenzhydryloxy]-N-(cyclohexyl)azetidine-1-carboxamide (129)

This material was prepared 3-[2-(trifluoromethyl)-4-fluoro-4'-chlorobenzhydryloxy]azetidine hydrochloride (125) and the corresponding isocyanate using the procedure described for compound (10).

NMR (400 MHz, d⁶-DMSO) $\delta_H$ 1.12 (5H, m), 1.53 (1H, m), 1.66 (4H, m), 3.52 (1H, m), 3.64 (1H, m), 3.83 (2H, m), 4.28 (1H, m), 5.71 (1H, s), 6.01 (1H, m), 7.31 (2H, m), 7.41 (2H, m), 7.62 (2H, m), 7.70 (1H, m)

LC (50/80) 99.9%, 7.77 min

Example 103

3-[2-(trifluoromethyl)-4-fluoro-4'-chlorobenzhydryloxy]-N-(benzyl)azetidine-1-carboxamide (130)

This material was prepared 3-[2-(trifluoromethyl)-4-fluoro-4'-chlorobenzhydryloxy]azetidine hydrochloride (125) and the corresponding isocyanate using the procedure described for compound (10).

NMR (400 MHz, d⁶-DMSO) $\delta_H$ 3.58 (1H, m), 3.70 (1H, m), 3.91 (2H, m), 4.16 (2H, m), 4.32 (1H, m), 5.74 (1H, s), 6.87 (1H, m), 6.12 (3H, m), 7.30 (4H, m), 7.43 (2H, m), 7.62 (2H, m), 7.85 (1H, m)

LC (50/80) 94.0%, 7.49 min

Preparation of 2-(trifluoromethyl)benzhydrol (131)

This material was prepared from 2-(trifluoromethyl)phenylmagnesium bromide (16 mmol) and benzaldehyde (15 mmol) using the procedure described for compound (96) (3.7 g, 98%).

NMR (400 MHz, CDCl₃) $\delta_H$ 6.31 (1H, s), 7.26 (1H, m), 7.36 (5H, m), 7.53 (1H, m), 7.65 (2H, m)

Preparation of 1-benzhydryl-3-[2-(trifluoromethyl)benzhydryloxy]azetidine (132)

This material was prepared from 1-benzhydrol-3-azetidinol (1) (7.5 mmol) and 2-(trifluoromethyl)benzhydrol (131) (15 mmol) using the procedure described for compound (3) (1.81 g, 51%).

NMR (400 MHz, d⁶-DMSO) $\delta_H$ 2.75 (1H, br t), 2.85 (1H, br t), 3.21 (1H, br t), 3.27 (1H, br t), 4.15 (1H, m), 4.38 (1H, s), 5.71 (1H, s), 7.12-7.40 (12H, m), 7.49-7.72 (7H, m),

Preparation 3-[2-(trifluoromethyl)benzhydryloxy]azetidine hydrochloride (133)

This material was prepared from 1-benzhydryl-3-[2-(trifluoromethyl)-benzhydryloxy]azetidine (132) (3.8 mmol) using the procedure described for compound (9) (0.70 g, 60%).

NMR (400 MHz, d⁶-DMSO) $\delta_H$ 3.89 (4H, br m), 4.41 (1H, m), 5.80 (1H, s), 7.29 (3H, m), 7.35 (2H, m), 7.55 (1H, m), 7.74 (3H, m), 9.30 (2H, br s)

LC (50/80) 96.6%, 1.60 min

Example 104

3-[2-(trifluoromethyl)benzhydryloxy]-N-(tert-butyl)azetidine-1-carboxamide (134)

This material was prepared from 3-[2-(trifluoromethyl)benzhydryloxy]azetidine hydrochloride (133) (0.33 mmol), tert-butyl isocyanate (0.33 mmol) and MP-carbonate (2.62 mmol/g, 0.98 mmol) using the procedure described for compound (10) (99.5 mg, 75%).

NMR (400 MHz, d⁶-DMSO) $\delta_H$ 1.20 (9H, s), 3.54 (1H, m), 3.66 (1H, m), 3.84 (2H, m), 4.23 (1H, m), 5.63 (1H, s), 7.29 (3H, m), 7.35 (2H, m), 7.55 (1H, m), 7.74 (3H, m)

LC (50/80) 93.0%, 6.24 min

Example 105

3-[2-(trifluoromethyl)benzhydryloxy]-N-(iso-propyl)azetidine-1-carboxamide (135)

This material was prepared 3-[2-(trifluoromethyl)benzhydryloxy]azetidine hydrochloride (133) and the corresponding isocyanate using the procedure described for compound (10).

NMR (400 MHz, d-DMSO) $\delta_H$ 1.00 (6H, d, J 6.5 Hz), 3.55 (1H, m), 3.65 (2H, m), 3.84 (2H, m), 4.28 (1H, m), 5.74 (1H, s), 7.32 (5H, m), 7.55 (1H, m), 7.74 (3H, m)

LC (50/80) 91.0%, 5.51 min

Example 106

3-[2-(trifluoromethyl)benzhydryloxy]-N-(sec-butyl)azetidine-1-carboxamide (136)

This material was prepared 3-[2-(trifluoromethyl)benzhydryloxy]azetidine hydrochloride (133) and the corresponding isocyanate using the procedure described for compound (10).

NMR (400 MHz, d⁶-DMSO) $\delta_H$ 0.782 (3H, m), 0.972 (3H, d, J 6.0 Hz), 1.33 (2H, m), 3.45 (1H, m), 3.54 (1H, m), 3.65 (1H, m), 3.85 (2H, m), 4.28 (1H, m), 5.74 (1H, s), 7.32 (5H, m), 7.55 (1H, m), 7.74 (3H, m)

LC (50/80) 94.0%, 6.04 min

Example 107

3-[2-(trifluoromethyl)benzhydryloxy]-N-(cyclohexyl)azetidine-1-carboxamide (137)

This material was prepared 3-[2-(trifluoromethyl)benzhydryloxy]azetidine hydrochloride (133) and the corresponding isocyanate using the procedure described for compound (10).

NMR (400 MHz, d⁶-DMSO) $\delta_H$ 1.12 (5H, m), 1.55 (1H, m), 1.67 (4H, m), 3.54 (1H, m), 3.65 (1H, m), 3.85 (2H, m), 4.22 (1H, m), 5.74 (1H, s), 7.32 (5H, m), 7.55 (1H, m), 7.74 (3H, m)

LC (50/80) 96.0%, 6.79 min

Example 108

3-[2-(trifluoromethyl)benzhydryloxy]-N-(benzyl)azetidine-1-carboxamide (138)

This material was prepared 3-[2-(trifluoromethyl)benzhydryloxy]azetidine hydrochloride (133) and the corresponding isocyanate using the procedure described for compound (10).

NMR (400 MHz, d⁶-DMSO) δ$_H$ 3.59 (1H, m), 3.71 (1H, m), 3.91 (2H, m), 4.15 (2H, m), 4.31 (1H, m), 5.75 (1H, s), 6.87 (1H, m), 7.21 (3H, m), 7.32 (6H, m), 7.55 (1H, m), 7.75 (3H, m)

LC (50/80) 95.5%, 6.45 min

Preparation of 2-(trifluoromethyl)-4'-(trifluoromethoxy)benzaldehyde (139)

This material was prepared from 2-(trifluoromethyl)phenylmagnesium bromide (16 mmol) and 4-(trifluoromethoxy)benzaldehyde (15 mmol) using the procedure described for compound (96) (5.24 g, 100%).

NMR (400 MHz, CDCl₃) δ$_H$ 6.31 (1H, s), 7.17 (2H, m), 7.39 (3H, m), 7.57 (2H, m), 7.68 (1H, m)

Preparation of 1-benzhydryl-3-[2-(trifluoromethyl)-4'-(trifluoromethoxy)-benzhydryloxy]azetidine (140)

This material was prepared from 1-benzhydryl-3-azetidinol (1) (7.5 mmol) and 2-(trifluoromethyl)-4'-(trifluoromethoxy)benzaldehyde (139) (15 mmol) using the procedure described for compound (3) (2.65 g, 63%).

NMR (400 MHz, d⁶-DMSO) δ$_H$ 2.75 (1H, m), 2.85 (1H, m), 3.21 (1H, m), 3.30 (1H, m), 4.15 (1H, m), 4.39 (1H, s), 5.76 (1H, s), 7.16 (2H, m), 7.25 (3H, m), 7.37 (8H, m), 7.52 (1H, m), 7.72 (3H, m)

Preparation 3-[2-(trifluoromethyl)-4'-(trifluoromethoxy)benzhydryloxy]azetidine hydrochloride (141)

This material was prepared from 1-benzhydryl-3-[2-(trifluoromethyl)-4'-(trifluoromethoxy)benzhydryloxy]azetidine (140) (4.8 mmol) using the procedure described for compound (9) (1.32 g, 65%).

NMR (400 MHz, d⁶-DMSO) δ$_H$ 3.89 (4H, br m), 4.41 (1H, m), 5.80 (1H, s), 7.24 (4H, s), 7.57 (1H, m), 7.75 (3H, m), 9.30 (2H, br s)

LC (50/80) 93.5%, 4.63 min

Example 109

3-[2-(trifluoromethyl)-4'-(trifluoromethoxy)benzhydryloxy]-N-(tert-butyl)azetidine-1-carboxamide (142)

This material was prepared from 3-[2-(trifluoromethyl)-4'-(trifluoro-methoxy)benzhydryloxy]azetidine hydrochloride (141) (0.234 mmol), tert-butyl isocyanate (0.234 mmol) and MP-carbonate (2.62 mmol/g, 0.702 mmol) using the procedure described for compound (10) (78.7 mg, 69%).

NMR (400 MHz, d⁶-DMSO) δ$_H$ 1.20 (9H, s), 3.53 (1H, m), 3.69 (1H, m), 3.85 (2H, m), 4.25 (1H, m), 5.68 (1H, s), 7.35 (2H, m), 7.42 (2H, m), 7.58 (1H, m), 7.75 (3H, m)

LC (50/80) 98.0%, 7.31 min

Example 110

3-[2-(trifluoromethyl)-4'-(trifluoromethoxy)benzhydryloxy]-N-(iso-propyl)azetidine-1-carboxamide (143)

This material was prepared from 3-[2-(trifluoromethyl)-4'-(trifluoro-methoxy)benzyloxy]azetidine hydrochloride (141) and the corresponding isocyanate using the procedure described for compound (10).

NMR (400 MHz, d⁶-DMSO) δ$_H$ 1.00 (6H, d, J 6.5 Hz), 3.53 (1H, m), 3.67 (2H, m), 3.86 (2H, m), 4.28 (1H, m), 5.78 (1H, s), 7.35 (2H, m), 7.42 (2H, m), 7.58 (1H, m), 7.75 (3H, m)

LC (50/80) 95.0%, 6.85 min

Example 111

3-[2-(trifluoromethyl)-4'-(trifluoromethoxy)benzhydryloxy]-N-(sec-butyl)azetidine-1-carboxamide (144)

This material was prepared from 3-[2-(trifluoromethyl)-4'-(trifluoro-methoxy)benzyloxy]azetidine hydrochloride (141) and the corresponding isocyanate using the procedure described for compound (10).

NMR (400 MHz, d⁶-DMSO) δ$_H$ 0.79 (3H, m), 0.97 (3H, m), 1.34 (2H, m), 3.45 (1H, m), 3.55 (1H, m), 3.70 (1H, m), 3.86 (2H, m), 4.30 (1H, m), 5.79 (1H, s), 7.35 (2H, m), 7.42 (2H, m), 7.58 (1H, m), 7.75 (3H, m)

LC (50/80) 99.0%, 7.18 min

Example 112

3-[2-(trifluoromethyl)-4'-(trifluoromethoxy)benzhydryloxy]-N-(benzyl)azetidine-1-carboxamide (145)

This material was prepared from 3-[2-(trifluoromethyl)-4'-(trifluoro-methoxy)benzyloxy]azetidine hydrochloride (141) and the corresponding isocyanate using the procedure described for compound (10).

NMR (400 MHz, d⁶-DMSO) δ$_H$ 3.61 (1H, m), 3.75 (1H, m), 3.92 (2H, m), 4.16 (2H, m), 4.30 (1H, m), 5.80 (1H, s), 6.87 (1H, m), 7.21 (3H, m), 7.28 (2H, m), 7.35 (2H, m), 7.43 (2H, m), 7.57 (1H, m), 7.76 (3H, m)

LC (50/80) 99.0%, 7.76 min

Example 113

3-[2-(trifluoromethyl)-4'-chlorobenzhydryloxy]-N-(1-adamantyl)-azetidine-1-carboxamide (146)

This material was prepared from 3-[2-(trifluoromethyl)-4'-chlorobenzhydryloxy]azetidine hydrochloride (98) (0.55 mmol) and 1-adamantyl isocyanate (0.55 mmol) using the procedure described for compound (10) (229 mg, 83%).

MS 519 [M+H]⁺

LC (50/80) 99.6%, 8.45 min

Example 114

3-[2-(trifluoromethyl)-4'-chlorobenzhydryloxy]-N-(cyclohexyl)-azetidine-1-carboxamide (147)

This material was prepared from 3-[2-(trifluoromethyl)-4'-chlorobenzhydryloxy]azetidine hydrochloride (98) (0.55 mmol) and cyclohexyl isocyanate (0.55 mmol) using the procedure described for compound (10) (146 mg, 59%).

MS 467 [M+H]⁺

LC (50/80) 99.8%, 7.32 min

Example 115

3-[2-(trifluoromethyl)-4'-chlorobenzhydryloxy]-N-(tert-amyl)azetidine-1-carboxamide (148)

Compound (98) was converted to the corresponding free-base by partitioning between dichloromethane and 0.5N sodium hydroxide.

To a stirred solution of triphosgene (187 mg, 0.63 mmol) in dry dichloromethane (5 mL) at 0° C. was added portionwise over 40 min a solution of the free-base of compound (31) (1.66 mmol) in dry dichloromethane (10 mL). After 20 min, a 5 mL aliquot of the reaction mixture was rapidly added to triethylamine (230 µL) and tert-amylamine (66 µL) and the resultant mixture was shaken at ambient temperature for 72 h. The reaction mixture was washed with 0.2N hydrochloric acid and the organics were loaded onto an SCX-2 (2 g) cartridge, then eluted with EtOAc followed by MeOH. The combined organics were concentrated in vacuo, then purified by flash column chromatography [SiO2; ethyl acetate:iso-hexane (30:70→50:50)] to afford the desired product as an orange oil (30 mg, 12%)

MS 455 [M+H]$^+$
LC (50/80) 92.3%, 7.22 min

Preparation of 2-(trifluoromethyl)-4'-methylbenzhydrol (149)

This material was prepared from 2-(trifluoromethyl)phenylmagnesium bromide (16 mmol) and p-tolualdehyde (1.82 mL, 15 mmol) using the procedure described for compound (96) (4.28 g, 100%).

LC (50/80) 97.1%, 4.76 min

Preparation of 1-benzhydryl-3-[2-(trifluoromethyl)-4'-methylbenzhydryloxy]azetidine (150)

This material was prepared from 1-benzhydryl-3-azetidinol (1) (7.5 mmol) and 2-(trifluoromethyl)-4'-methylbenzhydrol (149) (15 mmol) using the procedure described for compound (3). Flash column chromatography [SiO2; ethyl acetate-iso-hexane (5:95)] afforded a yellow gum (4.41 g) which was used in the next step without further purification.

Preparation of 3-[2-(trifluoromethyl)-4'-methylbenzhydryloxy]azetidine hydrochloride (151)

This material was prepared from 1-benzhydryl-3-[2-(trifluoromethyl)-4'-methylbenzyloxy]azetidine (150) (7.5 mmol) using the procedure described for compound (9). Crystallisation from DIPE-MeOH afforded the product as a white solid (1.39 g, 54%).

Example 116

3-[2-(trifluoromethyl)-4'-methylbenzhydryloxy]-N-(1-adamantyl)-azetidine-1-carboxamide (152)

This material was prepared from 3-[2-(trifluoromethyl)-4'-methylbenzhydryloxy]azetidine hydrochloride (151) (0.56 mmol) and 1-adamantyl isocyanate (0.56 mmol) using the procedure described for compound (10). The desired product was obtained as a white foam (264 mg, 94%).

NMR
LC (50/80) 98.1%, 8.20 min

Example 117

3-[2-(trifluoromethyl)-4'-methylbenzhydryloxy]-N-(tert-butyl)-azetidine-1-carboxamide (153)

This material was prepared from 3-[2-(trifluoromethyl)-4'-methylbenzhydryloxy]azetidine hydrochloride (151) (0.56 mmol) and tert-butyl isocyanate (0.56 mmol) using the procedure described for compound (10). The desired product was obtained as a colourless glass which gave a white solid on scratching (232 mg, 98%).

MS 420 [M+H]$^+$
LC (50/80) 98.7%, 6.54 min

Example 118

3-[2-(trifluoromethyl)-4'-methylbenzhydryloxy]-N-(cyclohexyl)-azetidine-1-carboxamide (154)

This material was prepared from 3-[2-(trifluoromethyl)-4'-methylbenzhydryloxy]azetidine hydrochloride (151) (0.56 mmol) and cyclohexyl isocyanate (0.56 mmol) using the procedure described for compound (10). The desired product was obtained as a white foam (230 mg, 91%).

MS 447 [M+H]$^+$
LC (50/80) 99.9%, 7.11 min

Preparation of 2-(trifluoromethyl)-4'-methoxybenzhydrol (155)

This material was prepared from 2-(trifluoromethyl)phenylmagnesium bromide (16 mmol) and p-anisaldehyde (1.86 mL, 15 mmol) using the procedure described for compound (96) (4.34 g, 100%).

LC (50/80) 97.2%, 3.62 min

Preparation of 1-benzhydryl-3-[2-(trifluoromethyl)-4'-methoxybenz-hydryloxy]azetidine (156)

This material was prepared from 1-benzhydryl-3-azetidinol (1) (7.5 mmol) and 2-(trifluoromethyl)-4'-methoxybenzhydrol (155) (15 mmol) using the procedure described for compound (3). Flash column chromatography [SiO2; ethyl acetate-iso-hexane (10:90→20:80)] afforded a pale yellow gum (2.73 g) which was used in the next step without further purification.

Preparation of 3-[2-(trifluoromethyl)-4'-methoxybenzhydryloxy]azetidine (157)

The corresponding hydrochloride salt was prepared from 1-benzhydryl-3-[2-(trifluoromethyl)-4'-methoxybenzyloxy] azetidine (156) (7.5 mmol) using the procedure described for compound (9). Due to the presence of impurities, the salt was partitioned between aqueous base and an organic solvent, the organic phase dried (MgSO4) and evaporated to afford the desired product as a colourless oil (730 mg, 29%).

Example 119

3-[2-(trifluoromethyl)-4'-methoxybenzhydryloxy]-N-(1-adamantyl)-azetidine-1-carboxamide (158)

To a solution of 3-[2-(trifluoromethyl)-4'-methoxybenzhydryloxy]azetidine (157) (100 mg, 0.30 mmol) in anhydrous DCM (4 mL) was added MP-carbonate (3.01 mmol/g; 100 mg, 0.30 mmol) and 1-adamantyl isocyanate (55 mg, 0.30 mmol). The resultant mixture was shaken at ambient temperature for 5 h, after which time it was poured onto a DCM-wetted SCX-2 (1 g) cartridge. Elution with DCM (6 mL) followed by DCM-MeOH (6 mL), then removal of solvent in vacuo afforded the desired product as a white foam (140 mg, 92%).

MS 515 [M+H]$^+$
LC (50/80) 97.9%, 7.86 min

Example 120

3-[2-(trifluoromethyl)-4'-methoxybenzhydryloxy]-N-(tert-butyl)-azetidine-1-carboxamide (159)

To a solution of 3-[2-(trifluoromethyl)-4'-methoxybenzhydryloxy]azetidine (157) (100 mg, 0.30 mmol) in anhydrous DCM (4 mL) was added MP-carbonate (3.01 mmol/g; 100 mg, 0.30 mmol) and tert-butyl isocyanate (35 µL, 0.30 mmol). The resultant mixture was shaken at ambient temperature for 5 h, after which time it was poured onto a DCM-wetted SCX-2 (1 g) cartridge. The sample was eluted with DCM (6 mL) followed by DCM-MeOH (6 mL), then evaporated. Purification by flash column chromatography [SiO$_2$; ethyl acetate-iso-hexane (35:65→50:50)] afforded the desired product as a colourless glass (90 mg, 70%).

MS 437 [M+H]$^+$
LC (50/80) 99.5%, 6.12 min

Preparation of 2-(trifluoromethyl)-4'-fluorobenzhydrol (160)

This material was prepared from 2-(trifluoromethyl)phenylmagnesium bromide (16 mmol) and 4-fluorobenzaldehyde (1.64 mL, 15 mmol) using the procedure described for compound (96) (4.27 g, 100%).

LC (50/80) 99.3%, 4.37 min

Preparation of 1-benzhydryl-3-[2-(trifluoromethyl)-4'-fluorobenzhydryloxy]azetidine (161)

This material was prepared from 1-benzhydryl-3-azetidinol (1) (7.5 mmol) and 2-(trifluoromethyl)-4'-fluorobenzhydrol (160) (15 mmol) using the procedure described for compound (3). After basic aqueous workup, the crude product was used in the next step without further purification.

Preparation of 3-[2-(trifluoromethyl)-4'-fluorobenzhydryloxy]azetidine hydrochloride (162)

This material was prepared from 1-benzhydryl-3-[2-(trifluoromethyl)-4'-fluorobenzyloxy]azetidine (161) (7.5 mmol) using the procedure described for compound (9). Crystallisation from DIPE-MeOH afforded the product as a white solid (1.49 g, 55%).

LC (50/80) 99.6%, 2.30 min

Example 121

3-[2-(trifluoromethyl)-4'-fluorobenzhydryloxy]-N-(1-adamantyl)-azetidine-1-carboxamide (163)

To a solution of 3-[2-(trifluoromethyl)-4'-fluorobenzhydryloxy]azetidine hydrochloride (162) (200 mg, 0.55 mmol) in anhydrous DCM (5 mL) was added MP-carbonate (3.01 mmol/g; 550 mg, 1.65 mmol) and 1-adamantyl isocyanate (101 mg, 0.55 mmol). The resultant mixture was shaken at ambient temperature for 16 h, after which time it was poured onto a DCM-wetted SCX-2 (1 g) cartridge. The sample was eluted with DCM (16 mL), then evaporated to afford the desired product as a white foam (257 mg, 92%).

MS 503 [M+H]$^+$
LC (50/80) 99.3%, 7.89 min

Example 122

3-[2-(trifluoromethyl)-4'-fluorobenzhydryloxy]-N-(tert-butyl)azetidine-1-carboxamide (164)

To a solution of 3-[2-(trifluoromethyl)-4'-fluorobenzhydryloxy]azetidine hydrochloride (162) (200 mg, 0.55 mmol) in anhydrous DCM (5 mL) was added MP-carbonate (3.01 mmol/g; 550 mg, 1.65 mmol) and tert-butyl isocyanate (65 µL, 0.55 mmol). The resultant mixture was shaken at ambient temperature for 16 h, after which time it was poured onto a DCM-wetted SCX-2 (1 g) cartridge. The sample was eluted with DCM (16 mL), then evaporated to afford the desired product as a colourless glass (204 mg, 87%).

MS 425 [M+H]$^+$
LC (50/80) 98.0%, 6.14 min

Example 123

3-[2-(trifluoromethyl)-4'-fluorobenzhydryloxy]-N-(cyclohexyl)-azetidine-1-carboxamide (165)

To a solution of 3-[2-(trifluoromethyl)-4'-fluorobenzhydryloxy]azetidine hydrochloride (162) (200 mg, 0.55 mmol) in anhydrous DCM (5 mL) was added MP-carbonate (3.01 mmol/g; 550 mg, 1.65 mmol) and cyclohexyl isocyanate (72 µL, 0.55 mmol). The resultant mixture was shaken at ambient temperature for 16 h, after which time it was poured onto a DCM-wetted SCX-2 (1 g) cartridge. The sample was eluted with DCM (16 mL), then evaporated to afford the desired product as a colourless glass (194 mg, 78%).

MS 451 [M+H]$^+$
LC (50/80) 99.8%, 6.82 min

Example 124

3-[2-(trifluoromethyl)-4'-chlorobenzhydryloxy]-N-(allyl)azetidine-1-carboxamide (166)

To a solution of 3-[2-(trifluoromethyl)-4'-chlorobenzhydryloxy]azetidine hydrochloride (98) (100 mg, 0.28 mmol) in anhydrous DCM (3 mL) was added MP-carbonate (3.01 mmol/g; 275 mg, 0.84 mmol) and allyl isocyanate (25 µL, 0.28 mmol). The resultant mixture was shaken at ambient temperature for 16 h, after which time it was poured onto a DCM-wetted SCX-2 (1 g) cartridge. The sample was eluted with DCM (18 mL), then evaporated to afford the desired product (72 mg, 61%).

MS 425 [M+H]$^+$
LC (50/80) 98.1%, 6.25 min

Example 125

3-[2-(trifluoromethyl)-4'-(methylthio)benzhydryloxy]-N-(1-adamantyl)azetidine-1-carboxamide (167)

To a solution of 3-[2-(trifluoromethyl)-4'-(methylthio)benzhydryloxy]azetidine hydrochloride (118) (100 mg, 0.26 mmol) in anhydrous DCM (5 mL) was added MP-carbonate (3.10 mmol/g; 250 mg, 0.84 mmol) and 1-adamantyl isocyanate (47 mg, 0.26 mmol). The resultant mixture was shaken at ambient temperature for 16 h, after which time it was poured onto a DCM-wetted SCX-2 (1 g) cartridge. The sample was eluted with DCM (18 mL), then evaporated to afford the desired product as a white, crystalline solid (70 mg, 51%).

MS 531 [M+H]$^+$

LC (50/80) 93.3%, 8.56 min

Example 126

3-[2-(trifluoromethyl)-4'-(methylthio)benzhydryloxy]-N-(cyclo-hexyl)azetidine-1-carboxamide (168)

To a solution of 3-[2-(trifluoromethyl)-4'-(methylthio) benzhydryloxy]azetidine hydrochloride (118) (100 mg, 0.26 mmol) in anhydrous DCM (5 mL) was added MP-carbonate (3.10 mmol/g; 250 mg, 0.84 mmol) and cyclohexyl isocyanate (33 µL, 0.26 mmol). The resultant mixture was shaken at ambient temperature for 16 h, after which time it was poured onto a DCM-wetted SCX-2 (1 g) cartridge. The sample was eluted with DCM (18 mL), then evaporated to afford the desired product as a white, crystalline solid (65 mg, 52%).

MS 479 [M+H]$^+$

LC (50/80) 96.8%, 7.46 min

Preparation of 2-(trifluoromethyl)-4'-(methylsulfonyl)benzhydrol (169)

This material was prepared from 2-(trifluoromethyl)phenylmagnesium bromide (14.5 mmol) and 4-(methylsulfonyl) benzaldehyde (2.68 g, 13.8 mmol) using the procedure described for compound (96). The product was obtained as an amber gum (4.95 g, 100%).

LC (80/20) 98.9%, 0.46 min

Preparation of 1-benzhydryl-3-[2-(trifluoromethyl)-4'-(methylsulfonyl)benzhydryloxy]azetidine (170)

This material was prepared from 1-benzhydryl-3-azetidinol (1) (6.9 mmol) and 2-(trifluoromethyl)-4'-(methylsulfonyl)benzhydrol (169) (13.8 mmol) using the procedure described for compound (3). After basic aqueous workup, the crude product was partially purified by flash column chromatography [SiO2; ethyl acetate-iso-hexane (30:70→80:20)] to afford an off-white foam (1.69 g) which was used directly in the next step without further purification.

Preparation of 3-[2-(trifluoromethyl)-4'-(methylsulfonyl)benzhydryloxy]azetidine (171)

This material was prepared from 1-benzhydryl-3-[2-(trifluoromethyl)-4'-(methylsulfonyl)benzhydryloxy]azetidine (170) (6.9 mmol) using the procedure described for compound (4). After basic aqueous workup, purification by flash column chromatography [SiO$_2$; ethyl acetate-methanol (90: 10)→ethyl acetate-methanol—ammonium hydroxide (90:10:5)] afforded the desired product as a pale yellow oil (234 mg, 9% over 2 steps).

MS 386 [M+H]$^+$

LC (50/80) 89.8%, 6.49 min

Example 127

3-[2-(trifluoromethyl)-4'-(methylsulfonyl)benzhydryloxy]-N-(tert-butyl)azetidine-1-carboxamide (172)

To a solution of 3-[2-(trifluoromethyl)-4'-(methylsulfonyl) benzhydryloxy]azetidine (171) (222 mg, 0.58 mmol) in anhydrous DCM (7 mL) was added molecular sieves and tert-butyl isocyanate (68 µL, 0.58 mmol). After shaking at ambient temperature for 16 h, the mixture was poured onto a DCM-wet SCX-2 cartridge (2 g). Elution with DCM (24 mL) and evaporation afforded the desired product as a pale yellow solid (188 mg, 67%).

MS 485 [M+H]$^+$

LC (50/80) 97.6%, 4.16 min

Preparation of 2-(trifluoromethyl)-4'-(difluoromethoxy)benzhydrol (173)

This material was prepared from 2-(trifluoromethyl)phenylmagnesium bromide (16 mmol) and 4-(difluoromethoxy) benzaldehyde (2.09 mL, 15 mmol) using the procedure described for compound (96). The product was obtained as an amber gum (3.05 g, 64%).

LC (80/20) 97.6%, 0.59 min

Preparation of 1-benzhydryl-3-[2-(trifluoromethyl)-4'-(difluoromethoxy)-benzhydryloxy]azetidine (174)

This material was prepared from 1-benzhydryl-3-azetidinol (1) (1.12 g, 4.7 mmol) and 2-(trifluoromethyl)-4'-(difluoromethoxy)benzhydrol (173) (3.0 g, 9.4 mmol) using the procedure described for compound (3). After basic aqueous workup, the crude product was partially purified by flash column chromatography [SiO$_2$; ethyl acetate-iso-hexane (10: 90-+15:85)] to afford an amber gum (2.83 g) which was used directly in the next step without further purification.

Preparation of 3-[2-(trifluoromethyl)-4'-(difluoromethoxy)benzhydryloxy]azetidine hydrochloride (175)

To a stirred solution of 1-benzhydryl-3-[2-(trifluoromethyl)-4'-(difluoro-methoxy)benzhydryloxy]azetidine (174) (2.73 g from previous step-assumed 4.7 mmol) in DCM (40 mL), cooled in ice-water bath, was added 1-chloroethyl chloroformate (1 mL, 9.4 mmol). After 1 h, the mixture was allowed to warm to ambient temperature. After a further 5.5 h, the mixture was concentrated under reduced pressure, methanol (40 mL) was added, and the mixture was stirred for 16 h. The mixture was concentrated under reduced pressure, then dissolved in iso-hexane (4 mL)-DIPE (30 mL)-MeOH (2 mL). Upon stirring, a precipitate formed. The mixture was cooled in ice-water bath for 15 min.

Filtration and washing with ice-cold DIPE-iso-hexane (1:1) afforded the desired product as a white solid (920 mg, 48% over 2 steps).

MS 374 [M+H]$^+$

LC (50/80) 98.5%, 3.54 min

Example 128

3-[2-(trifluoromethyl)-4'-(difluoromethoxy)benzhydryloxy]-N-(tert-butyl)azetidine-1-carboxamide (176)

To a solution of 3-[2-(trifluoromethyl)-4'-(difluoromethoxy)benzhydryloxy]azetidine hydrochloride (175) (100 mg, 0.24 mmol) in anhydrous DCM (4 mL) was added MP-carbonate (2.62 mmol/g; 280 mg, 0.72 mmol), molecular sieves and tert-butyl isocyanate (29 µL, 0.24 mmol). After shaking at ambient temperature for 2 h, the mixture was poured onto a DCM-wet SCX-2 cartridge (2 g). Elution with DCM (20 mL) and evaporation afforded the desired product (90 mg, 78%).

MS 473 [M+H]$^+$
LC (50/80) 96.5%, 6.34 min

Example 129

3-[2-(trifluoromethyl)-4'-(difluoromethoxy)benzhydryloxy]-N-(sec-butyl)azetidine-1-carboxamide (177)

To a solution of 3-[2-(trifluoromethyl)-4'-(difluoromethoxy)benzhydryloxy]azetidine hydrochloride (175) (100 mg, 0.24 mmol) in anhydrous DCM (4 mL) was added MP-carbonate (2.62 mmol/g; 280 mg, 0.72 mmol), molecular sieves and sec-butyl isocyanate (29 µL, 0.24 mmol). After shaking at ambient temperature for 2 h, the mixture was poured onto a DCM-wet SCX-2 cartridge (2 g). Elution with DCM (20 mL) and evaporation afforded the desired product (81 mg, 70%).

MS 473 [M+H]$^+$
LC (50/80) 99.8%, 6.17 min

Example 130

3-[2-(trifluoromethyl)-4'-(difluoromethoxy)benzhydryloxy]-N-(iso-propyl)azetidine-1-carboxamide (178)

To a solution of 3-[2-(trifluoromethyl)-4'-(difluoromethoxy)benzhydryloxy]azetidine hydrochloride (175) (100 mg, 0.24 mmol) in anhydrous DCM (4 mL) was added MP-carbonate (2.62 mmol/g; 280 mg, 0.72 mmol), molecular sieves and iso-propyl isocyanate (25 µL, 0.24 mmol). After shaking at ambient temperature for 2 h, the mixture was poured onto a DCM-wet SCX-2 cartridge (2 g). Elution with DCM (20 mL) and evaporation afforded the desired product (74 mg, 66%).

MS 459 [M+H]$^+$
LC (50/80) 99.8%, 5.79 min

Example 131

3-[2-(trifluoromethyl)-4'-(difluoromethoxy)benzhydryloxy]-N-(cyclohexyl)azetidine-1-carboxamide (179)

To a solution of 3-[2-(trifluoromethyl)-4'-(difluoromethoxy)benzhydryloxy]azetidine hydrochloride (175) (100 mg, 0.24 mmol) in anhydrous DCM (4 mL) was added MP-carbonate (2.62 mmol/g; 280 mg, 0.72 mmol), molecular sieves and cyclohexyl isocyanate (32 µL, 0.24 mmol). After shaking at ambient temperature for 2 h, the mixture was poured onto a DCM-wet SCX-2 cartridge (2 g). Elution with DCM (20 mL) and evaporation afforded the desired product (91 mg, 75%).

MS 499 [M+H]$^+$
LC (50/80) 97.0%, 5.63 min

Example 132

3-[2-(trifluoromethyl)-4'-(difluoromethoxy)benzhydryloxy]-N-(allyl)azetidine-1-carboxamide (180)

To a solution of 3-[2-(trifluoromethyl)-4'-(difluoromethoxy)benzhydryloxy]azetidine hydrochloride (175) (100 mg, 0.24 mmol) in anhydrous DCM (4 mL) was added MP-carbonate (2.62 mmol/g; 280 mg, 0.72 mmol), molecular sieves and allyl isocyanate (22 µL, 0.24 mmol). After shaking at ambient temperature for 2 h, the mixture was poured onto a DCM-wet SCX-2 cartridge (2 g). Elution with DCM (20 mL) and evaporation afforded the desired product (68 mg, 61%).

MS 457 [M+H]$^+$
LC (50/80) 100.0%, 6.90 min

Example 133

3-[2-(trifluoromethyl)-4'-fluorobenzhydryloxy]-N-(sec-butyl)azetidine 1-carboxamide (181)

To a solution of 3-[2-(trifluoromethyl)-4'-fluorobenzhydryloxy]azetidine hydrochloride (162) (150 mg, 0.42 mmol) in anhydrous DCM (4 mL) was added MP-carbonate (2.62 mmol/g; 475 mg, 1.26 mmol), molecular sieves and sec-butyl isocyanate (49 µL, 0.42 mmol). The resultant mixture was shaken at ambient temperature for 16 b, after which time it was poured onto a DCM-wetted SCX-2 (1 g) cartridge. The sample was eluted with DCM (24 mL), then evaporated to afford the desired product as a colourless gum (135 mg, 77%).

MS 425 [M+H]$^+$
LC (50/80) 99.0%, 6.21 min

Example 134

3-[2-(trifluoromethyl)-4'-fluorobenzhydryloxy]-N-(iso-propyl)-azetidine-1-carboxamide (182)

To a solution of 3-[2-(trifluoromethyl)-4'-fluorobenzhydryloxy]azetidine hydrochloride (162) (150 mg, 0.42 mmol) in anhydrous DCM (4 mL) was added MP-carbonate (2.62 mmol/g; 475 mg, 1.26 mmol), molecular sieves and iso-propyl isocyanate (42 µL, 0.42 mmol). The resultant mixture was shaken at ambient temperature for 16 h, after which time it was poured onto a DCM-wetted SCX-2 (1 g) cartridge. The sample was eluted with DCM (24 mL), then evaporated to afford the desired product as a colourless glass which gave a white solid on scratching (126 mg, 74%).

MS 411 [M+H]$^+$
LC (50/80) 98.9%, 5.77 min

Example 135

3-[2-(trifluoromethyl)-4'-fluorobenzhydryloxy]-N-[(S)-α-methyl-benzyl]azetidine-1-carboxamide (183)

To a solution of 3-[2-(trifluoromethyl)-4'-fluorobenzhydryloxy]azetidine hydrochloride (162) (150 mg, 0.42 mmol) in anhydrous DCM (4 mL) was added MP-carbonate (2.62 mmol/g; 475 mg, 1.26 mmol), molecular sieves and (S)-α- methylbenzyl isocyanate (60 µL, 0.42 mmol). The resultant mixture was shaken at ambient temperature for 16 h, after which time it was poured onto a DCM-wetted SCX-2 (1 g) cartridge. The sample was eluted with DCM (24 mL), then evaporated to afford the desired product as a colourless glass which gave a white solid on scratching (136 mg, 69%).

MS 473 [M+H]$^+$

LC (50/80) 99.0%, 6.93 min

Example 136

3-[2-(trifluoromethyl)-2'-fluoro-4'-(1-piperidinyloxomethyl)-benzhydryloxy]-N-(tert-butyl)azetidine-1-carboxamide (184) and Example 137

3-[2-(trifluoromethyl)-2'-fluorobenzhydryloxy]-N-(tert-butyl)azetidine-1-carboxamide (185)

A mixture of 3-[2-(trifluoromethyl)-2'-fluoro-4'-bromobenzhydryloxy]-N-(tert-butyl)-azetidine-1-carboxamide (115) (106 mg, 0.21 mmol), diglyme (1 mL), 4M K$_2$CO$_3$ (0.2 mL), toluene (1 mL), (R/S)-BINAP (12.1 mg), Herrmann's catalyst [CAS: 172418-32-5] (7.0 mg), Mo(CO)$_6$ (26.0 mg) and piperidine (27 µL) was irradiated, with stirring, in a microwave reactor. Power was applied and varied to maintain the reaction at a temperature of 150° C. for a period of 15 min. After this time, the reaction was allowed to cool, then was filtered and evaporated. Purification by flash column chromatography [SiO$_2$; ethyl acetate-iso-hexane (30:70→70:30)] afforded 3-[2-(trifluoromethyl)-2'-fluoro-4'-(1-piperidinyloxomethyl)benzhydryloxy]-N-(tert-butyl)azetidine-1-carboxamide (184) as a pale yellow solid (13.2 mg, 12%)

MS 536 [M+H]$^+$

LC 69.3%, 5.69 min and 3-[2-(trifluoromethyl)-2'-fluorobenzhydryloxy]-N-(tert-butyl)azetidine-1-carboxamide (185) as a pale yellow gum (16.2 mg, 18%)

MS 425 [M+H]$^+$

LC 61.9%, 6.08 min

Example 138

3-[(S*)-2-(trifluoromethyl)-4'-chlorobenzhydryloxy]-N-(tert-butyl)-azetidine-1-carboxamide (186) and Example 139

3-[(R*)-2-(trifluoromethyl)-4'-chlorobenzhydryloxy]-N-(tert-butyl)-azetidine-1-carboxamide (187)

The racemic compound 3-[2-(trifluoromethyl)-4'-chlorobenzhydryloxy]-N-(tert-butyl)azetidine-1-carboxamide (99) was separated into samples which were significantly enriched in each single enantiomeric form. Thus, a sample of the racemic mixture (300 mg) was dissolved in 6 mL of an IPA-hexane (10:90) mix. This mixture was repeatedly injected (11×500 µL) onto a Daicel Chiralpak® AD™ chiral HPLC column (250 mm×21 mm ID) fitted with a guard column (50 mm×21 mm ID) [eluent: IPA-hexane (10:90); flow-rate: 10 mL/min; wavelength: 235 nm]. The combined first-eluting enantiomer (arbitrarily assigned S* unknown absolute stereochemistry) fractions were evaporated to afford 3-[(S*)-2-(trifluoromethyl)-4'-chlorobenzhydryloxy]-N-(tert-butyl)azetidine-1-carboxamide (186) as a white solid (103.5 mg, 37.6%).

MS 441 [M+H]$^+$

LC (50/80) 98.8%, 7.08 min

LC [Chiral AD; IPA-hexane (10:90)] 97.3%, 7.90 min; 100% ee

Mixed fractions were evaporated to afford a white solid (59.8 mg, 21.7%).

The combined second-eluting enantiomer (arbritrarily assigned R* unknown absolute stereochemistry) fractions) were evaporated to afford 3-[(S*)-2-(trifluoromethyl)-4'-chlorobenzhydryloxy]-N-(tert-butyl)azetidine-1-carboxamide (187) as a white solid (70.0 mg, 25.5%).

MS 441 [M+H]$^+$

LC (50/80) 98.7%, 7.06 min

LC [Chiral AD; IPA-hexane (5:95)] 88.5%, 16.46 min; 9.2%, 14.27 min; 81% ee

Example 139a

3-[(R*)-2-(trifluoromethyl)-4'-chlorobenzhydryloxy]-N-(tert-butyl)-azetidine-1-carboxamide (187)

Compound 187 of example 139 can also be prepared using the protocols described in Examples 154 and 155. These examples describe protocols for the resolution of starting materials related to the starting materials of the compound of this example. Use of these protocols can result in a pure enantiomeric form of the compound of this example.

3-[(4-Chloro)phenyl-(2-trifluoromethyl)phenyl]methoxyazetidine hydrochloride (98) (56.1 g, 148.3 mmol) was converted to the free base by dissolution in water (450 mL) and ice (150 g). The suspension was stirred for 5 min and sinter filtered to remove small amounts of contaminating bis[(4-chloro)phenyl-(2-trifluoromethyl)phenyl]methyl ether. The aqueous phase was treated with further ice (140 g) and basified with aqueous sodium hydroxide (5N, 30 mL). The mixture was extracted with dichloromethane (500 mL+250 mL), and the combined extracts were washed with water (500 mL) and concentrated in vacuo to give the free base 3-[(4-chloro) phenyl-(2-trifluoromethyl)phenyl]methoxyazetidine (98), as an orange oil (48.62 g, 142.26 mmol, 96%).

D-Tartaric acid (21.35 g, 142.25 mmol) was suspended in 2-propanol (430 mL) and the suspension was heated to 80° C. After the solution had cooled to 60° C. a solution of 3-[(4-chloro)phenyl-(2-trifluoromethyl)phenyl]methoxyazetidine (48.62 g, 142.26 mmol) in dichloromethane (400 mL) was poured in, dropping funnel washed dichloromethane (30 mL). The solution was concentrated in vacuo to give an orange foam (112.6 g). 2-Propanol (750 mL) and ethyl acetate (500 mL) were heated separately to 70° C. and added to the foam. The crystallising D-tartrate was heated from 55° C. to 75° C. over 30 min with a hot air gun, and allowed to cool with stirring for 2 h, then stirred at 0° C. for 1 h. The crystals were collected, washed with 2-propanol:ethyl acetate, 1:1 (200 mL), and dried in air overnight to give (R)-3-[(4-chloro) phenyl-(2-trifluoromethyl)phenyl]methoxyazetidine (210) (23.78 g, 34% (50% maximum)) as the batch 1 D-tartrate.

LC-(Chiral AD; hexane:2-propanol, 90:10) 91.65% at 8.20 min and 6.0% at 7.36 min (87.6% ee).

The batch 1 D-tartrate (210) (16.01 g, 325.5 mmol) was recrystallised from hot ethanol (320 mL) and allowed to crystallise overnight. The colourless needles were collected, washed with ethanol (50 mL) and dried in air for 3 h, to give further enriched compound (210) batch 2 D-tartrate (13.80 g, 86%). The recrystallisation was repeated with ethanol (280 mL), and the crystals were collected, washed, and dried to give batch 3 D-tatrate (210) 12.49 g (78% over two steps).

LC (50/80) 99.86% at 3.43 min.

Batch 3 D-tartrate (210) (11.984 g, 24.365 mmol) was suspended in a mixture of water (100 mL) and dichloromethane (100 mL). The suspension was basified with 5 N aqueous sodium hydroxide (15 mL) and the layers were separated. The aqueous phase was re-extracted with dichloromethane (25 mL), and the combined organic phases were washed with water (100 mL) and concentrated in vacuo to give (R)-3-[(4-chloro)phenyl-(2-trifluoromethyl)phenyl]methoxyazetidine (210) (8.40 g) as the free base and as a colourless oil.

This material could also be used to make compound (187) using the procedure already described in Example 139, but with higher enantiomeric excess.

Analysis of compound 187 from this resolution method:

MS 441 [M+H]$^+$

LC (80/20 isocratic) 99.6%, 1.02 min

LC (Chiral AD; hexane:2-propanol, 90:10) 0.33% at 7.42 min and 97.63% at 8.28 min (99.32% ee).

Example 140

3-[(S*)-2-(trifluoromethyl)-4'-(methylsulphonyl)benzhydryloxy]-N-(tert-butyl)azetidine-1-carboxamide (188) and

Example 141

3-[(R*)-2-(trifluoromethyl)-4'-(methylsulphonyl)benzhydryloxy]-N-(tert-butyl)azetidine-1-carboxamide (189)

The racemic compound 3-[2-(trifluoromethyl)-4'-(methylsulfonyl)benzhydryloxy]-N-(tert-butyl)azetidine-1-carboxamide (172) was separated into samples which were significantly enriched in each single enantiomeric form. Thus, a sample of the racemic mixture (87 mg) was dissolved in 800 μL of an PA-hexane (25:75) mix. This mixture was repeatedly injected (5×50 μL) onto a Daicel Chiralpak® AD™ chiral HPLC column (250 mm×21 mm ID) fitted with a guard column (50 mm×21 mm ID) [eluent:IPA-hexane (25:75); flow-rate: 15 mL/min; wavelength: 235 nm]. The combined first-eluting enantiomer (arbitrarily assigned S* unknown absolute stereochemistry) fractions) were evaporated to afford 3-[(S*)-2-(trifluoromethyl)-4'-(methylsulfonyl)benzhydryloxy]-N-(tert-butyl)-azetidine-1-carboxamide as a white solid.

MS 485 [M+H]$^+$

LC (50/80) 99.9%, 3.97 min

LC [Chiral AD; IPA-hexane (30:70)] 97.1%, 7.59 min; 100% ee

The combined second-eluting enantiomer (arbitrarily assigned R* unknown absolute stereochemistry) fractions) were evaporated to afford 3-[(R*)-2-(trifluoromethyl)-4'-(methylsulfonyl)benzhydryloxy]-N-(tert-butyl)azetidine-1-carboxamide as a white solid.

MS 485 [M+H]$^+$

LC (50/80) 99.6%, 4.02 min

LC [Chiral AD; IPA-hexane (30:70)] 81.8%, 11.6 min; 11.1%, 7.74 min; 76% ee

Preparation of 3-[(4-iodo)phenyl-2-(trifluoromethyl)phenyl]methoxyazetidine (190)

3-[(4-iodo)phenyl-2-(trifluoromethyl)phenyl]methoxyazetidine (190) was prepared using a similar procedure to that described for compound 4.

?max (diffuse reflectance, KBr)/cm$^{-1}$; 3451, 2922, 2464, 1906, 1579, 1484, 1451, 1383, 1356, 1313, 1167, 1128, 1059, 1038, 1006, 950, 892, 876, 822, 795, 770, 662, 635, 626, 599, 486, 469.

NMR (400 MHz, d$^6$-DMSO) δ$_H$ 3.17 (1H, s), 3.77 (1H, q, J 5.6 Hz), 4.00-3.90 (3H, m), 4.39 (1H, pent, J 6.3 Hz), 5.80 (1H, s), 7.11 (2H, d, J 8.1 Hz), 7.58 (1H, t, J 7.1 Hz), 7.78-0.769 (5H, m), 9.12-8.98 (2H, br s).

Example 142

Preparation of 3-[(4-iodo)phenyl-2-(trifluoromethyl)phenyl]methoxy-N-(tert-butyl)azetidine-1-carboxamide (191)

3-[(4-iodo)phenyl-2-(trifluoromethyl)phenyl]methoxy-N-(tert-butyl)azetidine 1-carboxamide (191) was prepared using a similar procedure to that described for compound 5.

MS 533 [M+H]$^+$

NMR (400 MHz, d$^6$-DMSO) δ$_H$ 1.20 (9H, s), 3.52 (1H, dd, J 9.0,4.5 Hz), 3.64 (1H, dd, J 8.8, 4.3 Hz), 3.81 (1H, dd, J 8.8, 6.6 Hz), 3.87 (1H, dd, J 8.8, 6.5 Hz), 4.26-4.20 (1H, m), 5.65 (1H, s), 5.69 (1H, s), 7.09 (2H, d, J 8.4 Hz), 7.56 (1H, dt, J 8.2, 2.1 Hz), 7.77-7.71 (5H, m).

Example 143

3-[4-(carboxamide)phenyl-2-(trifluoromethyl)phenyl]methoxy-N-(tert-butyl)azetidine-1-carboxamide (192)

Carbon monoxide was passed through a solution of the aryl iodide (191) (100 mg, 0.19 mmol), palladium acetate (4 mg, 0.019 mmol), triphenylphosphine (10 mg, 0.38 mmol), tetraethylammonium chloride (31 mg, 0.19 mmol) and potassium carbonate (261 mg, 1.9 mmol) in toluene (6 mL) for 20 minutes. Ammonium chloride (41 mg, 0.76 mmol) was added and the tube sealed and heated to 110° C. for 17 h. The reaction mixture was cooled to room temperature, the solids were filtered and the organic phase washed with water (20 mL) and brine (20 mL), dried (Na$_2$SO$_4$), filtered and the solvent removed under reduced pressure to afford the crude product. Purification by preparative HPLC gave the title compound (192) as a white solid (7.7 mg, 9% yield).

MS 450 [M+H]$^+$

LC (50/80) 99.3%, 3.52 min.

Example 144

3-[4-(2-thiophenyl)phenyl-2-(trifluoromethyl)phenyl]methoxy-N-(tert-butyl)azetidine-1-carboxamide (193)

To a solution of aryl iodide (191) (100 mg, 0.19 mmol), 2-thiopheneboronic acid (48 mg, 0.38 mmol), palladium acetate (4 mg, 0.019 mmol) and triphenylphosphine (10 mg, 0.38 mmol) in tetrahydrofuran (10 mL) was added sodium bicarbonate (10 mL, saturated aqueous). The reaction mixture was heated to reflux (65° C.) for 4 h, cooled, filtered and partitioned between water (20 mL) and ethyl acetate (20 mL). The organic phase was separated and washed with brine (20 mL), dried (Na$_2$SO$_4$), filtered and the solvent removed under reduced pressure to afford the crude product, as a brown oil. Purification by silica gel chromatography (20% ethyl acetate/iso-hexane eluant) gave the title compound (193) as a brown solid (67.2 mg, 73% yield).

MS 489 [M+H]$^+$

LC (50/80) 94.1%, 7.99 min.

Example 145

3-[4-(3-pyridinyl)phenyl-2-(trifluoromethyl)phenyl]methoxy-N-(tert-butyl)azetidine-1-carboxamide (194)

To a solution of aryl iodide (191) (100 mg, 0.19 mmol), pyridine-3-boronic acid 1,3-propanediol cyclic ester (61 mg, 0.38 mmol), palladium acetate (4 mg, 0.019 mmol) and triphenylphosphine (10 mg, 0.38 mmol) in tetrahydrofuran (10 mL) was added sodium bicarbonate (10 mL, saturated aqueous). The reaction mixture was heated to reflux (65° C.) for 4 h, cooled, filtered and partitioned between water (20 mL) and ethyl acetate (20 mL). The organic phase was separated and washed with brine (20 mL), dried (Na$_2$SO$_4$), filtered and the solvent removed under reduced pressure to afford the crude product as a yellow oil. Purification by silica gel chromatography (50% ethyl acetate/iso-hexane eluant) followed by preparative HPLC gave the title compound (194) as a colourless gum (7.7 mg, 8.5% yield).

MS 484 [M+H]$^+$

LC (50/80) 99.2%, 6.01 min.

Preparation of 3-[4-(chloromethyl)phenyl-2-(trifluoromethyl)phenyl]methoxy-N-(tert-butyl)azetidine-1-carboxamide (195)

3-[4-(chloromethyl)phenyl-2-(trifluoromethyl)phenyl]methoxy-N-(tert-butyl)azetidine-1-carboxamide (195) was prepared using a similar procedure to that described for compound 5.

MS 455/457 [M+H]$^+$

NMR (400 MHz, CDCL$_3$) $\delta_H$ 1.31 (9H, s), 3.74 (1H, dd, J 8.8, 4.8 Hz), 3.90-3.82 (3H, m), 3.99 (1H, dd, J 7.8, 6.5 Hz), 4.32-4.26 (1H, m), 4.55 (2H, s), 5.78 (1H, s), 7.35-7.29 (4H, m), 7.42 (1H, t, J 7.8 Hz), 7.56 (1H, t, J 7.2 Hz), 7.68-7.63 (2H, t, J 11.2, 7.8 Hz).

Example 146

3-[4-(morpholin-4-ylmethyl)phenyl-2-(trifluoromethyl)phenyl]methoxy-N-(tert-butyl)azetidine-1-carboxamide (196)

The benzyl chloride (195) (40 mg, 0.088 mmol) and morpholine (3 mL, 31 mmol) were heated to 50° C. for 18 h. The reaction mixture was cooled, excess amine was removed under reduced pressure and the residue partitioned between ethyl acetate and sodium hydroxide (1M). The organic phase was washed with water (2×20 mL) and brine (20 mL), dried (Na$_2$SO$_4$), filtered and the solvent removed under reduced pressure to afford the crude product. Purification by SCX-2 cartridge afforded the title compound (196) as a white solid (31 mg, 70% yield).

MS 506 [M+H]$^+$

LC (50/80) 96.9%, 6.24 min.

Example 147

3-[4-(cyclopropylmethylaminomethyl)phenyl-2-(trifluoromethyl)phenyl]methoxy-N-(tert-butyl)azetidine-1-carboxamide (197)

The benzyl chloride (195) (34 mg, 0.075 mmol) and cyclopropylmethylamine (1 mL, 12 mmol) were heated to 50° C. for 18 h. The reaction mixture was cooled, excess amine was removed under reduced pressure and the residue partitioned between ethyl acetate and sodium hydroxide (1M). The organic phase was washed with water (2×20 mL) and brine (20 mL), dried (Na$_2$SO$_4$), filtered and the solvent removed under reduced pressure to afford the crude product. Purification by SCX-2 cartridge afforded the title compound (197) as a colourless gum (36 mg, 98% yield).

MS 490 [M+H]$^+$

LC (50/80) 94.7%, 4.24 min.

Preparation of 3-[(4-bromo)phenyl-2-(trifluoromethyl)phenyl]methoxyazetidine (198)

The hydrochloride salt of 3-[(4-bromo)phenyl-2-(trifluoromethyl)phenyl]methoxyazetidine (198) was prepared using a procedure similar to that described for compound 4.

Compound (198) (9.15 g, 21.65 mmol) was dissolved in water (100 mL), and the solution was basified with 5N aqueous sodium hydroxide (6 mL). The suspension was extracted with dichloromethane (100 mL+50 mL), and the extracts were washed with water (100 mL) and concentrated in vacuo to give the free base (198) (8.55 g, 102%), as a yellow oil.

MS 386/388 [M+H]$^+$

?max (diffuse reflectance, KBr)/cm$^{-1}$; 3450, 2923, 2630, 2462, 1904, 1574, 1487, 1451, 1384, 1356, 1312, 1251, 1166, 1127, 1072, 1038, 1024, 1010, 960, 893, 876, 821, 797, 771, 662, 636, 626, 598, 490, 470.

Example 148

3-[(4-bromo)phenyl-(2-trifluoromethyl)phenyl]methoxy-N-tert-butyl-azetidine-1-carboxamide (199)

3-[(4-bromo)phenyl-(2-trifluoromethyl)phenyl]methoxy-N-tert-butyl-azetidine-1-carboxamide (199) was prepared using a procedure similar to that described for compound 5.

MS 485/487 [M+H]$^+$

?max (diffuse reflectance, KBr)/cm$^{-1}$; 3316, 3066, 2967, 1643, 1536, 1311, 1121, 1036, 1010, 960, 849, 800, 768, 658, 635, 560, 485.

Example 149

3-[(4-(4-pyridyl)phenyl)-(2-trifluoromethyl)phenyl]methoxy-N-tert-butyl-azetidine-1-carboxamide (200)

To a solution of compound [3-[(4-bromo)phenyl-(2-trifluoromethyl)phenyl]methoxy-N-tert-butyl-azetidine-1-carboxamide] (199) (0.12 g, 0.25 mmol) and pyridin-4-yl boronic acid (0.039 g, 0.31 mmol), in ethylene glycol dimethyl ether (1.17 mL), ethanol (0.33 mL) and sodium carbonate (2M aqueous solution, 0.5 mL) was added bis(triphenylphosphine) palladium (II) chloride (0.009 g). The resultant mixture was heated in a microwave reactor at 125° C. for 5 mins. The reaction mixture was allowed to cool to room temperature and poured into water. The mixture was extracted with EtOAc (2×10 mL) and combined organic layers washed with brine, dried (MgSO$_4$), filtered and concentrated under reduced pressure. Purification by silica gel chromatography (70% ethyl acetate/iso-hexane to 100% ethyl acetate as eluant) gave the title compound (200) as a white solid (0.087 g).

MS 484 [M+H]$^+$

LC (50/80) 88.24%, 6.91 min.

Example 150

3-[(4-(2,4-dihydroxypyrimid-5-yl)phenyl)-(2-trifluoromethyl)phenyl]methoxy-N-tert-butyl-azetidine-1-carboxamide (201)

To a solution of compound (199) (0.10 g, 0.20 mmol) and 2,4-di(tert-butoxy)pyrimid-5-yl boronic acid (0.039 g, 0.31 mmol), in ethylene glycol dimethyl ether (1.17 mL), ethanol (0.33 mL) and sodium carbonate (2M aqueous solution, 0.5 mL) was added bis(triphenylphosphine) palladium (II) chloride (0.007 g). The resultant mixture was heated in a microwave reactor at 125° C. for 5 mins. The reaction mixture was allowed to cool to room temperature and poured into water. The mixture was extracted with EtOAc and washed with brine, dried (MgSO$_4$), filtered and concentrated under reduced pressure. Purification by silica gel chromatography (70% ethyl acetate/iso-hexane to 100% ethyl acetate as eluant) gave an impure residue that was further columned twice (silica gel), the first in 2% methanol/ethyl acetate and the second in ethyl acetate to yield the title compound (201) as an off-white solid (0.031 g).

MS 517 [M+H]$^+$ 515 [M−H]$^-$

?max (diffuse reflectance, KBr)/cm$^{-1}$; 2964, 1670, 1516, 1312, 1160, 1122, 769, 662, 545.

Example 151

3-[(4-(2-phenyl-ethenyl)phenyl)-(2-trifluoromethyl)phenyl]methoxy-N-tert-butyl-azetidine-1-carboxamide (202)

To a solution of compound (199) (0.10 g, 0.20 mmol) and styryl boronic acid (0.039 g, 0.31 mmol), in ethylene glycol dimethyl ether (1.17 mL), ethanol (0.33 mL) and sodium carbonate (2M aqueous solution, 0.5 mL) was added bis(triphenylphosphine) palladium (II) chloride (0.007 g). The resultant mixture was heated in a microwave reactor at 125° C. for 5 mins. The reaction mixture was allowed to cool to room temperature and poured into water. The mixture was extracted with EtOAc and washed with brine, dried (MgSO$_4$), filtered and concentrated under reduced pressure. Purification by silica gel chromatography (70% ethyl acetate/iso-hexane as eluant) gave an impure residue that was further purified using preparative HPLC to yield the title compound (202) as an off-white solid (0.037 g).

MS 509 [M+H]$^+$ 507 [M−H]$^-$

LC (50/80) 98.7% 8.48 min.

Example 152

Preparation of 3-[(2-(trifluoromethyl)phenyl-4'-(methoxycarbonyl)phenyl]methoxy-N-tert-butyl-azetidine-1-carboxamide (203)

3-[(2-(trifluoromethyl)phenyl-4'-(methoxycarbonyl)phenyl]methoxy-N-tert-butyl-azetidine-1-carboxamide (203) was prepared according to the method for compound (5).

MS 465 [M+H]$^+$

?max (diffuse reflectance, KBr)/cm$^{-1}$; 3320, 2958, 1724, 1651, 1537, 1435, 1393, 1364, 1314, 1281, 1218, 1163, 1123, 1037, 1020, 910, 770, 734, 660.

Example 153

Preparation of 3-[(2-(trifluoromethyl)phenyl-4'-(carboxyl)phenyl]methoxy-N-tert-butyl-azetidine-1-carboxamide (204)

To a stirred solution of (203) (0.3 g, 0.64 mmol) in 1,4-dioxane (5 mL) at room temperature, water was added until the mixture becomes turbid. Then lithium hydroxide monohydrate (0.054 g, 1.28 mmol) was added in one portion and the mixture stirred at room temperature for 2 h. The mixture was concentrated under reduced pressure. The crude residue was dissolved in water and acidified to pH 4.0 by dropwise addition of dilute hydrochloric acid. The solution was then extracted with DCM (2×10 mL). The combined organic layers were dried (MgSO4), filtered and concentrated under reduced pressure. The residue was dried overnight in a vacuum oven (40° C.) to yield the title compound (204) as a white powder (0.21 g).

MS 451 [M+H]$^+$

NMR (400 MHz, CDCL$_3$) $\delta_H$ 1.31 (9H, s), 3.75 (1H, dd, J 8.3, 4.7 Hz), 3.92-3.86 (3H, m), 4.02 (1H, dd, J 8.2, 6.6 Hz), 4.34-4.28 (1H, m), 5.84 (1H, s), 7.43 (2H, d, J 8.5 Hz), 7.60-7.51 (2H, m), 7.69 (1H, d, J 7.9 Hz), 8.03 (2H, d, J 8.5 Hz).

Example 154

3-[(2-(trifluoromethyl)phenyl-4'-(N,N-dimethylcarboxamide)phenyl]methoxy-N-tert-butyl-azetidine-1-carboxamide (205)

To a stirred solution of (204) (0.2 g, 0.44 mmol) in DMF (5 mL) at room temperature, was added carbonyl diimidazole (0.144 g, 0.88 mmol) and the reaction stirred for 1 h. Dimethyl amine hydrochloride (0.040 g, 0.49 mmol) and triethylamine (0.068 mL, 0.049 mmol) were added and the reaction mixture was stirred at room temperature for 3 h and then warmed to 50° C. for 18 h. The mixture was cooled to room temperature, poured into water and extracted with EtOAc. The organic layer was washed with water, brine and then dried (MgSO4), filtered and concentrated under reduced pressure. The residue was dried overnight in a vacuum oven (40° C.) to yield the title compound (205) as a white foam (0.196 g).

MS 518 [M+H]$^+$ and 516 [M−H]$^-$

LC (50/80) 99.0%, 3.82 min.

Resolution of 3-[(4-bromo)phenyl-2-(trifluoromethyl)phenyl]methoxyazetidine (198) to S-3-[(4-bromo)phenyl-2-(trifluoromethyl)phenyl]methoxyazetidine (206) and R-3-[(4-bromo)phenyl-2-(trifluoromethyl)phenyl]methoxyazetidine (208)

Compound (198) as free base and as an oil (8.42 g, 21.80 mmol) was dissolved in 2-propanol (30 mL) and the solution was added to a solution of L-tartaric acid (3.27 g, 21.79 mmol) in 2-propanol (30 mL) at 60° C., line washing with 2-propanol (20 mL). The solution was allowed to cool to <30° C., and the resulting oily suspension was diluted with ethyl acetate (50 mL), heated to 75° C., allowed to cool over 1 h, and finally cooled to 0° C. for 1 h. The crystals were collected, washed with ethyl acetate, and dried in air overnight to give the (S)-enantiomer (206) (5.044 g, 43%) as the L-tartrate.

LC (chiral AD; hexane: 2-propanol, 98:2) 90.3% at 35.5 min and 8.9% at 41.11 min after preparative derivatisation as the tert-butylurea (207).

The filtrate was concentrated in vacuo to give an orange gum (7.67 g), which was converted to the free base using a procedure similar to that described in the first paragraph, to give a yellow oil (4.63 g, 11.99 mmol, 55%). The oil was dissolved in 2-propanol (20 mL) and the solution was added to a suspension of D-tartaric acid (1.80 g, 12.0 mmol) in 2-propanol (20 mL) at 60° C., line wash 2-propanol (6 mL). The mixture crystallised, was allowed to cool to <30° C., and ethyl acetate (30 mL) was added. The suspension was heated to reflux (dissolution not observed), allowed to cool for 1 h, and cooled to 0° C. The crystals were filtered off, washed with ethyl acetate, and dried in air overnight to give the (R)-enantiomer (208) (4.815 g, 75% from D-tartaric acid) as the batch 1 D-tartrate salt.

LC (chiral AD; hexane:2-propanol, 90:10) 4.3% at 8.31 min and 95.1% at 8.99 min (91.4% ee) after preparative derivatisation as the tert-butylurea (209).

The batch 1 D-tartrate of (208), was reconverted to the free base (a necessary part of the chiral assay procedure) using the procedure given above (to give 3.49 g), and the D-tartrate formation procedure was repeated as described to give the batch 2 salt of (208), 4.41 g (92% from D-tartaric acid) (chiral LC: 1.7% at 8.34 min and 96.22% at 8.98 min=96.5% ee after preparative derivatisation as the tert-butylurea (208)).

The batch 2 D-tartrate of (208), was reconverted to the free base using the procedure given above to give (208) (3.21 g, 38% overall (maximum 50%)) as a colourless oil.

Example 155

R-3-[(4-bromo)phenyl-(2-trifluoromethyl)phenyl] methoxy-N-tert-butyl-azetidine-1-carboxamide (209)

Compound (208) (3.172 g, 8.21 mmol) was dissolved in dichloromethane (30 mL) and the solution was cooled to 0° C. and treated with tert-butyl isocyanate (1.04 mL, 0.90 g, 9.1 mmol) dropwise from a graduated pipette. The solution was stirred at 0° C. for 2.5 h and was concentrated in vacuo to give the title compound (209) as an expansive foam. The product was purified by chromatography on silica with eluent dichloromethane to ethyl acetate (3.71 g, 93%).

MS 485/487 [M+H]$^+$

LC (chiral AD, 90/10) 1.7% at 8.25 min and 95.8% at 9.09 min (96.55% ee).

?max (diffuse reflectance, KBr)/cm$^{-1}$; 3316, 3066, 2967, 1643, 1536, 1311, 1121, 1036, 1010, 960, 849, 800, 768, 658, 635, 560, 485.

LC (50/80) 99.7%, 7.2 min.

Example 156

3-[4-(4-methyl-piperazin-1-ylmethyl)phenyl-2-(trifluoromethyl)phenyl]methoxy-N-(tert-butyl)azetidine-1-carboxamide (211)

3-[4-(4-methyl-piperazin-1-ylmethyl)phenyl-2-(trifluoromethyl)phenyl]methoxy-N-(tert-butyl)azetidine-1-carboxamide (211) was prepared using the procedure given in Example 146 for compound 196, starting from compound 195 and N-methylpiperazine. Purification through an SCX-2 cartridge afforded the title compound as a white solid (32 mg, 67% yield).

Bis fumarate salt was precipitated from fumaric acid and compound (iso-propyl alcohol (24.3 gm, 28% yield).

MS 519[M+H]$^+$

LC (50/80) 86.0%, 4.34 min.

The invention claimed is:

1. A compound of formula (I):

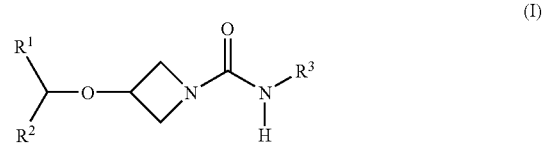

wherein:

$R^1$ and $R^2$ are independently selected from aryl; and $R^3$ is hydrogen or alkyl;

or a pharmaceutically acceptable salt thereof, wherein at least one of $R^1$ and $R^2$ has a non-hydrogen substituent in the ortho-position(s) thereof relative to the point of attachment to the [—CH—O—] group.

2. A compound according to claim 1 wherein $R^1$ and $R^2$ are independently selected from mono-cyclic aromatic groups.

3. A compound according to claim 1 wherein $R^1$ and $R^2$ are independently selected from phenyl.

4. A compound according to claim 1 wherein $R^1$ and $R^2$ are independently selected from a group of formula:

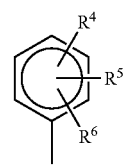

wherein $R^4$, $R^5$ and $R^6$ are independently selected from hydrogen, halo, alkyl, thioalkyl, alkoxy, alkylsulfonyl, amino, mono- and di-alkyl amino, mono- and di-aryl amino, alkylarylamino, aminoalkyl, alkylaminoalkyl, dialkylaminoalkyl, NR$^{14}$C(O)R$^{15}$, NR$^{14}$SO$_2$R$^{16}$, COOR$^{15}$, OC(O)R$^{16}$, CONR$^7$R$^8$ and SO$^2$NR$^7$R$^8$, wherein $R^7$ and $R^8$ are independently selected from hydrogen and alkyl or may form a 5 or 6 membered ring optionally containing 1 or 2 additional heteroatoms selected from N, O and S; and wherein $R^{14}$ is selected from H and lower alkyl, $R^{15}$ is selected from H, alkyl, aryl and heteroaryl and $R^{16}$ is selected from alkyl, aryl and heteroaryl.

5. A compound according to claim 1 wherein $R^1$ and $R^2$ are different.

6. A compound according to claim 4 wherein $R^4$, $R^5$ and $R^6$ are independently selected from fluoro, chloro, bromo and iodo.

7. A compound according to claim 4 wherein $R^4$, $R^5$ and $R^6$ are independently selected from alkyl, thioalkyl, alkoxy, aminoalkyl, alkylaminoalkyl, dialkylaminoalkyl and alkylsulfonyl wherein the alkyl group is selected from lower alkyl.

8. A compound according to claim 4 wherein $R^4$, $R^5$ and $R^6$ are independently selected from trifluoromethyl and difluoromethoxy.

9. A compound according to claim 4 wherein one or two of $R^4$, $R^5$ and $R^6$ are hydrogen.

10. A compound according to claim 4 wherein $R^{14}$ is selected from H.

11. A compound according to claim 4 wherein $R^{15}$ and $R^{16}$ are independently selected from alkyl.

12. A compound according to claim 4 wherein $R^{15}$ and $R^{16}$ are independently selected from lower alkyl.

13. A compound according to claim 1 wherein $R^3$ is selected from alkyl.

14. A compound according to claim 1 wherein $R^3$ is selected from tertiary butyl, isobutyl, sec-butyl and isopropyl.

15. A compound according to claim 1 wherein $R^3$ is selected from

—(CHR$^9$)$_n$(CH$_2$)$_m$CR$^{10}$R$^{11}$R$^{12}$ wherein n is 0 or 1;
m is 0, 1, 2 or 3;
$R^9$, $R^{10}$, $R^{11}$ and $R^{12}$ are selected from hydrogen, alkyl, hydroxy, alkoxy, thioalkyl, amino, mono- and di-alkyl amino, alkoxycarbonyl and $R^{13}$;
wherein $R^{13}$ is selected from aryl, heteroaryl and non-aromatic heterocyclic optionally substituted by one or more groups selected from alkyl, halogen, alkoxy, oxo, aryl, heteroaryl and non-aromatic heterocycle.

16. A compound according to claim 15 wherein m is 0 or 1.

17. A compound according to claim 15 wherein n is 0.

18. A compound according to claim 13 wherein $R^3$ is selected from cyclopentyl, cyclohexyl, norbornanyl and adamantyl.

19. A compound according to claim 1 wherein the compound is selected from:

3-(2,4,4'-trichlorobenzhydryloxy)-N-(tert-butyl)azetidine-1-carboxamide
3-(2,4'-dichlorobenzhydryloxy)-N-(tert-butyl)azetidine-1-carboxamide
3-(2,4'-dichlorobenzhydryloxy)-N-(2-thiophen-2-yl ethyl)azetidine-1-carboxamide
3-(2,4'-dichlorobenzhydryloxy)-N-(cyclopropylmethyl) azetidine-1-carboxamide
3-(2,4'-dichlorobenzhydryloxy)-N-(2,3-dihydrobenzofuran-5-yl-methyl)azetidine-1-carboxamide
3-(2,4'-dichlorobenzhydryloxy)-N-(2,5-dimethylfuran-3-yl-methyl)azetidine-1-carboxamide
3-(2,4'-dichlorobenzhydryloxy)-N-(2,3-Dihydro-benzo[1,4]dioxin-2-yl-methyl)azetidine-1-carboxamide
3-(2,4'-dichlorobenzhydryloxy)-N-(5-methyl-isoxazol-3-yl-methyl)azetidine-1-carboxamide
3-(2,4'-dichlorobenzhydryloxy)-N-[(R)-sec-butyl]azetidine-1-carboxamide
3-(2,4'-dichlorobenzhydryloxy)-N-(2-bromothiophen-3-yl-methyl)azetidine-1-carboxamide
3-(2,4'-dichlorobenzhydryloxy)-N-[(S)-sec-butyl]azetidine-1-carboxamide
3-(2,4'-dichlorobenzhydryloxy)-N-(thiophen-3-yl-methyl)azetidine-1-carboxamide
3-(2,4'-dichlorobenzhydryloxy)-N-(2-methoxyphenylmethyl)azetidine-1-carboxamide
3-(2,4'-dichlorobenzhydryloxy)-N-(2-furanylmethyl)azetidine-1-carboxamide
3-(2,4'-dichlorobenzhydryloxy)-N-(3-ethoxypropyl)azetidine-1-carboxamide
3-(2,4'-dichlorobenzhydryloxy)-N-(2-tetrahydrofuranyl-methyl)azetidine-1-carboxamide
3-(2,4'-dichlorobenzhydryloxy)-N-(exo-2-norbornanyl) azetidine-1-carboxamide
3-(2,4'-dichlorobenzhydryloxy)-N-(1-phenylpropyl)azetidine-1-carboxamide
3-(2,4'-dichlorobenzhydryloxy)-N-[(R)-a-methylbenzyl] azetidine-1-carboxamide
3-(2,4'-dichlorobenzhydryloxy)-N-[(R)-1-(3-methoxyphenyl)ethyl]azetidine-1-carboxamide
3-(2,4'-dichlorobenzhydryloxy)-N-[(S)-1-(3-methoxyphenyl)ethyl]azetidine-1-carboxamide
3-[2-(trifluoromethyl)-4'-chlorobenzhydryloxy]-N-(n-butyl)azetidine-1-carboxamide
3-[2-(trifluoromethyl)-4'-chlorobenzhydryloxy]-N-(sec-butyl)azetidine-1-carboxamide
3-[2-(trifluoromethyl)-4'-chlorobenzhydryloxy]-N-(ethyl)azetidine-1-carboxamide
3-[2-(trifluoromethyl)-4'-chlorobenzhydryloxy]-N-[(S)-a-methyl-benzyl]azetidine-1-carboxamide
3-[2-(trifluoromethyl)-4'-chlorobenzhydryloxy]-N-(2,2,4-trimethylpent-4-yl)azetidine-1-carboxamide
3-[2-(trifluoromethyl)-4'-chlorobenzhydryloxy]-N-(cyclopentyl)azetidine-1-carboxamide
3-(2,4'-dichlorobenzhydryloxy)-N-(2,2,4-trimethylpent-4-yl)azetidine-1-carboxamide
3-(2,4'-dichlorobenzhydryloxy)-N-(2-methylbut-2-yl) azetidine-1-carboxamide
3-[2-(trifluoromethyl)-2'-fluoro-4'-bromobenzhydryloxy]-N-(tert-butyl)azetidine-1-carboxamide
3-[2-(trifluoromethyl)-4'-(methylthio)benzhydryloxy]-N-(tert-butyl)azetidine-1-carboxamide
3-[2-(trifluoromethyl)-4'-(methylthio)benzhydryloxy]-N-(iso-propyl)azetidine-1-carboxamide
3-[2-(trifluoromethyl)-4'-(methylthio)benzhydryloxy]-N-(sec-butyl)azetidine-1-carboxamide
3-[2-(trifluoromethyl)-4'-(methylthio)benzhydryloxy]-N-(benzyl)azetidine-1-carboxamide
3-[2-(trifluoromethyl)-4-fluoro-4'-chlorobenzhydryloxy]-N-(tert-butyl)azetidine-1-carboxamide
3-[2-(trifluoromethyl)-4-fluoro-4'-chlorobenzhydryloxy]-N-(iso-propyl)azetidine-1-carboxamide
3-[2-(trifluoromethyl)-4-fluoro-4'-chlorobenzhydryloxy]-N-(sec-butyl)azetidine-1-carboxamide
3-[2-(trifluoromethyl)-4-fluoro-4'-chlorobenzhydryloxy]-N-(cyclohexyl)azetidine-1-carboxamide
3-[2-(trifluoromethyl)-4-fluoro-4'-chlorobenzhydryloxy]-N-(benzyl)azetidine-1-carboxamide
3-[2-(trifluoromethyl)benzhydryloxy]-N-(tert-butyl)azetidine-1-carboxamide
3-[2-(trifluoromethyl)benzhydryloxy]-N-(iso-propyl)azetidine-1-carboxamide
3-[2-(trifluoromethyl)benzhydryloxy]-N-(sec-butyl)azetidine-1-carboxamide
3-[2-(trifluoromethyl)benzhydryloxy]-N-(cyclohexyl) azetidine-1-carboxamide
3-[2-(trifluoromethyl)benzhydryloxy]-N-(benzyl)azetidine-1-carboxamide
3-[2-(trifluoromethyl)-4'-(trifluoromethoxy)benzhydryloxy]-N-(tert-butyl)azetidine-1-carboxamide
3-[2-(trifluoromethyl)-4'-(trifluoromethoxy)benzhydryloxy]-N-(iso-propyl)azetidine-1-carboxamide
3-[2-(trifluoromethyl)-4'-(trifluoromethoxy)benzhydryloxy]-N-(sec-butyl)azetidine-1-carboxamide
3-[2-(trifluoromethyl)-4'-(trifluoromethoxy)benzhydryloxy]-N-(benzyl)azetidine-1-carboxamide
3-[2-(trifluoromethyl)-4'-chlorobenzhydryloxy]-N-(1-adamantyl)azetidine-1-carboxamide
3-[2-(trifluoromethyl)-4'-chlorobenzhydryloxy]-N-(cyclohexyl)azetidine-1-carboxamide
3-[2-(trifluoromethyl)-4'-chlorobenzhydryloxy]-N-(tert-amyl)azetidine-1-carboxamide
3-[2-(trifluoromethyl)-4'-methylbenzhydryloxy]-N-(1-adamantyl)azetidine-1-carboxamide 3-[2-(trifluoromethyl)-4'-methylbenzhydryloxy]-N-(tert-butyl)azetidine-1-carboxamide 3-[2-(trifluoromethyl)-4'-methylbenzhydryloxy]-N-(cyclohexyl)azetidine-1-carboxamide 3-[2-(trifluoromethyl)-4'-methoxybenzhydryloxy]-N-(1-adamantyl)azetidine-1-carboxamide 3-[2-(trifluoromethyl)-4'-methoxybenzhydryloxy]-N-(tert-butyl)azetidine-1-carboxamide 3-[2-(trifluoromethyl)-4'-fluorobenzhydryloxy]-N-(1-adamantyl)azetidine-1-carboxamide 3-[2-(trifluoromethyl)-4'-fluorobenzhydryloxy]-N-(tert-butyl)azetidine-1-carboxamide 3-[2-(trifluoromethyl)-4'-fluorobenzhydryloxy]-N-(cyclohexyl)azetidine-1-carboxamide 3-[2-(trifluoromethyl)-4'-chlorobenzhydryloxy]-N-(allyl)azetidine-1-carboxamide 3-[2-(trifluoromethyl)-4'-(methylthio)benzhydryloxy]-N-(1-adamantyl)azetidine-1-carboxamide 3-[2-(trifluoromethyl)-4'-(methylthio)benzhydryloxy]-N-(cyclohexyl)azetidine-1-carboxamide 3-[2-(trifluoromethyl)-4'-(difluoromethoxy)benzhydryloxy]-N-(tert-butyl)azetidine-1-carboxamide 3-[2-(trifluoromethyl)-4'-(difluoromethoxy)benzhydryloxy]-N-(sec-butyl)azetidine-1-carboxamide 3-[2-(trifluoromethyl)-4'-(difluoromethoxy)benzhydryloxy]-N-(iso-propyl)azetidine-1-carboxamide 3-[2-(trifluoromethyl)-4'-(difluoromethoxy)benzhydryloxy]-N-(cyclohexyl)azetidine-1-carboxamide 3-[2-(trifluoromethyl)-4'-(difluoromethoxy)benzhydryloxy]-N-(allyl)azetidine-1-carboxamide 3-[2-(trifluoromethyl)-4'-fluorobenzhydryloxy]-N-(sec-butyl)azetidine-1-carboxamide 3-[2-(trifluoromethyl)-4'-fluorobenzhydryloxy]-N-[(S)-a-methylbenzyl]azetidine-1-carboxamide 3-[2-(trifluoromethyl)-2'-fluoro-4'-(1-piperidinyloxomethyl)benzhydryloxy]-N-(tertbutyl)azetidine-1-carboxamide 3-[2-(trifluoromethyl)-2'-fluorobenzhydryloxy]-N-(tert-butyl)azetidine-1-carboxamide, and 3-[(S*)-2-(trifluoromethyl)-4'-chlorobenzhydryloxy]-N-(tert-butyl)azetidine-1-carboxamide.

20. A pharmaceutical composition comprising a compound according to claim 1 and a suitable excipient.

21. A method of treatment of a disorder selected from the group consisting of obesity, excessive food intake, nicotine withdrawal, and nicotine dependence comprising administration to a subject in need of such treatment an effective dose of a compound of formula (I) as defined in claim 1, or a pharmaceutically acceptable salt thereof.

22. 3-[(R)-2-(trifluormethyl)-4'-chlorobenzhydryloxy]-N-(tert-butyl)azetidine-1-carboxamide.

* * * * *